United States Patent
Payne et al.

(10) Patent No.: US 11,103,583 B2
(45) Date of Patent: Aug. 31, 2021

(54) LIPIDS FOR THERAPEUTIC AGENT DELIVERY FORMULATIONS

(71) Applicant: Nitto Denko Corporation, Osaka (JP)

(72) Inventors: Joseph E. Payne, Oceanside, CA (US); John A. Gaudette, Poway, CA (US); Zheng Hou, San Diego, CA (US); Mohammad Ahmadian, Carlsbad, CA (US); Lei Yu, Carlsbad, CA (US); Victor Knopov, Oceanside, CA (US); Violetta Akopian, Oceanside, CA (US); Priya Karmali, San Diego, CA (US); Richard P. Witte, San Diego, CA (US); Neda Safarzadeh, Poway, CA (US); Wenbin Ying, San Diego, CA (US); Jun Zhang, San Diego, CA (US)

(73) Assignee: Nitto Denko Corporation, Osaka (JP)

(*) Notice: Subject to any disclaimer, the term of this patent is extended or adjusted under 35 U.S.C. 154(b) by 0 days.

(21) Appl. No.: 16/460,812

(22) Filed: Jul. 2, 2019

(65) Prior Publication Data
US 2020/0085957 A1    Mar. 19, 2020

Related U.S. Application Data

(60) Continuation of application No. 14/872,951, filed on Oct. 1, 2015, now Pat. No. 10,441,659, which is a division of application No. 13/913,918, filed on Jun. 10, 2013, now Pat. No. 9,308,267.

(60) Provisional application No. 61/657,480, filed on Jun. 8, 2012.

(51) Int. Cl.
| | | |
|---|---|---|
| *A61K 47/20* | (2006.01) | |
| *C07C 323/60* | (2006.01) | |
| *C07D 333/38* | (2006.01) | |
| *C07C 271/16* | (2006.01) | |
| *C07D 333/40* | (2006.01) | |
| *C07C 317/44* | (2006.01) | |
| *C07C 333/04* | (2006.01) | |
| *C07C 235/08* | (2006.01) | |
| *C07C 237/08* | (2006.01) | |
| *C07D 207/16* | (2006.01) | |
| *A61K 47/14* | (2017.01) | |
| *A61K 9/127* | (2006.01) | |
| *A61K 47/18* | (2017.01) | |
| *A61K 47/22* | (2006.01) | |
| *C07C 237/16* | (2006.01) | |

(52) U.S. Cl.
CPC ............ *A61K 47/20* (2013.01); *A61K 9/1272* (2013.01); *A61K 47/14* (2013.01); *A61K 47/18* (2013.01); *A61K 47/22* (2013.01); *C07C 235/08* (2013.01); *C07C 237/08* (2013.01); *C07C 237/16* (2013.01); *C07C 271/16* (2013.01); *C07C 317/44* (2013.01); *C07C 323/60* (2013.01); *C07C 333/04* (2013.01); *C07D 207/16* (2013.01); *C07D 333/38* (2013.01); *C07D 333/40* (2013.01); *Y10T 428/2998* (2015.01)

(58) Field of Classification Search
None
See application file for complete search history.

(56) References Cited

U.S. PATENT DOCUMENTS

| | | | |
|---|---|---|---|
| 5,459,127 A | 10/1995 | Felgner et al. | |
| 8,664,376 B2 | 3/2014 | Niitsu et al. | |
| 8,741,867 B2 | 6/2014 | Niitsu et al. | |
| 9,242,001 B2 | 1/2016 | Niitsu et al. | |
| 9,308,267 B2 | 4/2016 | Payne et al. | |
| 9,456,984 B2 | 10/2016 | Niitsu et al. | |
| 9,963,424 B2 | 5/2018 | Niitsu et al. | |
| 10,000,447 B2 | 6/2018 | Niitsu et al. | |
| 10,100,004 B2 | 10/2018 | Niitsu et al. | |
| 10,155,945 B2 | 12/2018 | Knopov et al. | |
| 10,195,145 B2 | 2/2019 | Niitsu et al. | |
| 10,196,637 B2 | 2/2019 | Niitsu et al. | |
| 2008/0193512 A1 | 8/2008 | Niitsu et al. | |
| 2013/0017249 A1 | 1/2013 | Niitsu et al. | |
| 2013/0022665 A1 | 1/2013 | Niitsu et al. | |
| 2013/0108685 A1* | 5/2013 | Kuboyama | C12N 15/113 424/450 |
| 2013/0115274 A1 | 5/2013 | Knopov et al. | |
| 2013/0164400 A1 | 6/2013 | Knopov et al. | |
| 2016/0074514 A1 | 3/2016 | Payne et al. | |
| 2018/0208547 A1 | 7/2018 | Niitsu et al. | |
| 2018/0297938 A1 | 10/2018 | Niitsu et al. | |

FOREIGN PATENT DOCUMENTS

| | | | |
|---|---|---|---|
| CA | 2800818 | 11/2011 | |
| JP | 2006-254877 A | 9/2006 | |
| RU | 2013158456 A | 7/2015 | |
| WO | WO 2006/068232 A1 | 6/2006 | |
| WO | WO 2011/136368 A1 | 11/2011 | |
| WO | WO-2011136368 A1 * | 11/2011 | ............ A61K 47/186 |
| WO | WO 2012/170952 A2 | 12/2012 | |
| WO | WO 2012/170957 A2 | 12/2012 | |

(Continued)

OTHER PUBLICATIONS

U.S. Appl. No. 12/294,021, filed Jun. 2, 2014, Niitsu et al.
U.S. Appl. No. 14/256,306, filed Apr. 18, 2014, Niitsu et al.
Moss, "Nomenclature of Retinoids", Biochemical Nomenclature and Related Documents, 2nd Edition, Portland Press, 1992, pp. 247-251.
Fingl et al., "The Pharmacological Basis of Therapeutics", 1975, Chapter 1 (p. 1), 6 pages.
International Patent Application No. PCT/US2013/044849: International Search Report dated Sep. 11, 2013, 10 pages.
Japan Patent Application No. 2015-516267; Reasons for Refusal; dated Jul. 29, 2015; 9 pages.

(Continued)

*Primary Examiner* — Celeste A Roney
(74) *Attorney, Agent, or Firm* — Knobbe Martens Olson & Bear, LLP

(57) ABSTRACT

The description is directed to ionizable lipids useful for enhancing the delivery of therapeutic agents in liposomes.

17 Claims, 4 Drawing Sheets

Specification includes a Sequence Listing.

(56) References Cited

FOREIGN PATENT DOCUMENTS

WO     WO 2013/096348 A1    6/2013
WO     WO 2013/185116 A1    12/2013

OTHER PUBLICATIONS

China Patent Application No. 201380041854.8; Office Action; dated Dec. 1, 2015; 17 pages.
China Patent Application No. 201380041854.8; Office Action; dated Sep. 28, 2016; 13 pages (w/ English Translation).
Australia Patent Application No. 2013270685; Office Action; dated Nov. 11, 2016; 3 pages.
Taiwan Patent Application No. 102120444; Office Action; dated Jan. 16, 2017; 9 pages.
China Patent Application No. 201380041854.8; Office Action; dated Jun. 5, 2017; 12 pages.
European Patent Application No. 18200656.9; Extended Search Report; dated Apr. 4, 2019; 7 pages.
Brazil Patent Application No. 112014030714-8; Written Opinion Search Report; dated Aug. 5, 2019; 8 pages.
Brazil Patent Application No. 112014030714-8; Technical Examination Report; dated Mar. 3, 2020; 7 pages.
European Patent Application No. 18200656.9; Office Action—Article 94(3); dated Apr. 20, 2020; 4 pages.
Korean Patent Application No. 10-2015-7000454; Office Action; dated Oct. 2, 2019; 17 pages.

\* cited by examiner

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
ggacaggccu cuacaacuat t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
uaguuguaga ggccugucct t                                              21

<210> SEQ ID NO 3
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
ggacaggccu guacaacuat t                                                   21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
uaguuguaca ggccugucct t                                                   21
```

LIPIDS FOR THERAPEUTIC AGENT DELIVERY FORMULATIONS

CROSS REFERENCE TO RELATED APPLICATIONS

This application is a continuation of U.S. patent application Ser. No. 14/872,951 filed on Oct. 1, 2015, which is a divisional of U.S. patent application Ser. No. 13/913,918 filed on Jun. 10, 2013, now U.S. Pat. No. 9,308,267, which claims the benefit of U.S. Provisional patent application No. 61/657,480 filed Jun. 8, 2012, which are herein incorporated by reference in their entirety.

SEQUENCE LISTING

The instant application contains a Sequence Listing which has been filed electronically in ASCII format and is hereby incorporated by reference in its entirety. Said ASCII copy, created on Oct. 16, 2019, is named 101025_000063_SL.txt and is 1,661 bytes in size.

TECHNICAL FIELD

The description is directed to ionizable lipids for enhancing the delivery of therapeutic agents.

BACKGROUND

A number of techniques are available for delivering a therapeutic agent, for example, siRNA, nucleic acids, etc., into a cell. These techniques include viral and non-viral transfection systems. Non-viral transfection systems can include, for example, polymers, lipids, liposomes, micelles, dendrimers, and nanomaterials. Polymers that have been studies for cell transfection include cationic polymers such as, for example, poly(L-lysine) ("PLL"), polyethyleneimine ("PEP"), chitosan, and poly(2-dimethylamino)ethyl methacrylate ("pDMAEMA").

The viral and non-viral transfection techniques have drawbacks, however. For example, viral systems can yield high transfection efficiency, but may not be entirely safe. In addition, viral systems can be complicated and/or expensive to prepare.

Non-viral transfection systems, for example, those employing cationic polymers, have been reported to transfer plasmid DNA into cells. Cationic polymers, however, can be unstable and can be toxic to cells.

As such, there is a need for new compounds, compositions, and methods for using cationic composition to improve the delivery of therapeutic agents to cells, tissues, and organisms.

SUMMARY

The present description is directed to ionizable lipid compounds of formula I

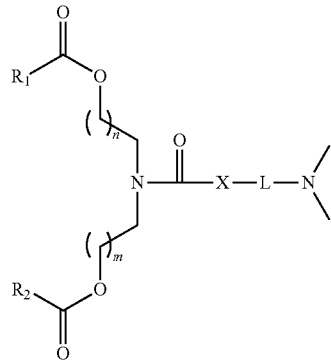

wherein n and m are independently 1, 2, 3, or 4; $R_1$ and $R_2$ are independently $C_{10-18}$ alkyl or $C_{12-18}$ alkenyl; X is —$CH_2$—, S, O, N, or absent; L is $C_{1-4}$ alkylene; —S—$C_{1-4}$ alkylene; —O—$C_{1-4}$ alkylene; —O—C(O)—$C_{1-4}$ alkylene; —S(O)$_2$—$C_{1-4}$ alkylene;

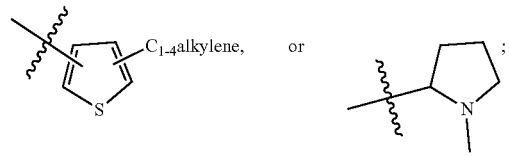

or a pharmaceutically acceptable salt form thereof. Compositions, pharmaceutical formulations, drug carriers, and methods of using the compounds of formula I are also described.

DETAILED DESCRIPTION OF ILLUSTRATIVE EMBODIMENTS

Figure 1:
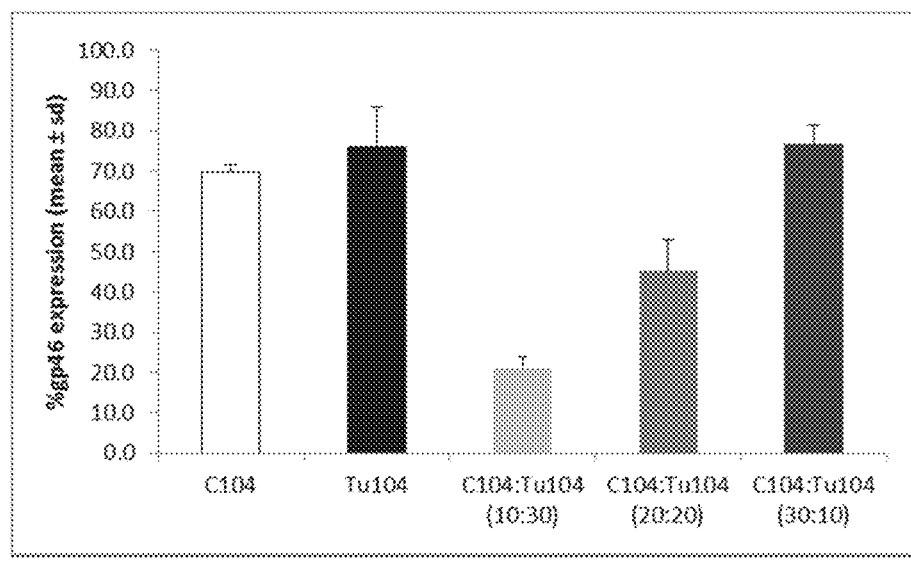
FIG. 1 depicts in vitro synergistic efficacy of ionizable lipid:ionizable lipid embodiments of the present description

The present description is directed to ionizable lipid compounds, as well as their uses in delivering therapeutic agents to cells, tissues, and organisms.

Within the scope of the description are ionizable lipid compounds of formula I:

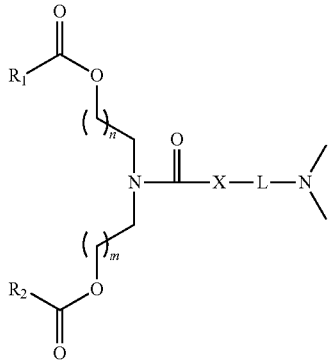

wherein
n and m are independently 1, 2, 3, or 4;
$R_1$ and $R_2$ are independently $C_{10-18}$ alkyl or $C_{12-18}$ alkenyl;
X is —$CH_2$—, S, O, N, or absent;
L is $C_{1-4}$ alkylene; —S—$C_{1-4}$ alkylene; —O—$C_{1-4}$ alkylene; —O—C(O)—$C_{1-4}$ alkylene; —S(O)$_2$—$C_{1-4}$ alkylene;

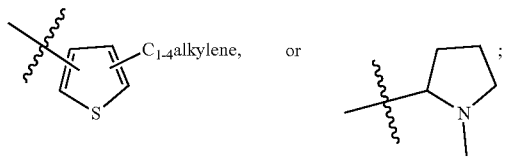

or a pharmaceutically acceptable salt form thereof.

Within the scope of the description, n and m can be the same or different. In preferred embodiments, n and m are the same. Particularly preferred are those embodiments wherein n and m are both 1 or n and m are both 2.

In some embodiments of the description, X is a bond. In other embodiments, X is —$CH_2$—. In still others, X is S. Also preferred, are embodiments wherein X is O. Embodiments wherein X is N are also within the scope of the description.

In some embodiments of the description, L is $C_{1-4}$ alkylene. In other embodiments, L is —S—$C_{1-4}$ alkylene. In yet other embodiments, L is —O—$C_{1-4}$ alkylene. In still other embodiments, L is —O—C(O)—$C_{1-4}$ alkylene. Alternatively, L is —S(O)$_2$—$C_{1-4}$ alkylene. Also within the scope of the description are embodiments wherein L is

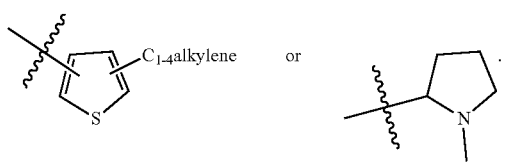

In those embodiments wherein X is a bond, L is preferably $C_{1-4}$ alkylene. Such examples of L include —$CH_2$—, —$CH_2$—$CH_2$—, —$CH_2$ $CH_2CH_2$—, and —$CH_2$ $CH_2CH_2CH_2$—. In other embodiments wherein X is a bond, L is

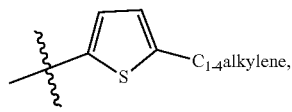

for example,

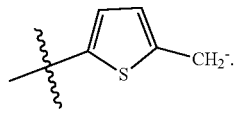

In those embodiments wherein X is —$CH_2$—, L is preferably —S—$C_{1-4}$ alkylene. Such examples of L include —S—$CH_2$—, —S—$CH_2$—$CH_2$—, —S—$CH_2$ $CH_2CH_2$—, and —S—$CH_2$ $CH_2CH_2CH_2$—.

In other embodiments wherein X is —$CH_2$—, L is preferably —S(O)$_2$—$C_{1-4}$ alkylene. Such examples of L include —S(O)$_2$—$CH_2$—, —S(O)$_2$—$CH_2$—$CH_2$—, —S(O)$_2$—$CH_2$—$CH_2$—$CH_2$—, and S(O)$_2$—$CH_2$—$CH_2$—$CH_2$—$CH_2$—.

In yet other embodiments wherein X is —$CH_2$—, L is —O—$C_{1-4}$ alkylene. Such examples of L include —O—$CH_2$—, —O—$CH_2$—$CH_2$—, —O—$CH_2$ $CH_2CH_2$—, and —O—$CH_2$ $CH_2CH_2CH_2$—.

In those embodiments of the description wherein X is S, L is preferably $C_{1-4}$alkylene. Such examples of L include —$CH_2$—, —$CH_2$—$CH_2$—, —$CH_2$ $CH_2CH_2$—, and —$CH_2$ $CH_2CH_2CH_2$—.

In those embodiments wherein X is O, L is preferably $C_{1-4}$ alkylene. Such examples of L include —$CH_2$—, —$CH_2$—$CH_2$—, —$CH_2$ $CH_2CH_2$—, and —$CH_2$ $CH_2CH_2CH_2$—.

Within the scope of the description, $R_1$ and $R_2$ can be the same or different. Preferably, $R_1$ and $R_2$ are the same. Preferably, $R_1$ and $R_2$ are $C_{10-18}$ alkyl. Also preferred are embodiments wherein the $C_{10-18}$ alkyl is a straight-chain $C_{10-18}$ alkyl. More preferred are embodiments wherein $R_1$ and $R_2$ are $C_{12-18}$ alkyl. Also preferred are embodiments wherein $R_1$ and $R_2$ are $C_{12-15}$ alkyl. In most preferred embodiments, $R_1$ and $R_2$ are both $C_{13}$ alkyl.

In other embodiments of the description, $R_1$ and $R_2$ are $C_{12-18}$ alkenyl. Preferably, $R_1$ and $R_2$ are $C_{13-17}$ alkenyl. More preferably, $R_1$ and $R_2$ are each oleyl:

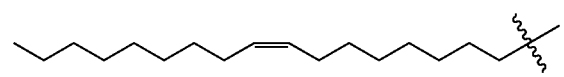 [SMILES: *CCCCCCC/C=C\CCCCCCCC]

In other embodiments of the description, $R_1$ and $R_2$ are $C_{12-18}$ alkenyl. Preferably, $R_1$ and $R_2$ are $C_{13-17}$ alkenyl. More preferably, $R_1$ and $R_2$ are each linoleoyl.

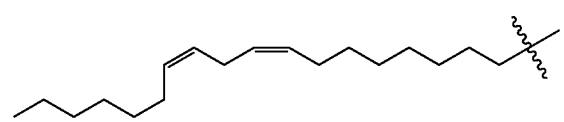 [SMILES: *CCCCCCC/C=C\C/C=C\CCCCCC]

Also within the scope of the description are compositions comprising a compound of formula I in a liposome, wherein the liposome comprises a bilayer of lipid molecules. While the compound of formula I can comprise any mole percentage of the lipid molecules in such compositions, it is preferred that the compound of formula I is about 5 to about 50 mol % of the lipid molecules of the compositions of the description.

Compositions of the description comprising a compound of formula I in a liposome can contain more than one compound of formula I. In preferred embodiments, such compositions of the description include two compounds of formula I. In those embodiments, it is preferred that the molar ratio of the two compounds of formula I is about 10:30 to about 30:10.

Compositions of the description comprising a compound of formula I in a liposome may further comprise a cationic lipid. In such embodiments, the cationic lipid is about 5 to about 40 mol % of the lipid molecules of the composition. Also in these embodiments comprising a compound of formula I in a liposome with a cationic lipid, the molar ratio of the compound of formula I to the cationic lipid is about 5:35 to about 35:5. More preferable, the ratio is about 10:30 to about 30:10.

Within the scope of the description, any compositions of the description may further comprise a liquid medium. Preferably, the liquid medium is suitable for injection into a living organism. In some embodiments, the liquid medium comprises an organic solvent. Alternatively, the liquid medium used in certain embodiments of the description comprises water and an organic solvent. In other embodiments of the description, the liquid medium may further comprise a non-aqueous medium.

consisting of a (retinoid)$_n$-linker-(retinoid)$_n$, wherein n=0, 1, 2 or 3; and wherein the linker comprises a polyethylene glycol (PEG) or PEG-like molecule.

In preferred embodiments, the drug carriers of the description will further comprising a siRNA molecule.

Also within the scope of the description are pharmaceutical formulations. Pharmaceutical formulations within the scope of the description include any of the aforementioned drug carrier of the description and a pharmaceutically acceptable carrier or diluent. In is preferred that in such formulations, the siRNA is encapsulated by the liposome of the compositions of the description.

Also within the scope of the description are methods of delivering a drug to a patient in need of treatment. These methods comprise providing a pharmaceutical formulation within the scope of the description and administering the pharmaceutical formulation to the patient.

Definitions

The following terms are used throughout this specification.

As used herein, "cationic lipid" refers to a compound that includes at least one lipid moiety and a positively charged quaternary nitrogen associated with a counterion. "Lipids" are understood in the art to be comprises of a hydrophobic alkyl or alkenyl moiety and a carboxylic acid or ester moiety. Preferred cationic lipids for use in the present description include:

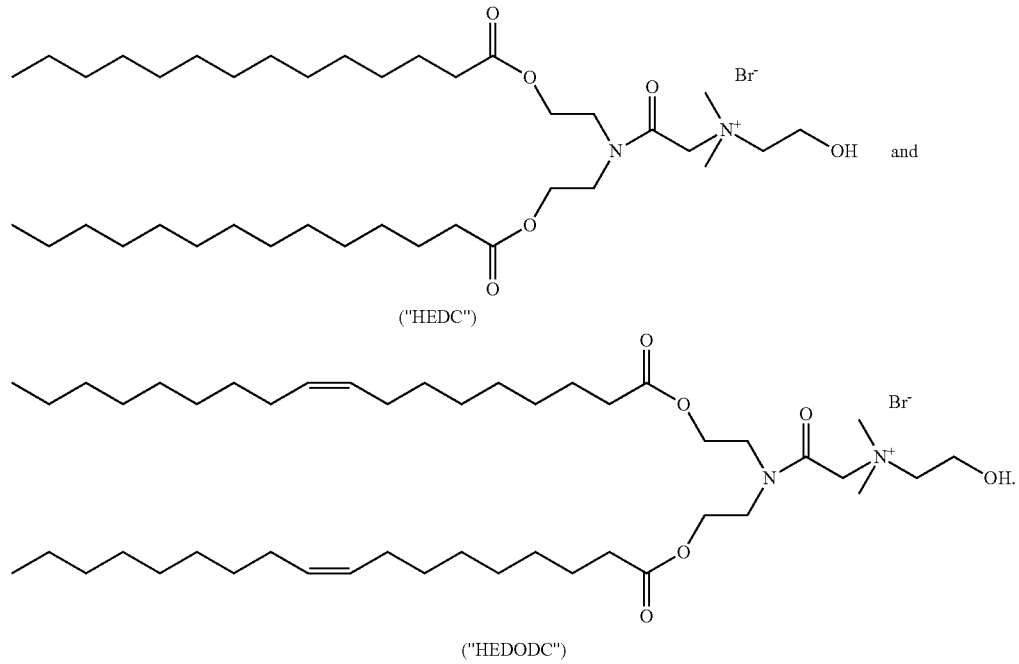

("HEDC")

("HEDODC")

Also within the scope of the description, any compositions of the description may further comprise at least one phospholipid.

In other embodiments of the description, any compositions of the description may further comprise at least one PEG-conjugated lipid.

Also within the scope of the description are stellate-cell-specific drug carriers. These embodiments of the description include any of the aforementioned compositions, as well as a stellate cell specific amount of a targeting molecule As used herein, "ionizable lipid" refers to a compound of formula I within the scope of the description. These compounds are capable of forming charged species when contacted with an appropriate counterion species, for example, a species that includes an ionizable hydrogen atom.

As used herein, "alkyl" refers to a straight or branched fully saturated (no double or triple bonds) hydrocarbon group, for example, a group having the general formula —$C_nH2_{n+1}$. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, isopropyl, n-butyl, isobutyl, sec-butyl, and t-butyl. Typical alkyl groups include, but are in no way limited to, methyl, ethyl, propyl, isopropyl, butyl, isobutyl, tertiary butyl, pentyl, hexyl and the like.

As used herein, "alkylene" refers to an alkanediyl functional group, for example, —$CH_2$—, —$CH_2CH_2$—, —$CH_2CH_2CH_2$—, —$CH_2CH_2CH_2CH_2$—, and the like.

As used herein, "alkenyl" refers to an alkyl group that contains in the straight or branched hydrocarbon chain one or more double bonds. An alkenyl group may be unsubstituted or substituted. When substituted, the substituent(s) may be selected from the same groups disclosed above with regard to alkyl group substitution unless otherwise indicated. Oleyl is an example of such an alkenyl group.

As used herein, the term "pharmaceutical carrier" refers to a chemical compound that facilitates the incorporation of a compound into cells or tissues. For example dimethyl sulfoxide (DMSO) is a commonly utilized carrier as it facilitates the uptake of many organic compounds into the cells or tissues of an organism.

As used herein, the term "diluent" refers to chemical compounds diluted in water that will dissolve the formulation of interest (e.g., the formulation that can include a compound, a retinoid, a second lipid, a stabilizing agent, and/or a therapeutic agent) as well as stabilize the biologically active form of the formulation. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of the formulation. As used herein, an "excipient" refers to an inert substance that is added to a formulation to provide, without limitation, bulk, consistency, stability, binding ability, lubrication, disintegrating ability, etc., to the composition. A "diluent" is a type of excipient.

"Organic solvents" used within the scope of the description are known in the art, per se. and include, for example, $C_{1-4}$alkyl alcohols, dimethyl sulfoxide ("DMSO"), and the like.

As used herein, "therapeutic agent" refers to a compound that, upon administration to a mammal in a therapeutically effective amount, provides a therapeutic benefit to the mammal. A therapeutic agent may be referred to herein as a drug. Those skilled in the art will appreciate that the term "therapeutic agent" is not limited to drugs that have received regulatory approval. A "therapeutic agent" can be operatively associated with a compound as described herein, a retinoid, and/or a second lipid. For example, a second lipid as described herein can form a liposome, and the therapeutic agent can be operatively associated with the liposome, e.g., as described herein.

As used herein, a "retinoid" is a member of the class of compounds consisting of four isoprenoid units joined in a head-to-tail manner, see G. P. Moss, "Biochemical Nomenclature and Related Documents," 2nd Ed. Portland Press, pp. 247-251 (1992). "Vitamin A" is the generic descriptor for retinoids exhibiting qualitatively the biological activity of retinol. As used herein, retinoid refers to natural and synthetic retinoids including first generation, second generation, and third generation retinoids. Examples of naturally occurring retinoids include, but are not limited to, (1) 11-cis-retinal, (2) all-trans retinol, (3) retinyl palmitate, (4) all-trans retinoic acid, and (5) 13-cis-retinoic acids. Furthermore, the term "retinoid" encompasses a retinols, retinal, retinoic acid, retinoid, and derivatives thereof.

As used herein, "retinoid conjugate" refers to a molecule that includes at least one retinoid moiety. In preferred embodiments of the description, the retinoid conjugate will be present at a concentration of about 0.3 to about 30 weight percent, based on the total weight of the composition or formulation, which is equivalent to about 0.1 to about 10 mol. %, which is equivalent to a molar ratio of about 0.1 to about 10. Preferably, the retinoid conjugate is a retinoid-linker-lipid molecule or a retinoid-linker-retinoid molecule.

An example of a retinoid conjugates include those compounds of formula II:

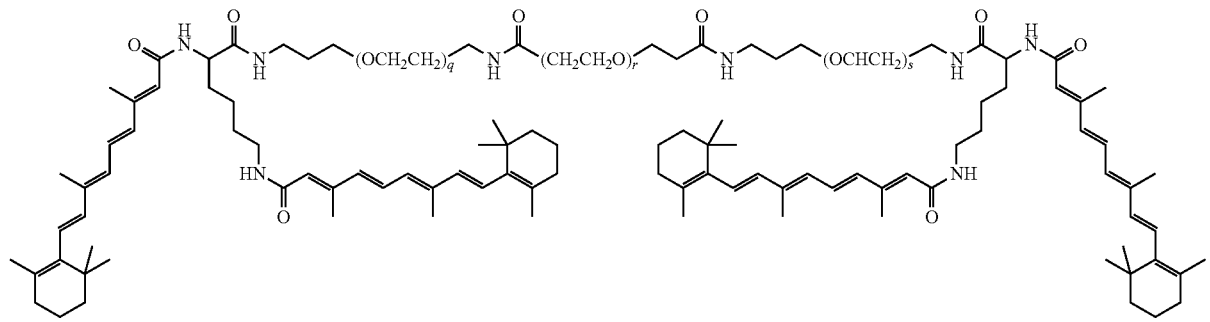

II wherein q, r, and s are each independently 1, 2, 3, 4, 5, 6, 7, 8, 9, or 10, and enantiomers and diastereomers thereof.

Preferred compounds of formula II include those wherein q, r, and s are each independently 1, 2, 3, 4, 5, 6, or 7. More preferred are those compounds of formula II wherein q, r, and s are each independently 3, 4, or 5. Most preferred are those compounds of formula II wherein q is 3, r is 5, and s is 3. One example of a compound of formula II is

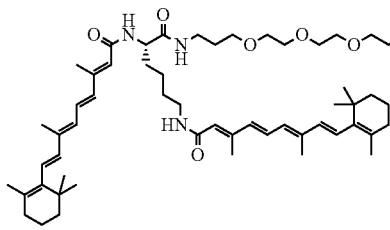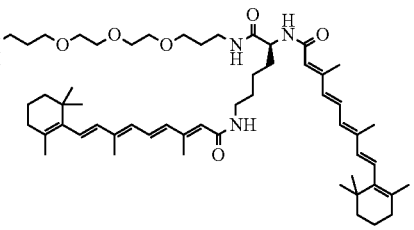

DiVA-PEG-DiVA

DiVA-PEG-DiVA includes stereocenters and all enantiomers and diastereomers are considered to be within the scope of the description.

As used herein, "retinoid-linker-lipid molecule" refers to a molecule that includes at least one retinoid moiety attached to at least one lipid moiety through at least one linker such as, for example, a PEG moiety.

As used herein, "retinoid linker-retinoid molecule" refers to a molecule that includes at least one retinoid moiety attached to at least one other retinoid moiety (which may be the same or different) through at least one linker such as, for example, a PEG moiety.

As used herein, the terms "lipid" and "lipophilic" are used herein in their ordinary meanings as understood by those skilled in the art. Non-limiting examples of lipids and lipophilic groups include fatty acids, sterols, $C_2$-$C_{50}$ alkyl, $C_2$-$C_{50}$ heteroalkyl, $C_2$-$C_{50}$ alkenyl, $C_2$-$C_{50}$ heteroalkenyl, $C_2$-$C_{50}$ aryl, $C_2$-$C_{50}$ heteroaryl, $C_2$-$C_{50}$ alkynyl, $C_2$-$C_{50}$ heteroalkynyl, $C_2$-$C_{50}$ carboxyalkenyl, and $C_2$-$C_{50}$ carboxyheteroalkenyl. A fatty acid is a saturated or unsaturated long-chain monocarboxylic acid that contains, for example, 12 to 24 carbon atoms A lipid is characterized as being essentially water insoluble, having a solubility in water of less than about 0.01% (weight basis). As used herein, the terms "lipid moiety" and "lipophilic moiety" refers to a lipid or portion thereof that has become attached to another group. For example, a lipid group may become attached to another compound (e.g., a monomer) by a chemical reaction between a functional group (such as a carboxylic acid group) of the lipid and an appropriate functional group of a monomer.

As used herein, "stellate cell" hepatic stellate cells.

As used herein, "siRNA" refers to small interfering RNA, also known in the art as short interfering RNA or silencing RNA. siRNA is a class of double stranded RNA molecules that have a variety of effects known in the art, the most notable being the interference with the expression of specific genes and protein expression.

The term "liposome" is used herein in its ordinary meaning as understood by those skilled in the art, and refers to a lipid bilayer structure that contains lipids attached to polar, hydrophilic groups which form a substantially closed structure in aqueous media. In some embodiments, the liposome can be operatively associated with one or more compounds, such as a therapeutic agent and a retinoid. A liposome may be comprised of a single lipid bilayer (i.e., unilamellar) or it may comprised of two or more lipid bilayers (i.e., multilamellar). While the interior of a liposome may consists of a variety of compounds, the exterior of the liposome is accessible to the aqueous formulation comprising the liposome. A liposome can be approximately spherical or ellipsoidal in shape.

In some embodiments, the siRNA will be encapsulated by the liposome so that the siRNA is inaccessible to the aqueous medium. When encapsulating siRNA, the liposome will have a solid core; such liposomes encapsulating siRNA and having a solid core are termed "lipid nanoparticles" herein. In other embodiments, the siRNA will not be encapsulated by the liposome. In such embodiments, the siRNA can be complexed on the outer surface of the liposome by mixing preformed liposomes with RNA in an aqueous solution. In these embodiments, the siRNA is accessible to the aqueous medium. Liposomes having siRNA bound only on their outer surface are termed "lipoplexes" herein.

The formulations of the description can also include PEG-conjugated lipids. PEG-conjugated lipids within the scope of the description are known in the art per se. Suitable PEG-lipids include PEG-phospholipids and PEG-ceramides such as, for example, PEG2000-DSPE, PEG2000-DPPE, PEG2000-DMPE, PEG2000-DOPE, PEG1000-DSPE, PEG1000-DPPE, PEG1000-DMPE, PEG1000-DOPE, PEG550-DSPE, PEG550-DPPE, PEG-550DMPE, PEG-1000DOPE, PEG-BML, PEG-Cholesterol. PEG2000-Ceramide, PEG1000-Ceramide, PEG750-Ceramide, PEG550-Ceramide.

The foregoing compositions of the description can include one or more phospholipids such as, for example, 1,2-distearoyl-sn-glycero-3-phosphocholine ("DSPC"), dipalmitoylphosphatidylcholine ("DPPC"), 1,2-dipalmitoyl-sn-glycero-3-phosphoethanolamine ("DPPE"), and 1,2-dioleoyl-sn-glycero-3-phosphoethanolamine ("DOPE"). Preferably, the helper lipid is DOPE.

Also within the scope of the description are pharmaceutical formulations that include any of the aforementioned compositions in addition to a pharmaceutically acceptable carrier or diluent. Pharmaceutical formulations of the description will include at least one therapeutic agent. Preferably, the therapeutic agent is an siRNA. It is envisioned that any siRNA molecule can be used within the scope of the description. For example, siRNA may include:

```
Sense (5'->3')
                                    (SEQ. ID. NO. 1)
GGACAGGCCUCUACAACUATT Antisense (3'->5')
                                    (SEQ. ID. NO. 2)
TTCCUGUCCGGAGAUGUUGAU
and Sense (5'->3')
                                    (SEQ. ID. NO. 3)
GGACAGGCCUGUACAACUATT Antisense (3'->5')
                                    (SEQ. ID. NO. 4)
TTCCUGUCCGGACAUGUUGAU
```

In preferred formulations of the description including siRNA, the siRNA is encapsulated by the liposome. In other embodiments, the siRNA can be outside of the liposome. In those embodiments, the siRNA can be complexed to the outside of the liposome.

Also within the scope of the description are methods of delivering a therapeutic agent to a patient. These methods comprise providing a pharmaceutical formulation including any of the foregoing compositions and a pharmaceutically acceptable carrier or diluent; and administering the pharmaceutical formulation to the patient.

In another aspect, the present disclosure relates to a pharmaceutical formulation comprising one or more physiologically acceptable surface active agents, pharmaceutical carriers, diluents, excipients, and suspension agents, or a combination thereof; and a formulation (e.g., the formulation that can include a compound, a retinoid, a second lipid, a stabilizing agent, and/or a therapeutic agent) disclosed herein. Acceptable additional pharmaceutical carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, and the like may be provided in the pharmaceutical formulation. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical formulations described herein can be administered to a human patient per se, or in pharmaceutical formulations where they are mixed with other active ingredients, as in combination therapy, or suitable pharmaceutical carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may include, for example, parenteral delivery, including intramuscular, subcutaneous, intravenous, intramedullary injections, as well as intrathecal, direct intraventricular, intraperitoneal, intranasal, or intraocular injections. The formulation (e.g., the formulation that can include a compound, a retinoid, a second lipid, a stabilizing agent, and/or a therapeutic agent) can also be administered in sustained or controlled release dosage forms, including depot injections, osmotic pumps, and the like, for prolonged and/or timed, pulsed administration at a predetermined rate. Additionally, the route of administration may be local or systemic.

The pharmaceutical formulations may be manufactured in a manner that is itself known, e.g., by means of conventional mixing, dissolving, granulating, dragee-making, levigating, emulsifying, encapsulating, entrapping or tableting processes.

Pharmaceutical formulations may be formulated in any conventional manner using one or more physiologically acceptable pharmaceutical carriers comprising excipients and auxiliaries which facilitate processing of the active compounds into preparations which can be used pharmaceutically. Proper formulation is dependent upon the route of administration chosen. Any of the well-known techniques, pharmaceutical carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical formulations may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

Pharmaceutical formulations for parenteral administration, e.g., by bolus injection or continuous infusion, include aqueous solutions of the active formulation (e.g., the formulation that can include a compound, a retinoid, a second lipid, a stabilizing agent, and/or a therapeutic agent) in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the preparations described previously, the formulations may also be formulated as a depot preparation. Such long acting formulations may be administered by intramuscular injection. Thus, for example, the formulations (e.g., the formulation that can include a compound, a retinoid, a second lipid, a stabilizing agent, and/or a therapeutic agent) may be formulated with suitable polymeric or hydrophobic materials (for example as an emulsion in an acceptable oil) or ion exchange resins, or as sparingly soluble derivatives, for example, as a sparingly soluble salt.

The compositions and formulations of the description may also be formulated for topical delivery and may be applied to the subject's skin using any suitable process for application of topical delivery vehicle. For example, the formulation may be applied manually, using an applicator, or by a process that involves both. Following application, the formulation may be worked into the subject's skin, e.g., by rubbing. Application may be performed multiple times daily or on a once-daily basis. For example, the formulation may be applied to a subject's skin once a day, twice a day, or multiple times a day, or may be applied once every two days, once every three days, or about once every week, once every two weeks, or once every several weeks.

Some embodiments herein are directed to a method of delivering a therapeutic agent to a cell. For example, some embodiments are directed to a method of delivering a therapeutic agent such as siRNA into a cell. Suitable cells for use according to the methods described herein include prokaryotes, yeast, or higher eukaryotic cells, including plant and animal cells (e.g., mammalian cells). In some embodiments, the cells can be human fibrosarcoma cells (e.g., HT1080 cell line). In other embodiments, the cells can be hepatic stellate cells (LX2 cell line). In other embodiments, the cells can be cancer cells. In yet other embodiments, the cells can be stem cells (pHSC cell line). Cell lines which are model systems for cancer may be used, including but not limited to breast cancer (MCF-7, MDA-MB-438 cell lines), U87 glioblastoma cell line, B16F0 cells (melanoma), HeLa cells (cervical cancer), A549 cells (lung cancer), and rat tumor cell lines GH3 and 9L. In these embodiments, the formulations described herein can be used to transfect a cell. These embodiments may include contacting the cell with a formulation described herein that includes a therapeutic agent, to thereby deliver a therapeutic agent to the cell.

Disclosed herein are methods for treating a condition characterized by abnormal fibrosis, which may include administering a therapeutically effective amount of a formulation described herein. Conditions characterized by abnormal fibrosis may include cancer and/or a fibrotic disease. Types of cancer that may be treated or ameliorated by a formulation described herein include, but are not limited to, lung cancer, pancreatic cancer, breast cancer, liver cancer, stomach cancer, and colon cancer. In an embodiment, the cancer that may be treated or ameliorated is pancreatic cancer. In another embodiment, the cancer that may be treated or ameliorated is lung cancer. Types of fibrotic disease that may be treated or ameliorated by a formulation described herein include, but are not limited to, hepatic fibrosis, hepatic cirrhosis, pancreatitis, pancreatic fibrosis, cystic fibrosis, vocal cord scarring, vocal cord mucosal fibrosis, laryngeal fibrosis, pulmonary fibrosis, idiopathic pulmonary fibrosis, cystic fibrosis, myelofibrosis, retroperitoneal fibrosis, and nephrogenic systemic fibrosis. In an embodiment, the condition that may be treated or ameliorated is hepatic fibrosis.

The formulations or pharmaceutical compositions described herein may be administered to the subject by any suitable means. Non-limiting examples of methods of administration include, among others, (a) administration via injection, subcutaneously, intraperitoneally, intravenously, intramuscularly, intradermally, intraorbitally, intracapsularly, intraspinally, intrasternally, or the like, including infusion pump delivery; (b) administration locally such as by injection directly in the renal or cardiac area, e.g., by depot implantation; as well as deemed appropriate by those of skill in the art for bringing the active compound into contact with living tissue.

Pharmaceutical compositions suitable for administration include formulations (e.g., the formulation that can include a compound, a retinoid, a second lipid, a stabilizing agent, and/or a therapeutic agent) where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some condition, the dosages will be about the same, or dosages that are about 0.1% to about 500%, more preferably about 25% to about 250% of the established human dosage. Where no human dosage is established, as will be the case for newly-discovered pharmaceutical compositions, a suitable human dosage can be inferred from ED50 or ID50 values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, a dose of about 0.1 mg to 2000 mg of each active ingredient, preferably about 1 mg to about 500 mg, e.g. 5 to 200 mg. In other embodiments, an intravenous, subcutaneous, or intramuscular dose of each active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free base. In some embodiments, the formulation is administered 1 to 4 times per day. Alternatively the formulations may be administered by continuous intravenous infusion, preferably at a dose of each active ingredient up to about 1000 mg per day. As will be understood by those of skill in the art, in certain situations it may be necessary to administer the formulations disclosed herein in amounts that exceed, or even far exceed, the above-stated, preferred dosage range in order to effectively and aggressively treat particularly aggressive diseases or infections. In some embodiments, the formulations will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of formulation administered may be dependent on the subject being treated, on the subject's weight, the severity of the affliction, the manner of administration and the judgment of the prescribing physician.

Formulations disclosed herein (e.g., the formulation that can include a compound, a retinoid, a second lipid, a stabilizing agent, and/or a therapeutic agent) can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

It is understood that, in any compound described herein having one or more stereocenters, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z a mixture thereof. Likewise, all tautomeric forms are also intended to be included.

Preferred compounds of formula I within the scope of the description are set forth in Table 1. In vitro and in vivo data (see infra) is also set forth in Table 1.

TABLE 1

| Lipid | Structure | in vitro (pHSC) % KD | in vivo (rat DMNQ) % KD |
|---|---|---|---|
| i-Pr-DC | 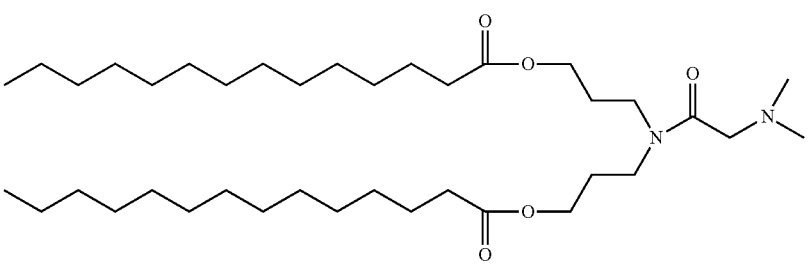 [SMILES: CCCCCCCCCCCCCC(=O)OCCCN(CCCOC(=O)CCCCCCCCCCCCC)C(=O)CN(C)C] | | 53% @ 50 nM |

TABLE 1-continued

| Lipid | Structure | in vitro (pHSC) % KD | in vivo (rat DMNQ) % KD |
|---|---|---|---|
| i-Pr-DODC | 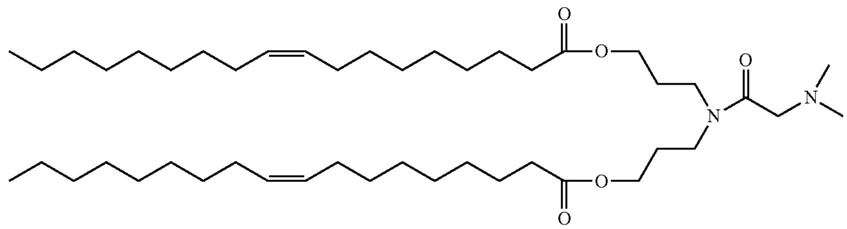 [SMILES: CCCCCCCC/C=C\CCCCCCCC(=O)OCCCN(CCCOC(=O)CCCCCCC/C=C\CCCCCCCC)C(=O)CN(C)C] | 60% @ 50 nM | |
| i-DC | 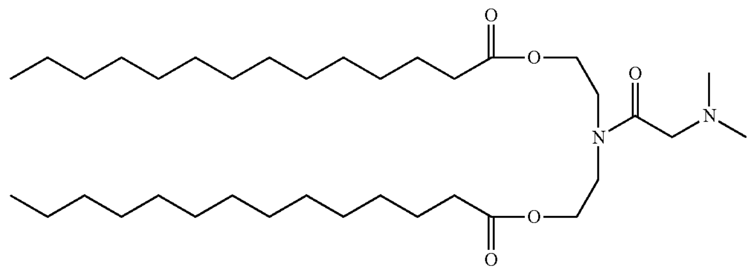 [SMILES: CCCCCCCCCCCCCC(=O)OCCN(CCOC(=O)CCCCCCCCCCCCC)C(=O)CN(C)C] | 89% @ 200 nM | |
| i-Et-DC (Et104) | 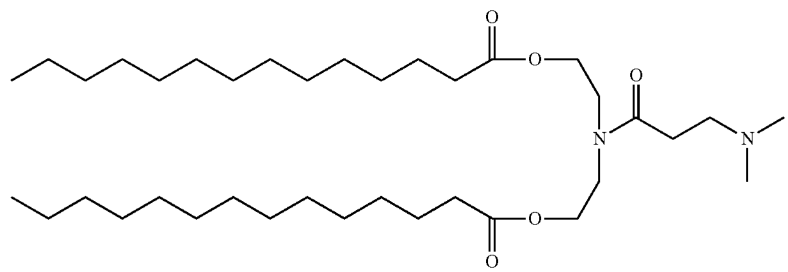 [SMILES: CCCCCCCCCCCCCC(=O)OCCN(CCOC(=O)CCCCCCCCCCCCC)C(=O)CCN(C)C] | 65% @ 50 nM | |
| i-Et-DODC | 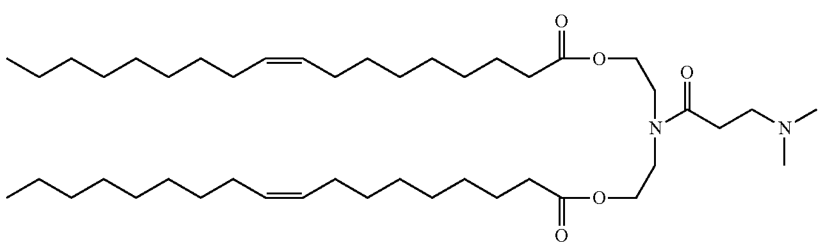 [SMILES: CCCCCCCC/C=C\CCCCCCCC(=O)OCCN(CCOC(=O)CCCCCCC/C=C\CCCCCCCC)C(=O)CCN(C)C] | 43% @ 50 nM | |
| i-Prop-DC | 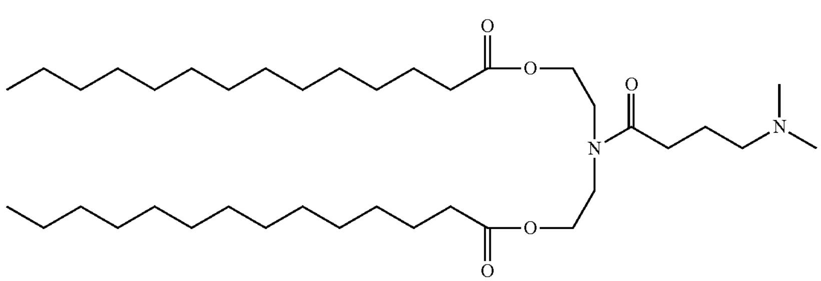 [SMILES: CCCCCCCCCCCCCC(=O)OCCN(CCOC(=O)CCCCCCCCCCCCC)C(=O)CCCN(C)C] | 55% @ 50 nM | |
| i-Prop-DODC | 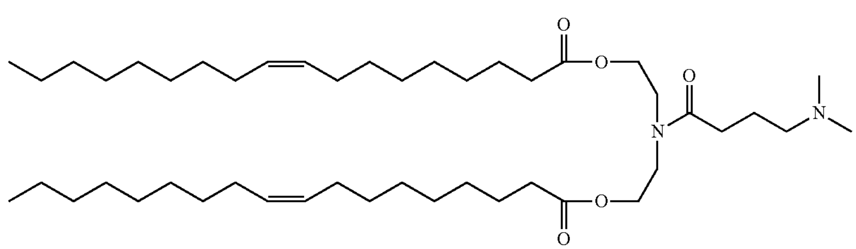 [SMILES: CCCCCCCC/C=C\CCCCCCCC(=O)OCCN(CCOC(=O)CCCCCCC/C=C\CCCCCCCC)C(=O)CCCN(C)C] | 55% @ 50 nM | |

TABLE 1-continued

| Lipid | Structure | in vitro (pHSC) % KD | in vivo (rat DMNQ) % KD |
|---|---|---|---|
| S104 | 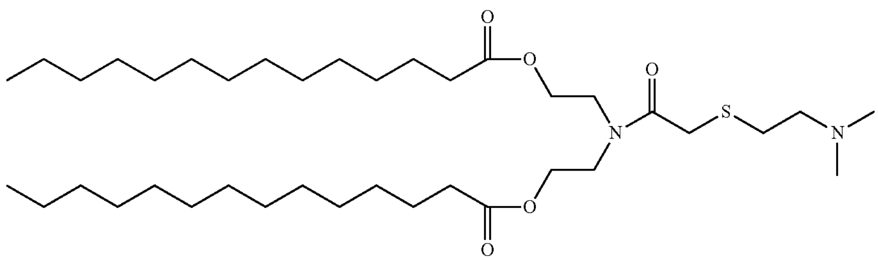 [SMILES: CCCCCCCCCCCCCC(=O)OCCN(CCOC(=O)CCCCCCCCCCCCC)C(=O)CSCCN(C)C] | 68% @ 50 nM | 52% @ 0.5 mpk |
| S104-DO | 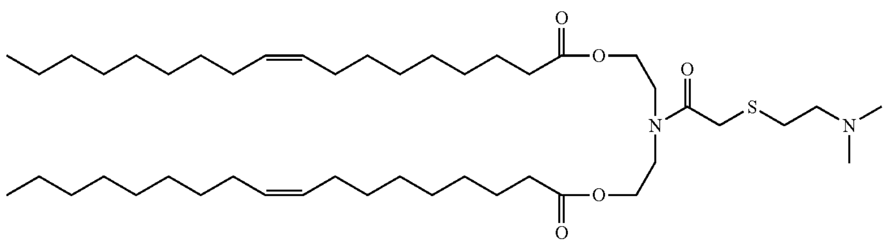 | 78% @ 20 nM | 65% @ 0.5 mpk |
| C104 | 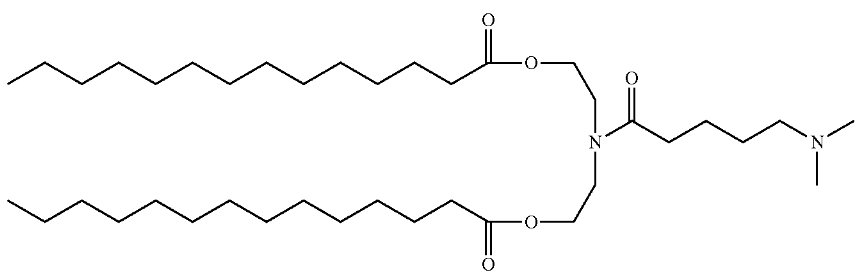 [SMILES: CCCCCCCCCCCCCC(=O)OCCN(CCOC(=O)CCCCCCCCCCCCC)C(=O)CCCCN(C)C] | 53% @ 20 nM | 75% @ 0.5 mpk |
| SO2-S104 | 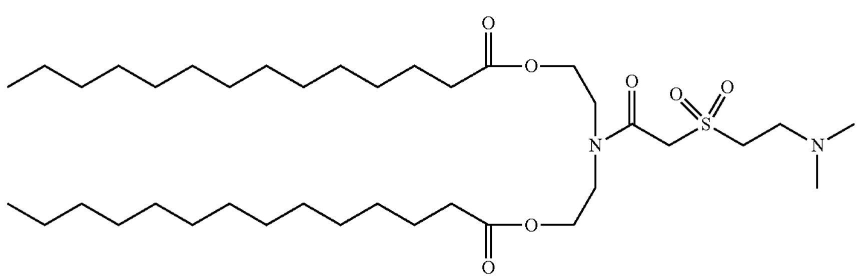 [SMILES: CCCCCCCCCCCCCC(=O)OCCN(CCOC(=O)CCCCCCCCCCCCC)C(=O)CS(=O)(=O)CCN(C)C] | 75% @ 20 nM | 18% @ 0.5 mpk |
| TU104 | 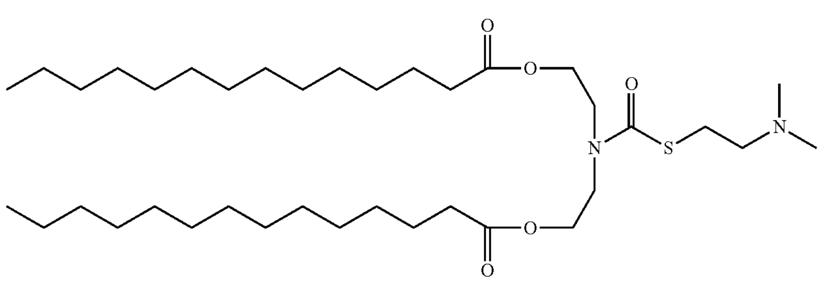 [SMILES: CCCCCCCCCCCCCC(=O)OCCN(CCOC(=O)CCCCCCCCCCCCC)C(=O)SCCN(C)C] | 76% @ 20 nM | |

TABLE 1-continued

| Lipid | Structure | in vitro (pHSC) % KD | in vivo (rat DMNQ) % KD |
|---|---|---|---|
| O104 | 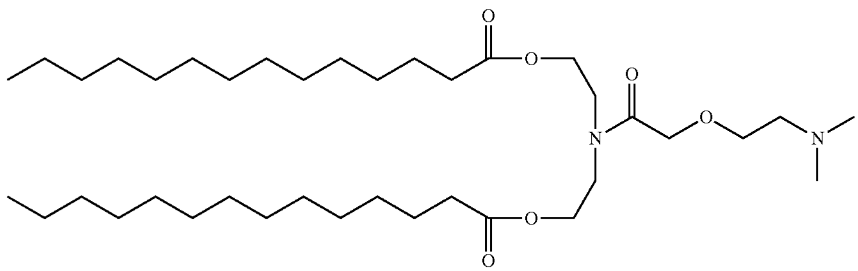 [SMILES: CCCCCCCCCCCCCC(=O)OCCN(CCOC(=O)CCCCCCCCCCCCC)C(=O)COCCN(C)C] | 55% @ 20 nM | |
| HEDC-M1 | 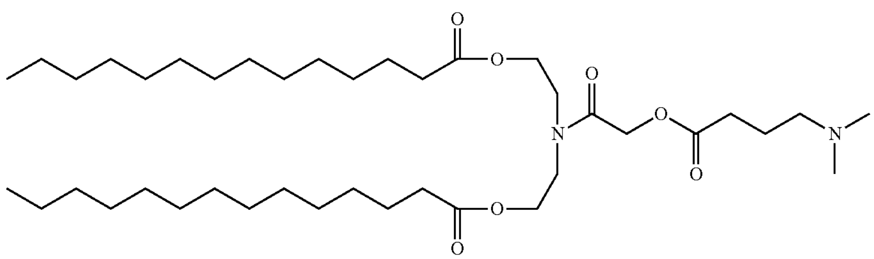 [SMILES: CCCCCCCCCCCCCC(=O)OCCN(CCOC(=O)CCCCCCCCCCCCC)C(=O)COC(=O)CCCN(C)C] | 53% @ 20 nM | |
| C104-DO | 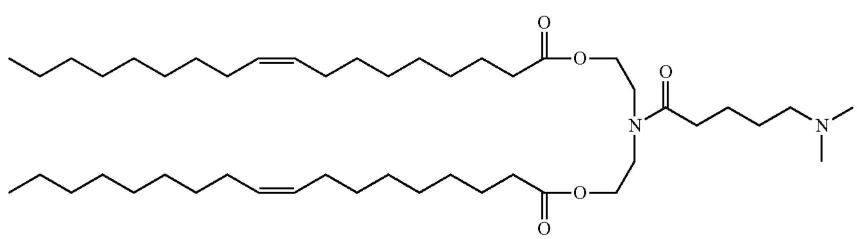 | 32% @ 20 nM | |
| Pr104 | 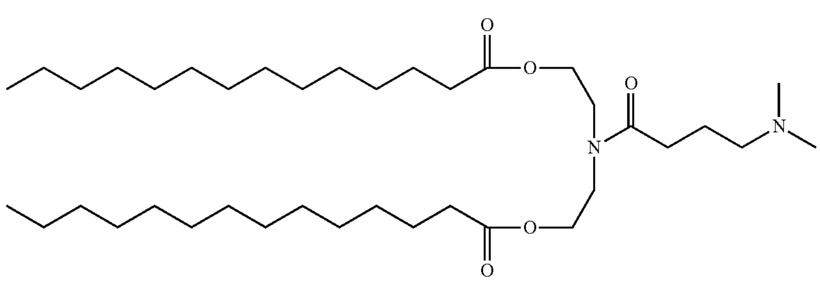 | 54% @ 20 nM | |
| Pr104-DO | 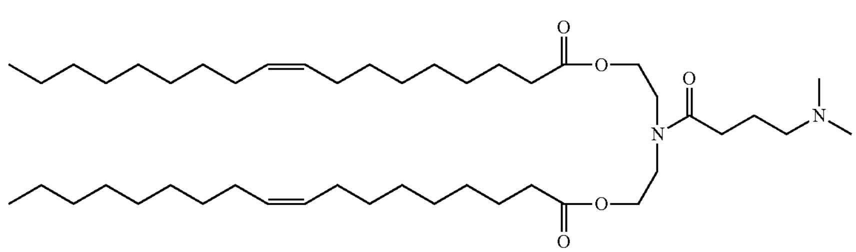 [SMILES: CCCCCCCC/C=C\CCCCCCCC(=O)OCCN(CCOC(=O)CCCCCCC/C=C\CCCCCCCC)C(=O)CCCN(C)C] | 27% @ 20 nM | |

TABLE 1-continued

| Lipid | Structure | in vitro (pHSC) % KD | in vivo (rat DMNQ) % KD |
|---|---|---|---|
| T104 | 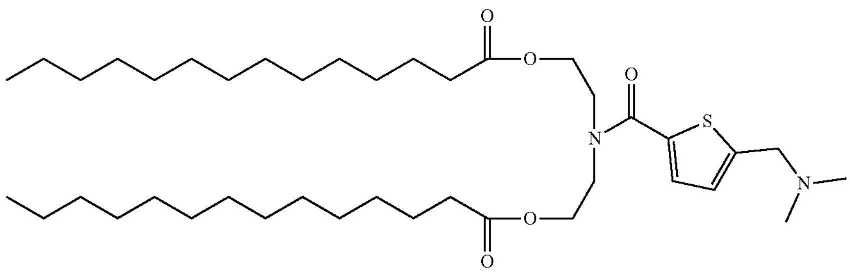 [SMILES: CCCCCCCCCCCCCC(=O)OCCN(CCOC(=O)CCCCCCCCCCCCC)C(=O)c1ccc(CN(C)C)s1] | 58% @ 20 nM | |
| TU104-DO | 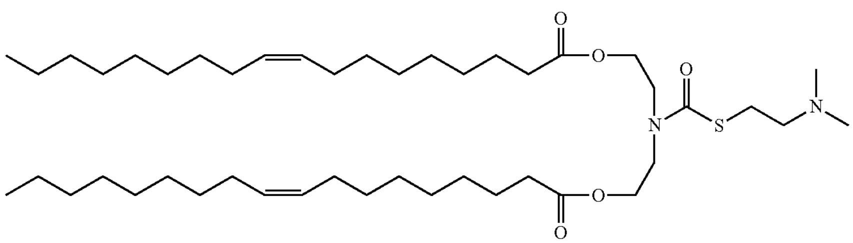 | 81% @ 20 nM | 40% @ 0.25 mpk |
| CB104 | 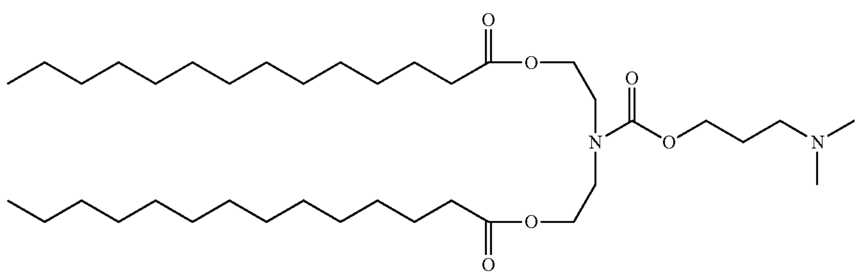 [SMILES: CCCCCCCCCCCCCC(=O)OCCN(CCOC(=O)CCCCCCCCCCCCC)C(=O)OCCCN(C)C] | 42% @ 20 nM | |
| CA104 | 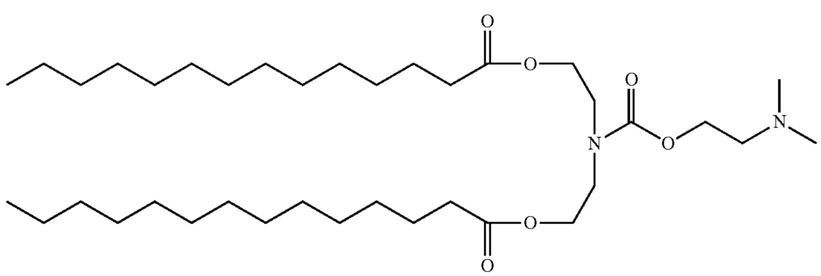 | | |
| INT-4 | 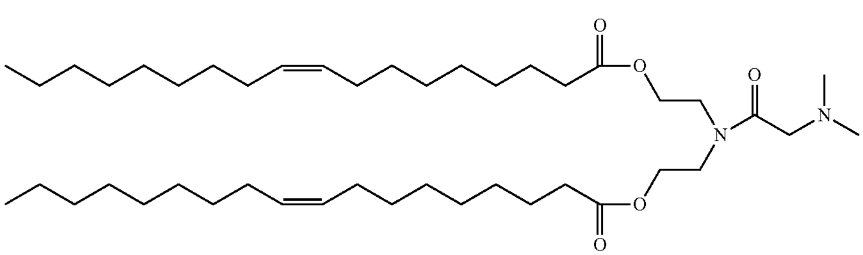 [SMILES: CCCCCCCC/C=C\CCCCCCCC(=O)OCCN(CCOC(=O)CCCCCCC/C=C\CCCCCCCC)C(=O)CN(C)C] | 70% @ 50 nM | |
| S104-DMO | 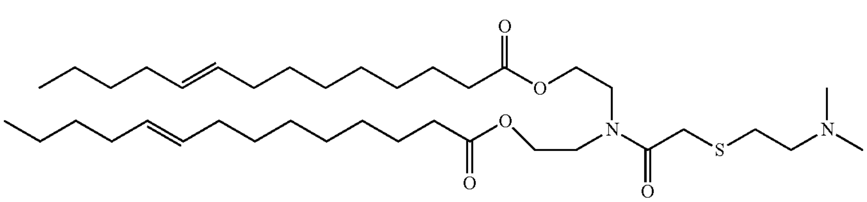 [SMILES: CCCC/C=C/CCCCCCCC(=O)OCCN(CCOC(=O)CCCCCCC/C=C/CCCC)C(=O)CSCCN(C)C] | 40% @ 10 nM | |

TABLE 1-continued

| Lipid | Structure | in vitro (pHSC) % KD | in vivo (rat DMNQ) % KD |
|---|---|---|---|
| Pro-DC | 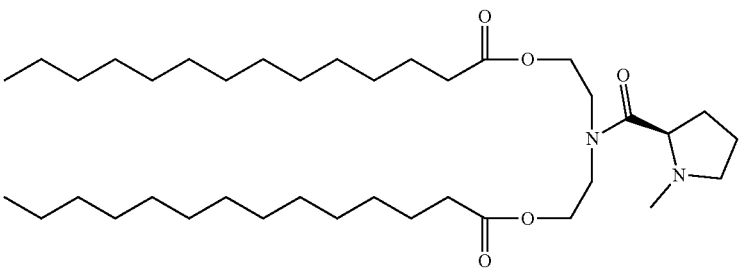 [SMILES: CCCCCCCCCCCCCC(=O)OCCN(CCOC(=O)CCCCCCCCCCCCC)C(=O)[C@H]1CCCN1C] | | |
| S104-DLin | 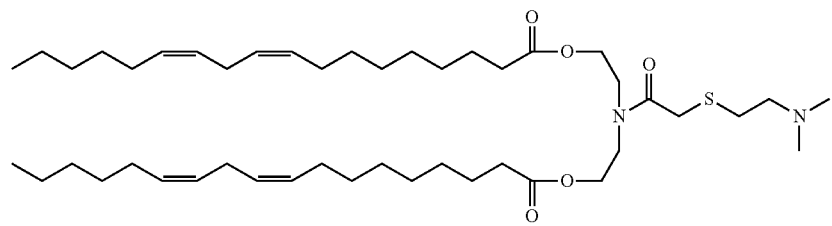 [SMILES: CCCCC/C=C\C/C=C\CCCCCCCC(=O)OCCN(CCOC(=O)CCCCCCC/C=C\C/C=C\CCCCC)C(=O)CSCCN(C)C] | | |
| TU104-DLin | 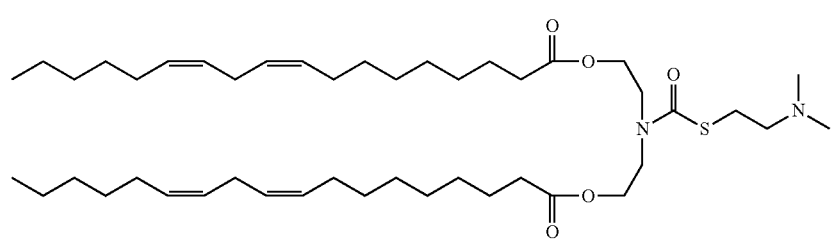 [SMILES: CCCCC/C=C\C/C=C\CCCCCCCC(=O)OCCN(CCOC(=O)CCCCCCC/C=C\C/C=C\CCCCC)C(=O)SCCN(C)C] | | |

The description can be further exemplified by reference to the following examples. These examples are illustrative, only, and are not intended to limit the description.

EXPERIMENTAL SECTION

Preparation of ((2-(dimethylamino)acetyl)azanediyl)bis(propane-3,1-diyl) ditetradecanoate (i-Pr-DC)

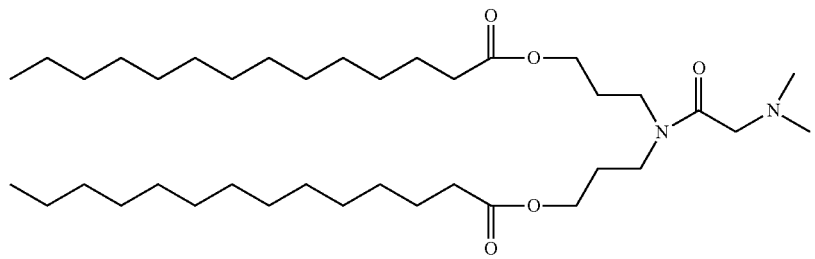 [SMILES: CCCCCCCCCCCCCC(=O)OCCCN(CCCOC(=O)CCCCCCCCCCCCC)C(=O)CN(C)C]

Step 1: Preparation of Intermediate 1: 3,3'-azanediylbis(propan-1-ol)

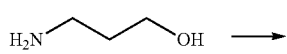 →

-continued

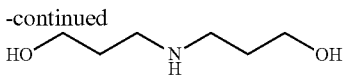

A mixture of 3-amino-1-propanol (14.5 mL, 19.0 mmol), 1-chloro-3-hydroxy propane (8.00 mL, 95.6 mmol) and H$_2$O (~50 mL) was refluxed over 24 hours. Potassium hydroxide (5.40 g) was then added. After dissolution, the whole of the water was evaporated to leave viscous oil and large quantities of potassium chloride. These were filtered and washed with dry acetone and dichloromethane. The organic phase was dried over Na$_2$SO$_4$, filtered and evaporated to leave an oil. Purification by silica gel chromatography eluting with a DCM/MeOH gradient yielded 3,3'-azanediylbis(propan-1-ol) (12.5 g).

Step 2: Preparation of Intermediate 2: tert-butyl bis(3-hydroxypropyl)carbamate

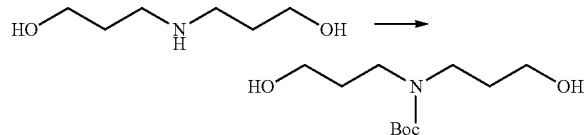

3,3'-azanediylbis(propan-1-ol) (12.5 g, 95.4 mmol) was diluted in DCM (25 mL). A solution of di-tert-butyl dicarbonate (26.0 g, 119 mmol) in DCM (25 mL) was slowly added while stirring under a blanket of argon gas. Reaction was allowed to stir overnight. The reaction mixture was concentrated. Purification by silica gel chromatography eluting with a DCM/MeOH gradient yielded tert-butyl bis(3-hydroxypropyl)carbamate.

Step 3: Preparation of Intermediate 3: ((tert-butoxycarbonyl)azanediyl)bis(propane-3,1-diyl) ditetradecanoate

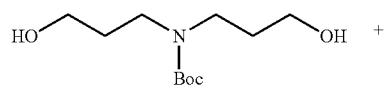

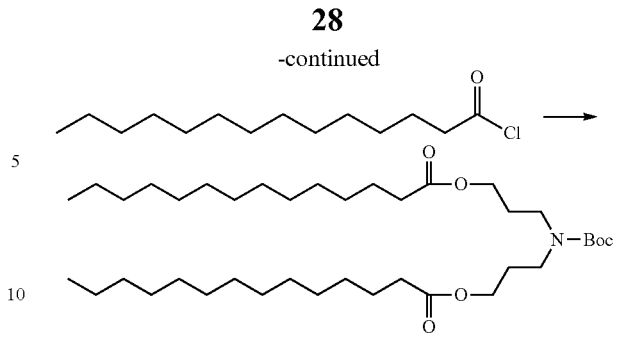

tert-butyl bis(3-hydroxypropyl)carbamate (4.00 g, 17.3 mmol), Et3N (4.8 mL, 34.6 mmol) and DMAP (529 mg, 4.33 mmol) were dissolved in chloroform (50 mL). While being stirred in an ice-bath, a solution of myristoyl chloride was added over 15 min. The addition was carried out in such a way that the temperature of the reaction did not exceed 30° C. The reaction was allowed to stir at room temperature overnight. Next day, MeOH (50 mL) and 0.9% saline solution (50 mL) was added to quench the reaction. The organic layer was separated and washed with 1M NaHCO₃. Solvent was dried with Na₂SO₄, filtered and concentrated in vacuo to yield ((tert-butoxycarbonyl)azanediyl)bis(propane-3,1-diyl)ditetradecanoate as an oil that was carried forward without further purification.

Step 4: Preparation of Intermediate 4: azanediylbis(propane-3,1-diyl)ditetradecanoate TFA salt

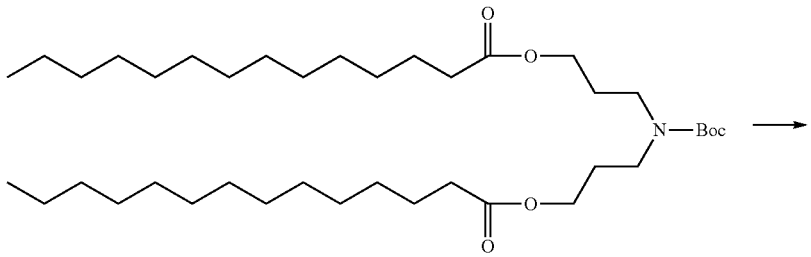

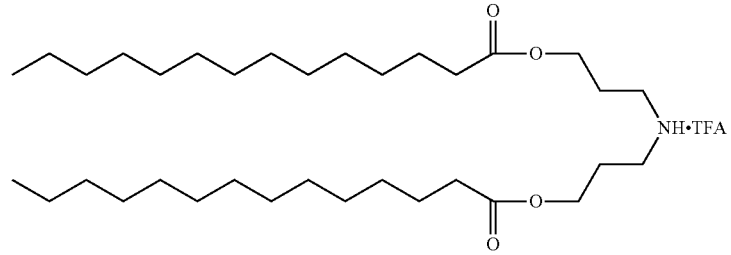

((tert-butoxycarbonyl)azanediyl)bis(propane-3,1-diyl) ditetradecanoate (11.3 g, 17.3 mmol) was dissolved in TFA/CHCl₃ (1:1, 20 mL) and the mixture was allowed to stir at room temperature for 15 minutes. Material was then concentrated in vacuo. This was repeated a second time. Material was then dissolved in DCM and washed with H₂O, dried with Na₂SO₄, concentrated in vacuo and dried fully overnight. The reaction mixture was concentrated. Purification by silica gel chromatography eluting with a DCM/MeOH gradient yielded azanediylbis(propane-3,1-diyl) ditetradecanoate TFA salt (7.5 g).

Step 5: Preparation of i-Pr-DC: ((2-(dimethylamino)acetyl)azanediyl)bis(propane-3,1-diyl)ditetradecanoate

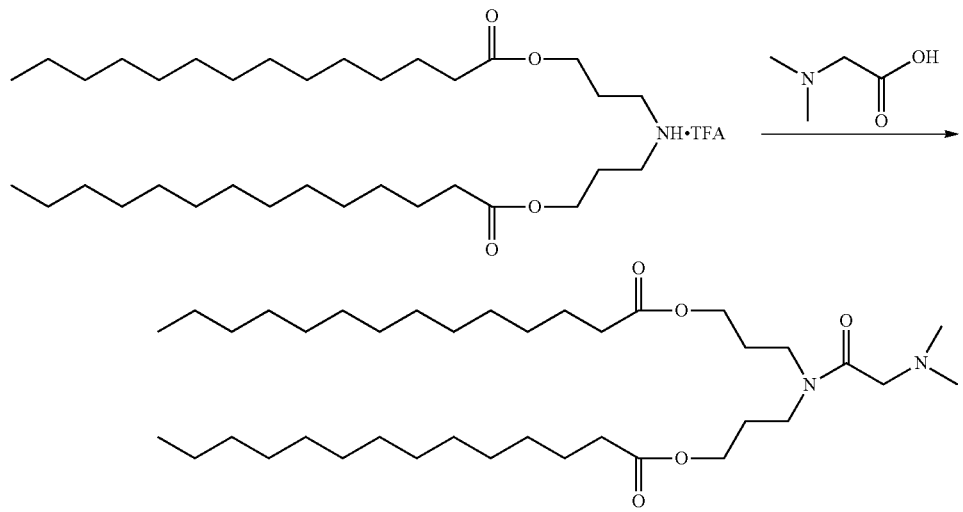

Azanediylbis(propane-3,1-diyl) ditetradecanoate TFA salt (750 mg, 1.35 mmol) was diluted with DCM (5 mL) and added to a pre-activated mixture of N,N-dimethylglycine (154 mg, 1.49 mmol), HATU (616 mg, 1.62 mmol) and DIEA (495 µL, 2.84 mmol) in DCM (5 mL). Flask was flushed with argon and allowed to stir at room temperature overnight. The reaction mixture was concentrated. Purification by silica gel chromatography eluting with a DCM/MeOH gradient yielded ((2-(dimethylamino)acetyl)azanediyl)bis(propane-3,1-diyl)ditetradecanoate (465 mg). QTOF MS ESI+: m/z 639.6 (M+H).

Preparation of (Z)-((2-(dimethylamino)acetyl)azanediyl)bis(propane-3,1-diyl)dioleate
(i-Pr-DODC)

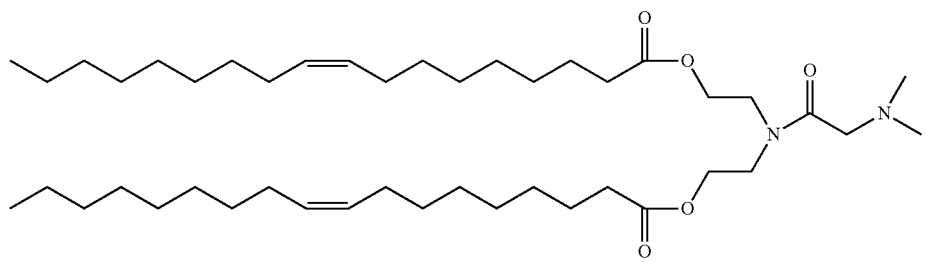 [SMILES: CCCCCCCC/C=C\CCCCCCCC(=O)OCCN(CCOC(=O)CCCCCCC/C=C\CCCCCCCC)C(=O)CN(C)C]

Step 1: Preparation of Intermediate 1: 3,3'-azanediylbis(propan-1-ol

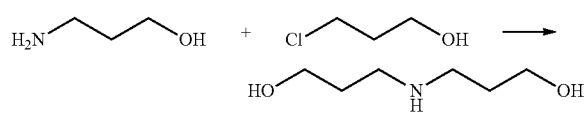

A mixture of 3-amino-1-propanol (14.5 mL, 19.0 mmol), 1-chloro-3-hydroxy propane (8.00 mL, 95.6 mmol) and water (50 mL) was refluxed over 24 hours. Potassium hydroxide (5.40 g) was then added. After dissolution, the whole of the water was evaporated to leave a viscous oil and large quantities of potassium chloride. These were filtered and washed with dry acetone and dichloromethane. The organic phase was dried over Na₂SO₄, filtered and evaporated to leave an oil. Purification by silica gel chromatography eluting with a DCM/MeOH gradient yielded 3,3'-azanediylbis(propan-1-ol) (12.5 g).

Step 2: Preparation of Intermediate 2: tert-butyl bis(3-hydroxypropyl)carbamate

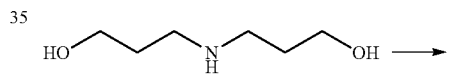

-continued

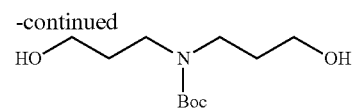

3,3'-azanediylbis(propan-1-ol) (12.5 g, 95.4 mmol) was diluted in DCM (25 mL). A solution of di-tert-butyl dicarbonate (26.0 g, 119 mmol) in DCM (25 mL) was slowly added while stirring under a blanket of argon gas. Reaction was allowed to stir overnight. The reaction mixture was concentrated. Purification by silica gel chromatography eluting with a DCM/MeOH gradient yielded tert-butyl bis(3-hydroxypropyl)carbamate.

Step 3: Preparation of Intermediate 3: (Z)-((tert-butoxycarbonyl)azanediyl)bis(propane-3,1-diyl) dioleate

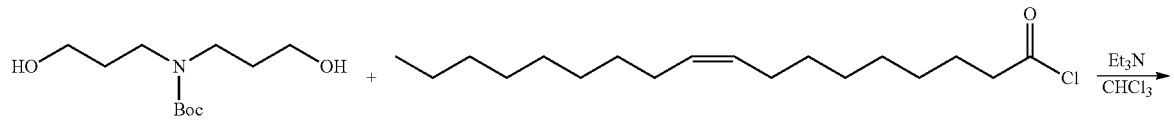

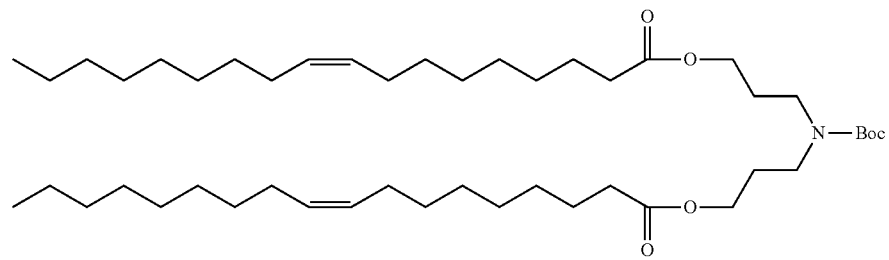

tert-butyl bis(3-hydroxypropyl)carbamate, triethylamine and DMAP were dissolved in chloroform. While being stirred in an ice-bath, a solution of oleyl chloride was added over 15 minutes. The addition was carried out in such a way that the temperature of the reaction did not exceed 30° C. The reaction was allowed to stir at room temperature overnight. Next day, MeOH (50 mL) and 0.9% saline solution (50 mL) was added to quench the reaction. The organic layer was separated and washed with 1M NaHCO₃. Solvent was dried with Na₂SO₄, filtered and concentrated in vacuo to yield (Z)-((tert-butoxycarbonyl)azanediyl)bis(propane-3,1-diyl)dioleate as an oil that was carried forward without further purification.

Step 4: Preparation of Intermediate 4: (Z)-azanediylbis(propane-3,1-diyl)dioleate TFA salt

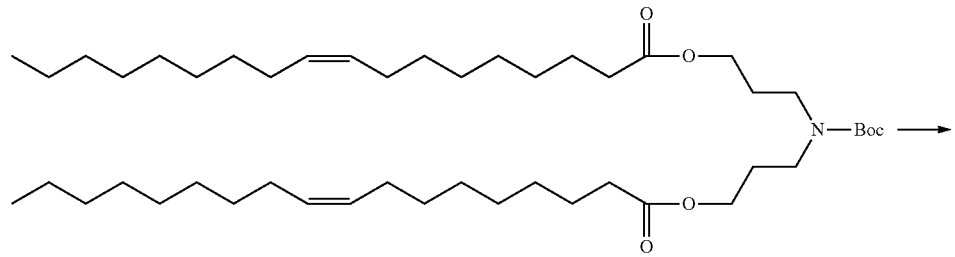

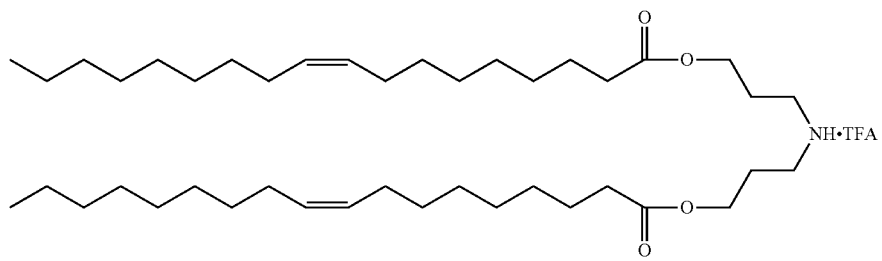

(Z)-((tert-butoxycarbonyl)azanediyl)bis(propane-3,1-diyl) dioleate (13.2 g, 17.3 mmol) was dissolved in TFA/CHCl₃ (1:1, 20 mL) and the mixture was allowed to stir at room temperature for 15 minutes. Material was then concentrated in vacuo. This was repeated a second time. Material was then dissolved in DCM and washed with H₂O, dried with Na₂SO₄ and concentrated in vacuo. Purification by silica gel chromatography eluting with a DCM/MeOH gradient yielded (Z)-azanediylbis(propane-3,1-diyl)dioleate TFA salt.

Step 5: Preparation of i-Pr-DODC: (Z)-((2-(dimethylamino)acetyl)azanediyl)bis(propane-3,1-diyl)dioleate

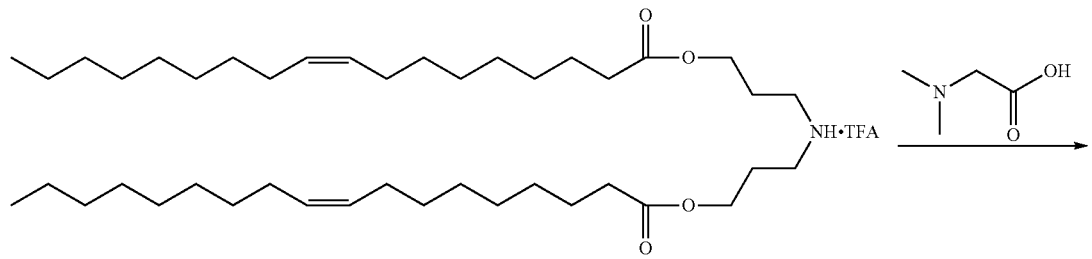

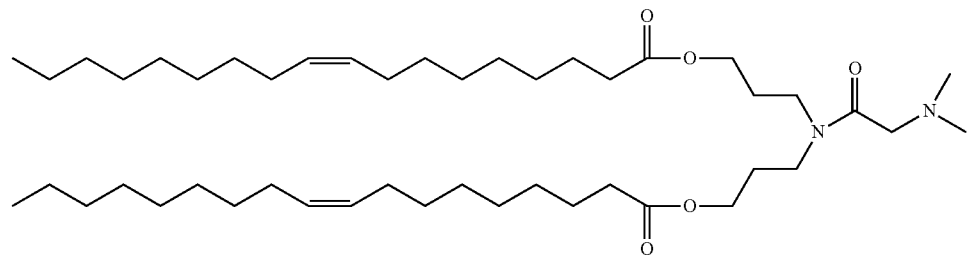

(Z)-azanediylbis(propane-3,1-diyl)dioleate TFA salt (750 mg, 1.13 mmol) was diluted with DCM (5 mL) and added to a pre-activated mixture of N,N-dimethylglycine (128 mg, 1.24 mmol), HATU (517 mg, 1.36 mmol) and DIEA (413 µL, 2.37 mmol) in DCM (5 mL). Flask was flushed with argon and allowed to stir at room temperature overnight. The reaction mixture was concentrated. Purification by silica gel chromatography eluting with a DCM/MeOH gradient yielded (Z)-((2-(dimethylamino)acetyl)azanediyl)bis(propane-3,1-diyl)dioleate (450 mg). QTOF MS ESI+: m/z 747.7 (M+H).

Preparation of ((2-(dimethylamino)acetyl)azanediyl)bis(ethane-2,1-diyl) ditetradecanoate, (i-DC)

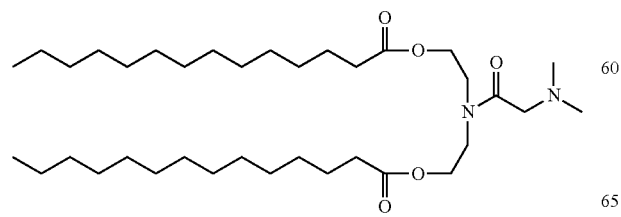

Step 1: Preparation of Intermediate 1: ((tert-butoxycarbonyl)azanediyl)bis(ethane-2,1-diyl) ditetradecanoate

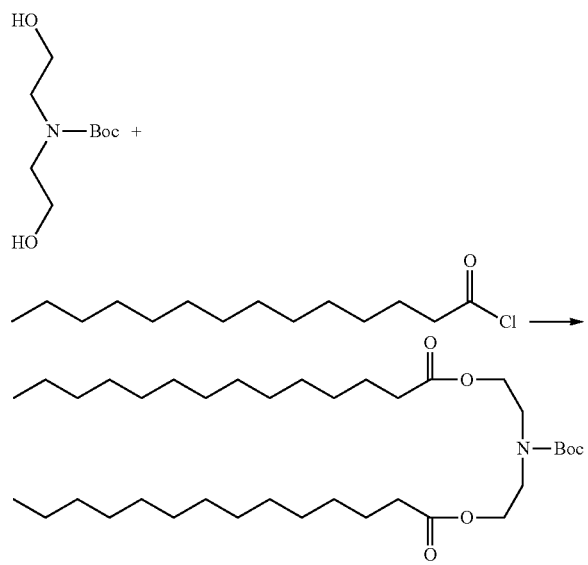

N-Boc diethanolamine (MW 205.25; 8.4 g, 0.041 mole), triethylamine (MW 101.19; 11.5 ml, 0.083 mol) and 4-(dimethylamino)pyridine (MW 122.17; 1.3 g, 0.011 mole) were dissolved in chloroform (170 mL). While being stirred in an ice/water bath, a solution of myristoyl chloride (MW 246.82; 22 mL, 80.9 mmol) in 100 mL of chloroform was added dropwise. The reaction mixture was then taken out of the cold bath, and the stirring was continued at room temperature for 2 h. A mixture of 200 mL of methanol and 200 ml of 0.9% saline was added to quench the reaction. The stirring was stopped and the organic layer was isolated. The solvent was removed by rotary evaporation to afford ((tert-butoxycarbonyl)azanediyl)bis(ethane-2,1-diyl)ditetradecanoate as a colorless oil (25.7 g) that was carried forward without further purification.

Step 2: Preparation of Intermediate 2: azanediylbis(ethane-2,1-diyl)ditetradecanoate TFA salt

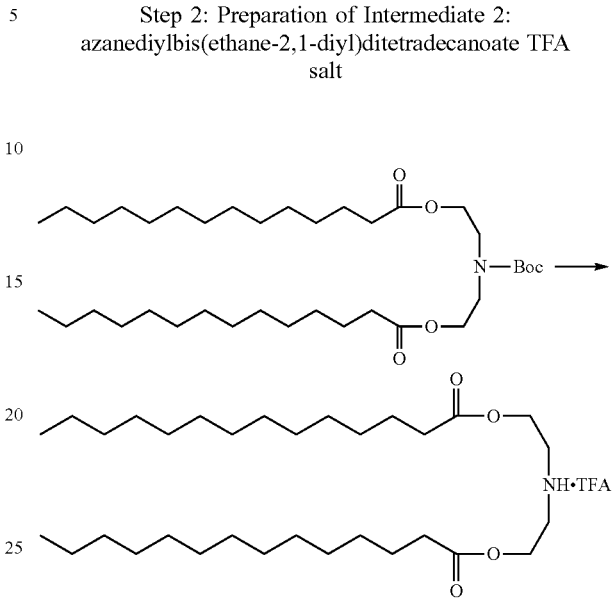

To a solution of ((tert-butoxycarbonyl)azanediyl)bis(ethane-2,1-diyl)ditetradecanoate (33.0 g, 0.053 mole) in 100 ml of chloroform was added trifluoroacetic acid (150 mL, 2.02 mol). The reaction mixture was stirred at room temperature overnight. After the solvent was removed by rotary evaporation, the resultant soft solid was recrystallized from 80 ml of methanol to yield azanediylbis(ethane-2,1-diyl)ditetradecanoate TFA salt (16.6 g) as a white solid.

Step 3: Preparation of i-DC: ((2-(dimethylamino)acetyl)azanediyl)bis(ethane-2,1-diyl)ditetradecanoate

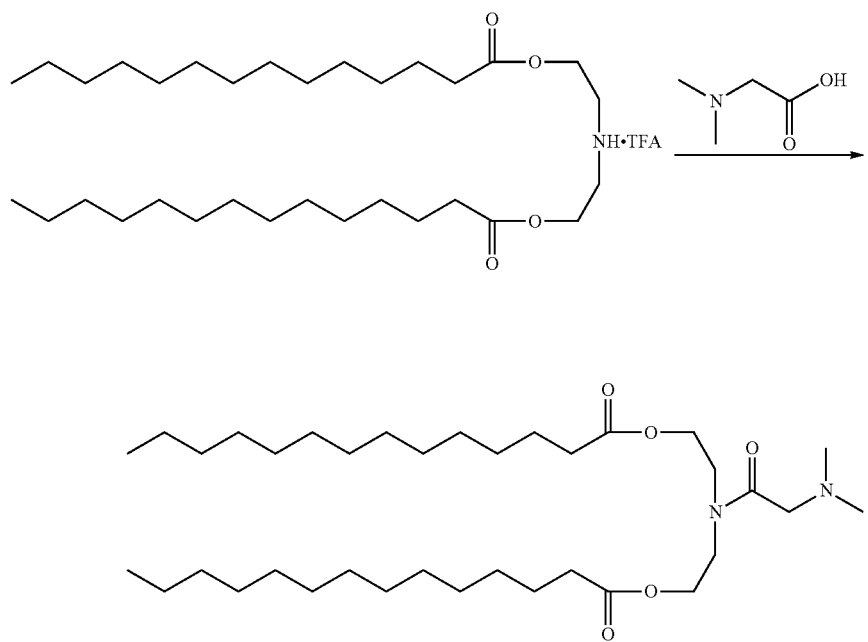

Azanediylbis(ethane-2,1-diyl)ditetradecanoate TFA salt (10 g, 16 mmol) was diluted with dimethylglycine (42.5 g, 25 mmol), DCC (4.7 g, 23 mmol) and DIEA (6.33 mL, 40 mmol) in Pyridine (20 mL). The round-bottomed flask was flushed with argon gas and the reaction mixture was heated at 55° C. overnight. Next day, the reaction mixture was concentrated. After purification by silica gel chromatography eluting with a DCM/MeOH, the pooled fractions were concentrated to yield ((2-(dimethylamino)acetyl)azanediyl)bis(ethane-2,1-diyl) ditetradecanoate.

Preparation of ((3-(dimethylamino)propanoyl)azanediyl)bis(ethane-2,1-diyl) ditetradecanoate (i-Et-DC, also referred to herein as Et104)

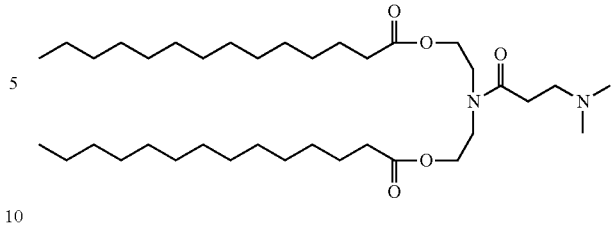

Preparation of i-Et-DC: ((3-(dimethylamino)propanoyl)azanediyl)bis(ethane-2,1-diyl)ditetradecanoate

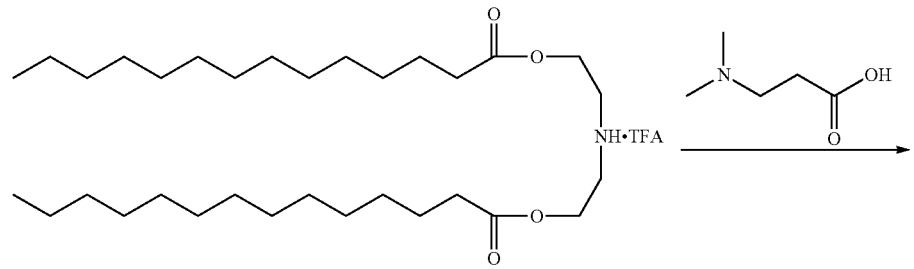

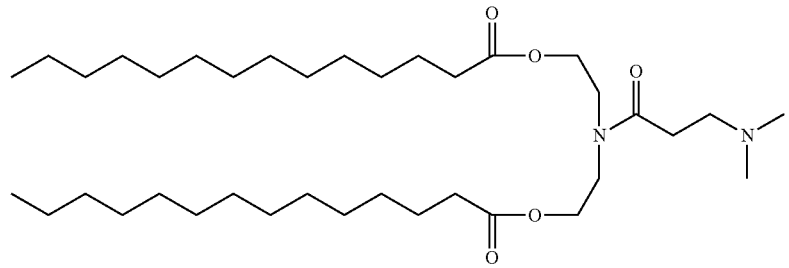 [SMILES: CCCCCCCCCCCCCC(=O)OCCN(CCOC(=O)CCCCCCCCCCCCC)C(=O)CCN(C)C]

Synthesis of azanediylbis(ethane-2,1-diyl) ditetradecanoate TFA salt previously described. Azanediylbis(ethane-2,1-diyl) ditetradecanoate TFA salt (1.50 g, 2.85 mmol) was diluted with DCM (10 mL) and added to a pre-activated mixture of 3-(dimethylamino)propionic acid HCl salt (482 mg, 3.14 mmol), HATU (1.30 g, 3.42 mmol) and DIEA (1.04 mL, 5.98 mmol) in DCM (10 mL). The round-bottomed flask was flushed with argon gas and the reaction mixture was allowed to stir at room temperature overnight. The reaction mixture was concentrated. After purification by silica gel chromatography eluting with a DCM/MeOH, the pooled fractions were concentrated and stirred in DCM (20 mL) and 10% $K_2CO_3$ (20 mL) at 0-5° C. for 30 min. The organic layer was isolated and the aqueous layer further extracted with DCM (2×10 mL). The combined organics were stirred with $MgSO_4$ for 30 min at 0-5° C., filtered, washed with DCM, and concentrated to yield ((3-(dimethylamino)propanoyl)azanediyl)bis(ethane-2,1-diyl)ditetradecanoate (1.01 g). QTOF MS ESI+: m/z 625.6 (M+H).

Preparation of (Z)-((3-(dimethylamino)propanoyl)azanediyl)bis(ethane-2,1-diyl)dioleate (i-Et-DODC)

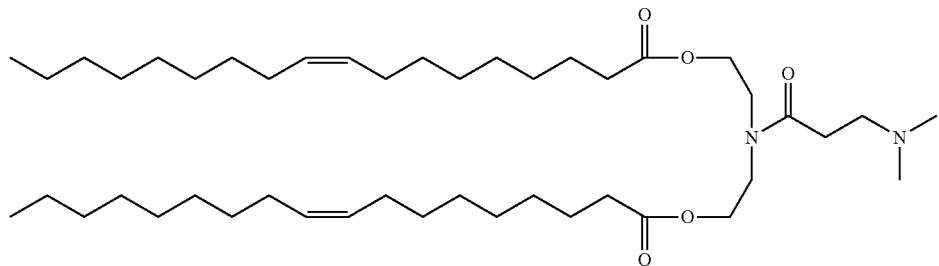 [SMILES: CCCCCCCC/C=C\CCCCCCCC(=O)OCCN(CCOC(=O)CCCCCCC/C=C\CCCCCCCC)C(=O)CCN(C)C]

Step 1: Preparation of Intermediate 1: (Z)-((tert-butoxycarbonyl)azanediyl)bis(ethane-2,1-diyl)dioleate

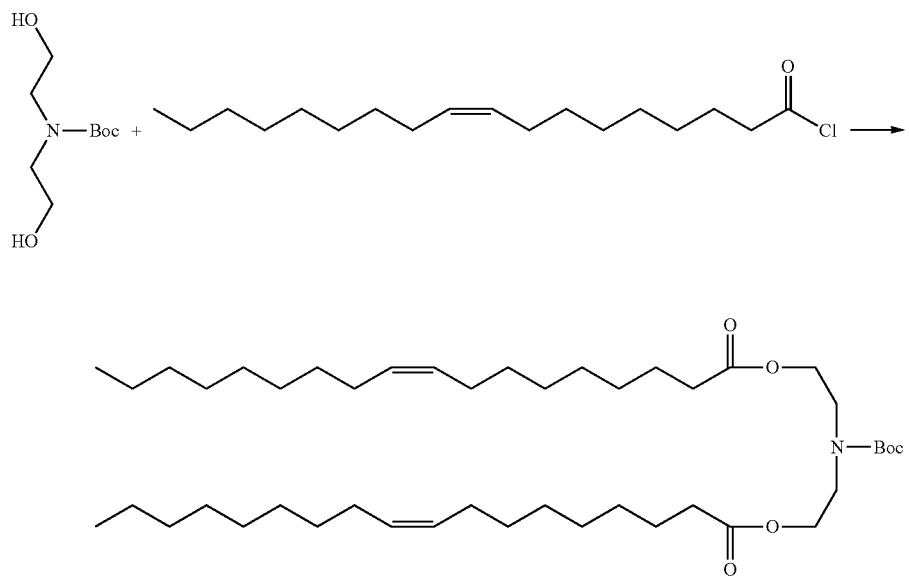

N-Boc diethanolamine (17.8 g, 0.087 mole), triethylamine (24.4 mL, 0.176 mole) and 4-(dimethylamino)pyridine (2.76 g, 0.023 mole) were dissolved in 350 ml of chloroform. While being stirred, a solution of oleyl chloride (61.6 g, 0.174 mole) in 100 ml of chloroform was added over 10 min (Alternatively, the chloroform solution of N-Boc diethanolamine was immersed in an ice/water bath while oleyl chloride was added). The addition was carried out in such a way that the temperature of the reaction mixture does not exceed 50° C. The reaction mixture was stirred at room temperature for 2 hrs. A mixture of 200 ml of methanol and 200 ml of 0.9% saline was added to quench the reaction. The organic layer was separated and washed with 2×100 ml of dilute aqueous sodium bicarbonate. The solvent was removed by rotary evaporation to afford (Z)-((tert-butoxycarbonyl)azanediyl)bis(ethane-2,1-diyl) dioleate as a pale yellow oil (59.5 g). This material was used for the next step without further purification. 1H NMR (400 MHz, $CDCl_3$) 0.87 (t, 6H, $CH_3$), 1.20-1.40 (m, 40H, $CH_2$), 1.45 (s, 9H, tBu $CH_3$), 1.59 (m, 4H, $CH_2CH_2C(=O)$), 2.00 (m, 8H, $CH_2CH=CH$), 2.33 (t, 4H, $CH_2C(=O)$), 3.48 (m, 4H, $NCH_2CH_2O$), 4.18 (m, 4H, $NCH_2CH_2O$), 5.33 (m, 4H, $CH=CH$).

Step 2: Preparation of Intermediate 2: (Z)-azanediylbis(ethane-2,1-diyl) dioleate TFA salt

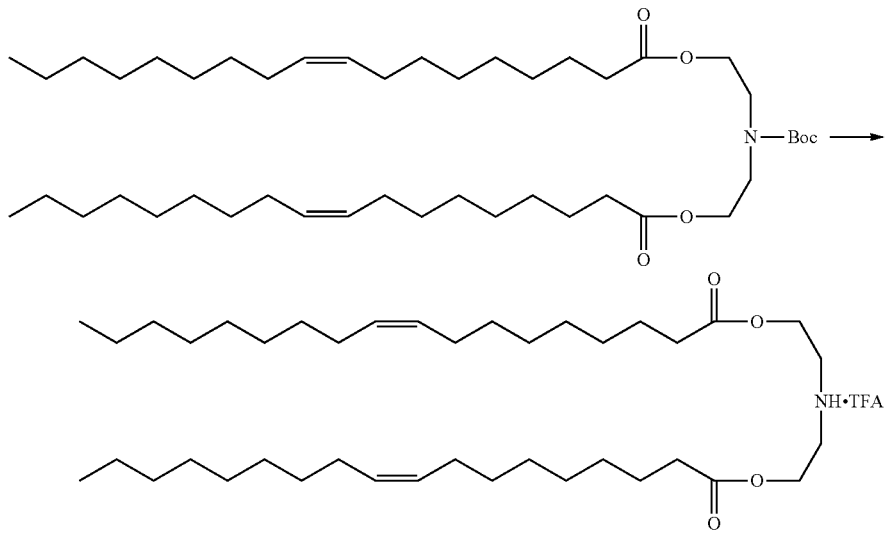

(Z)-((tert-butoxycarbonyl)azanediyl)bis(ethane-2,1-diyl) dioleate (59.5 g, 0.081 mole) was treated twice with 100 ml trifluoroacetic acid (100 mL, 1.35 mol) and 100 ml of chloroform. Each consisted of stirring at room temperature for 10 min, and the solvent was removed by rotary evaporation at the end of each treatment. The residue was dissolved in 200 ml of methylene chloride and the mixture had been washed with 100 ml of water twice. The residue was purified by the silica gel chromatography using a mixture of methanol and methylene chloride as eluent to yield (Z)-azanediylbis(ethane-2,1-diyl) dioleate TFA salt (44.0 g). 1H NMR (400 MHz, CDCl$_3$) 0.87 (t, 6H, CH$_3$), 1.20-1.40 (m, 40H, CH$_2$), 1.59 (m, 4H, CH$_2$CH$_2$C(=O)), 2.00 (m, 8H, CH$_2$CH=CH), 2.33 (t, 4H, CH$_2$C(=O)), 3.31 (m, 4H, NCH$_2$CH$_2$O), 4.38 (m, 4H, NCH$_2$CH$_2$O), 5.33 (m, 4H, CH=CH).

Step 3: Preparation of i-Et-DODC: (Z)-((3-(dimethylamino)propanoyl)azanediyl)bis(ethane-2,1-diyl)dioleate

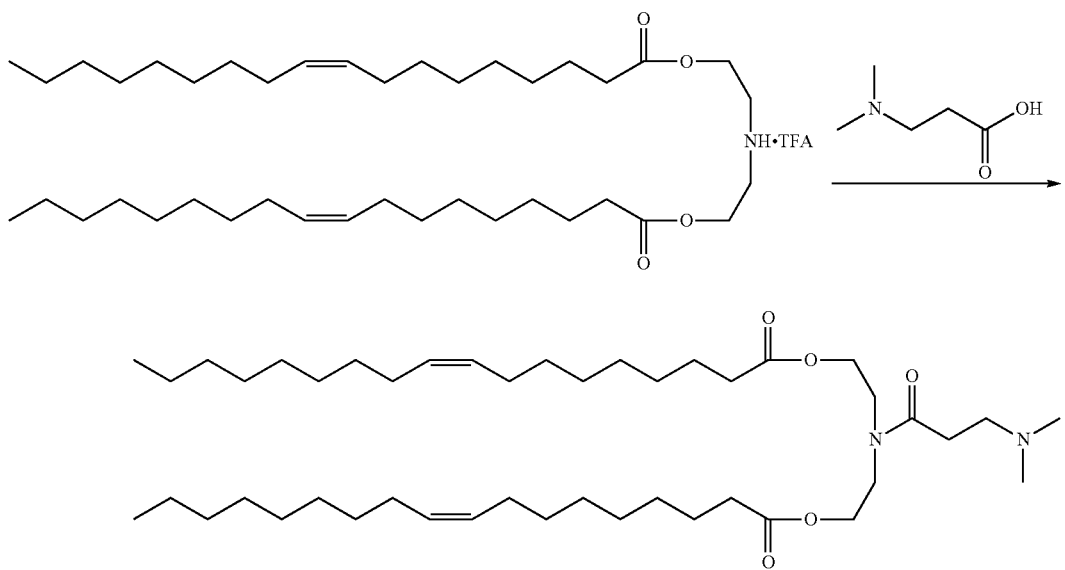

(Z)-azanediylbis(ethane-2,1-diyl)dioleate TFA salt (1.50 g, 2.37 mmol) was diluted with DCM (10 mL) and added to a pre-activated mixture of 3-(dimethylamino)propionic acid HCl salt (383 mg, 2.49 mmol), HATU (1.03 g, 2.72 mmol) and DIEA (831 µL, 4.77 mmol) in DCM (10 mL). The round-bottomed flask was flushed with argon gas and the reaction mixture was allowed to stir at room temperature overnight. The reaction mixture was concentrated. After purification by silica gel chromatography eluting with a DCM/MeOH, the pooled fractions were concentrated and stirred in DCM (20 mL) and 10% $K_2CO_3$ (20 mL) at 0-5° C. for 30 min. The organic layer was isolated and the aqueous layer further extracted with DCM (2×10 mL). The combined organics were stirred with $MgSO_4$ for 30 min at 0-5° C., filtered, washed with DCM, and concentrated to yield (Z)-((3-(dimethylamino)propanoyl)azanediyl)bis(ethane-2,1-diyl)dioleate. QTOF MS ESI+: m/z 733.6 (M+H).

Preparation of ((4-(dimethylamino)butanoyl)azanediyl) bis(ethane-2,1-diyl) ditetradecanoate [i-Prop-DC (also referred to herein as Pr104)]

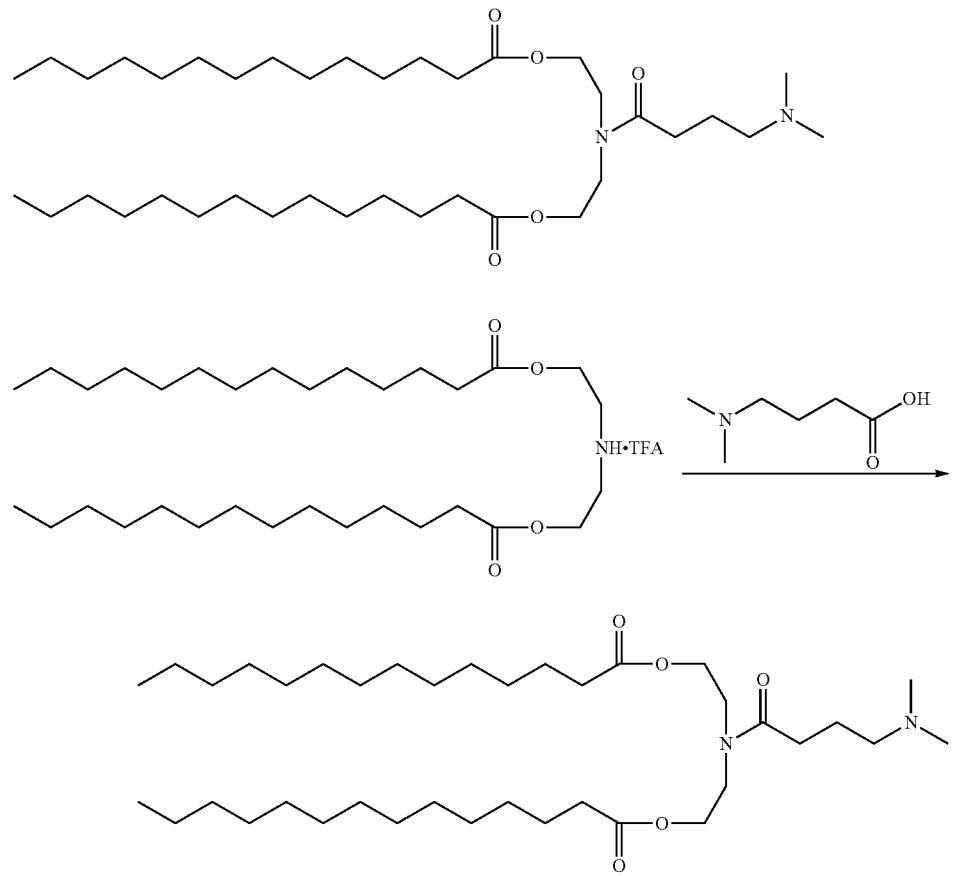

Synthesis of azanediylbis(ethane-2,1-diyl) ditetradecanoate TFA salt previously described. Azanediylbis(ethane-2,1-diyl)ditetradecanoate TFA salt (1.00 g, 1.90 mmol) was diluted with DCM (5 mL) and added to a pre-activated mixture of 4-(Dimethylamino) butyric acid HCl salt (382 mg, 2.28 mmol), HATU (867 mg, 2.28 mmol) and DIEA (728 µL, 4.18 mmol) in DCM (5 mL). The round-bottomed flask was flushed with argon gas and the reaction mixture was allowed to stir at room temperature overnight. The reaction mixture was concentrated. After purification by silica gel chromatography eluting with a DCM/MeOH, the pooled fractions were concentrated and stirred in DCM (20 mL) and 10% $K_2CO_3$ (20 mL) at 0-5° C. for 30 min. The organic layer was isolated and the aqueous layer further extracted with DCM (2×10 mL). The combined organics were stirred with $MgSO_4$ for 30 min at 0-5° C., filtered, washed with DCM, and concentrated to yield ((4-(dimethylamino)butanoyl)azanediyl)bis(ethane-2,1-diyl)ditetradecanoate. LCMS ESI+: m/z 639.6 (M+H).

Preparation of (Z)-((4-(dimethylamino)butanoyl)azanediyl)bis(ethane-2,1-diyl)dioleate (i-Prop-DODC (also referred to herein as Pr104-DO))

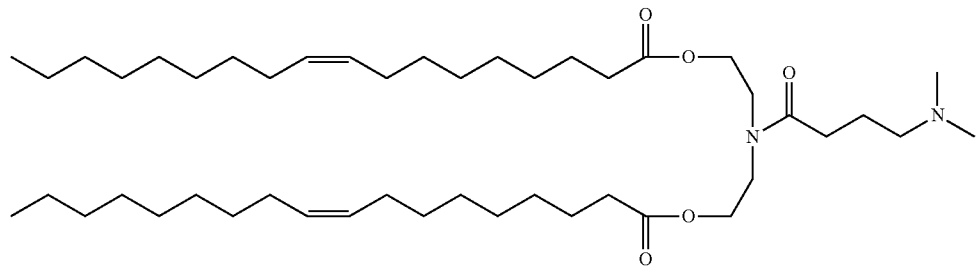

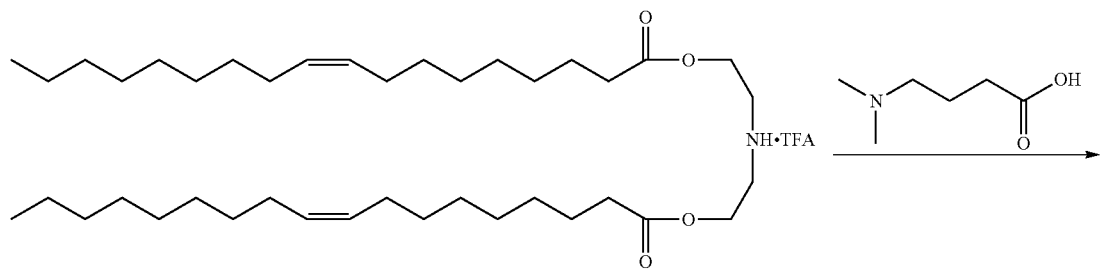

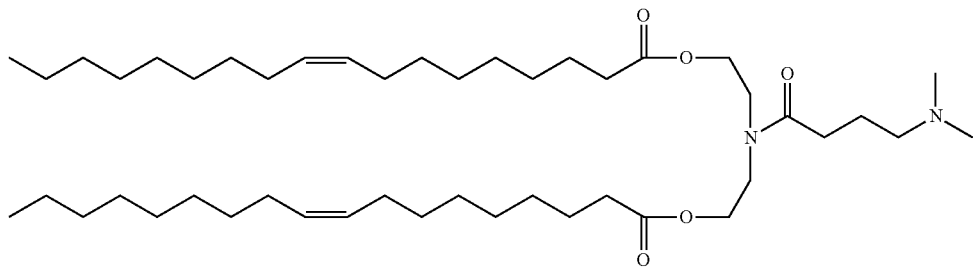

Synthesis of (Z)-azanediylbis(ethane-2,1-diyl)dioleate TFA salt previously described. (Z)-azanediylbis(ethane-2,1-diyl)dioleate TFA salt (1.00 g, 1.58 mmol) was diluted with DCM (5 mL) and added to a pre-activated mixture of 4-(dimethylamino)butyric acid HCl salt (317 mg, 1.89 mmol), HATU (719 mg, 1.89 mmol) and DIEA (606 µL, 3.48 mmol) in DCM (5 mL). The round-bottomed flask was flushed with argon gas and the reaction mixture was allowed to stir at room temperature overnight. The reaction mixture was concentrated. After purification by silica gel chromatography eluting with a DCM/MeOH, the pooled fractions were concentrated and stirred in DCM (20 mL) and 10% $K_2CO_3$ (20 mL) at 0-5° C. for 30 min. The organic layer was isolated and the aqueous layer further extracted with DCM (2×10 mL). The combined organics were stirred with $MgSO_4$ for 30 min at 0-5° C., filtered, washed with DCM, and concentrated to yield (Z)-((4-(dimethylamino)butanoyl)azanediyl)bis(ethane-2,1-diyl)dioleate. LCMS ESI+: m/z 747.7 (M+H).

Preparation of (Z)-((2-((2-(dimethylamino)ethyl)thio)acetyl)azanediyl)bis(ethane-2,1-diyl)dioleate (S104-DO)

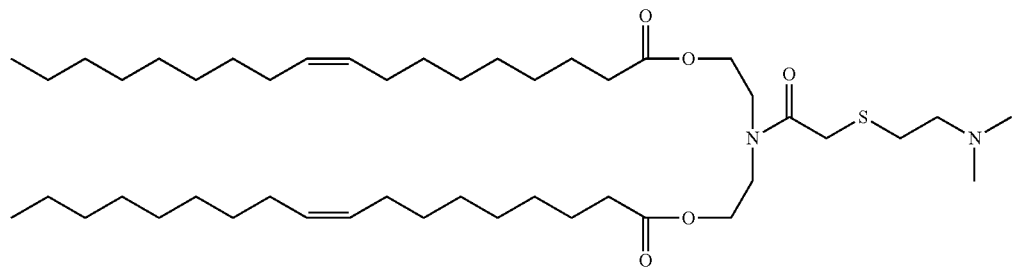

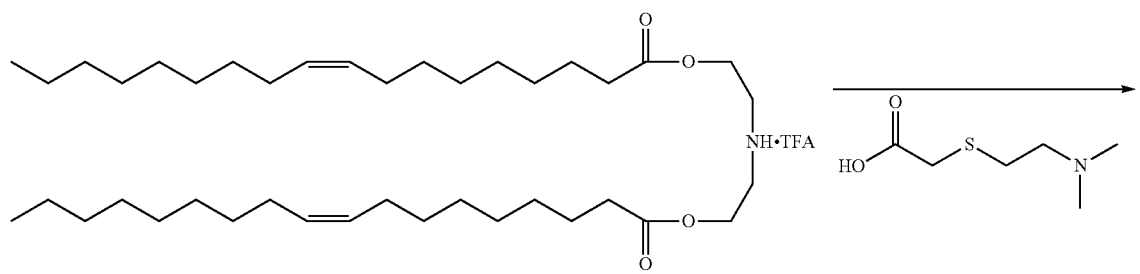

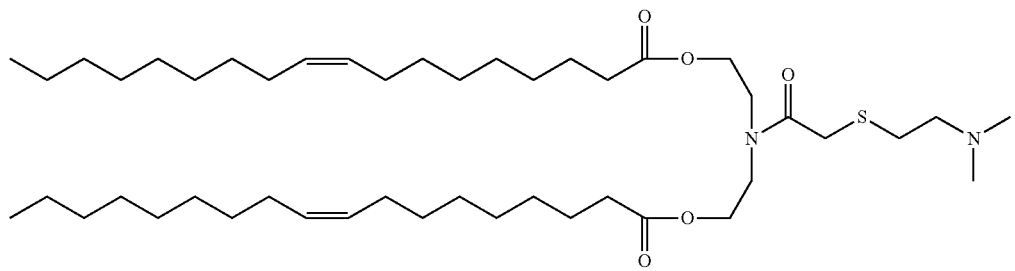

Synthesis of (Z)-azanediylbis(ethane-2,1-diyl)dioleate TFA salt previously described. (Z)-azanediylbis(ethane-2,1-diyl)dioleate TFA salt (4.06 g, 6.41 mmol) was stirred in DCM (60 mL) with 10% $K_2CO_3$ (30 mL) at 0-5° C. After 30 min, the organic phase is separated and the aqueous phase was further extracted with DCM (30 mL). The combined organic phases are stirred with $MgSO_4$ for a period of 30 min at 0-5° C., filtered and washed with DCM (~30 mL). To the combined filtrates were added 2-((2-(dimethylamino)ethyl)thio)acetic acid (1.26 g, 7.70 mmol), EDC HCl salt (1.84 g, 9.62 mmol), DMAP (78.3 mg, 0.64 mmol) and the thin suspension was stirred overnight at room temperature. Next day, $H_2O$ (60 mL) and MeOH (30 mL) are added and after stirring for 10 min, the clear organic phase was isolated. The turbid aqueous phase was extracted with DCM. The combined organic extracts are concentrated. Crude material was filtered through a plug of silica and taken up in DCM (40 mL) and PBS (pH=11, 50 mL) was added. The mixture was stirred at room temperature for ~10 min. Afterwards, the organic phase was separated and the aqueous phase was extracted again with DCM (15 mL). The combined organics are dried ($MgSO_4$) for 30 min, filtered, washed with DCM, and concentrated to yield (Z)-((2-((2-(dimethylamino)ethyl)thio)acetyl)azanediyl)bis(ethane-2,1-diyl)dioleate (3.44 g). LCMS ESI+: m/z 780.2 (M+H).

Preparation ((5-(dimethylamino)pentanoyl)azanediyl)bis(ethane-2,1-diyl)ditetradecanoate (C104)

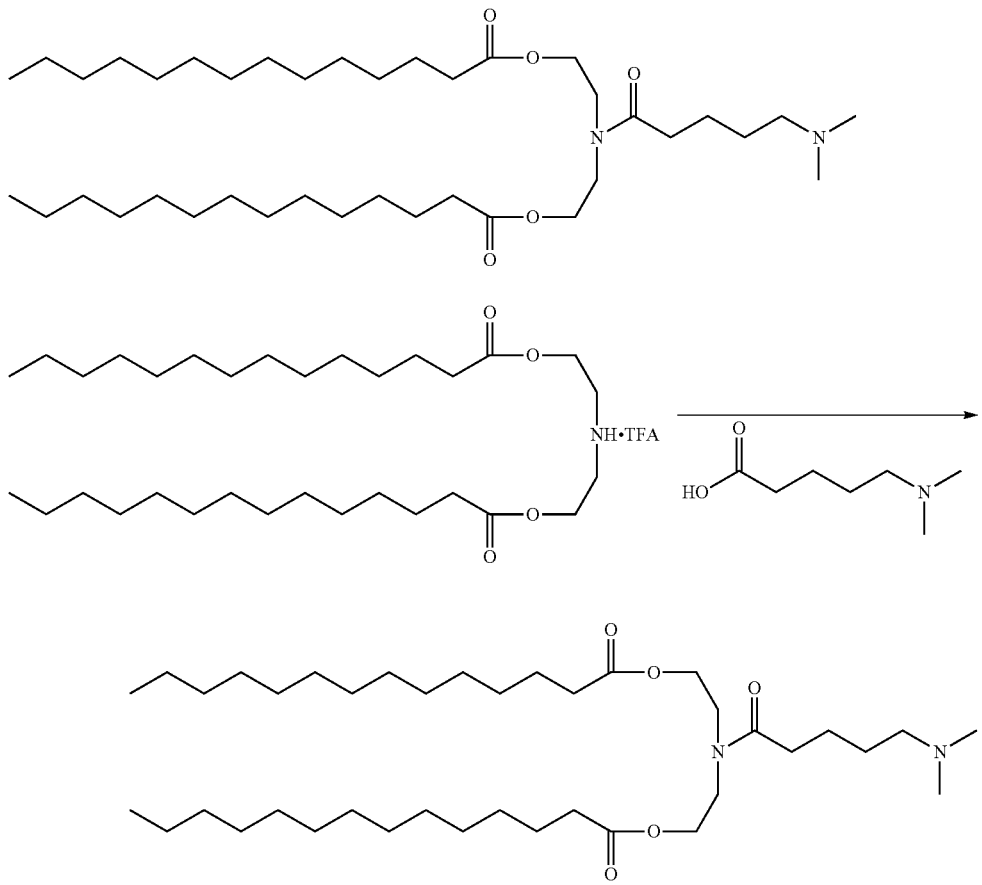

Synthesis of azanediylbis(ethane-2,1-diyl)ditetradecanoate TFA salt previously described. Azanediylbis(ethane-2,1-diyl)ditetradecanoate TFA salt (730 mg, 1.14 mmol) was stirred in DCM (20 mL) with 10% $K_2CO_3$ (10 mL) at 0-5° C. After 30 min, the organic phase was separated and the aqueous phase was further extracted with DCM (10 mL). The combined organic phases are stirred with $MgSO_4$ for a period of 30 minutes at 0-5° C., filtered and washed with DCM (10 mL). To the combined filtrates are added 5-(dimethylamino)pentanoic acid (248 mg, 1.37 mmol), EDC HCl salt (328 mg, 1.71 mmol), DMAP (14 mg, 0.114 mmol) and the thin suspension was stirred overnight at room temperature, after which the solution becomes clear. Next day, $H_2O$ (20 mL) and MeOH (10 mL) are added and after stirring for 10 min, the clear organic phase was isolated. The turbid aqueous phase was extracted with DCM. The combined organic extracts are concentrated. After purification by silica gel chromatography by eluting with 100% ethyl acetate followed by 10% MeOH/DCM, the purified residue was taken up in DCM (25 mL) and PBS (pH11, 25 mL). The mixture was stirred at room temperature for 15 min. Afterwards, the organic phase was separated out and the aqueous phase was extracted again with DCM (15 mL). The combined organics are dried ($MgSO_4$) for 30 min, filtered, washed with DCM, and concentrated to yield ((5-(dimethylamino)pentanoyl)azanediyl)bis(ethane-2,1-diyl)ditetradecanoate (405 mg). LCMS ESI+: m/z 654.1 (M+H).

Preparation of ((2-((2-(dimethylamino)ethyl)sulfonyl) acetyl)azanediyl)bis(ethane-2,1-diyl) ditetra-decanoate (SO2-S104)

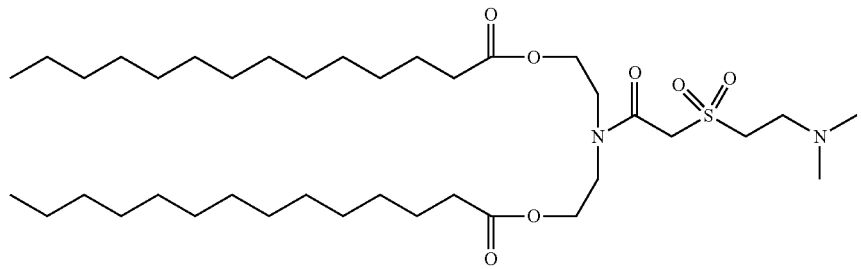

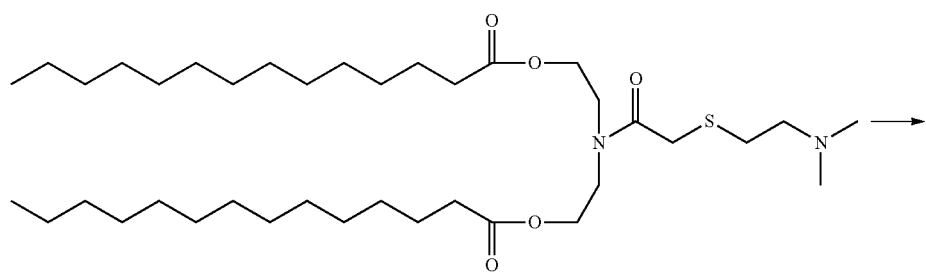

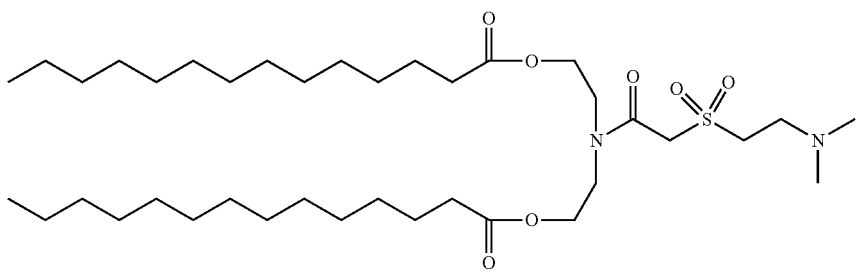

Synthesis of ((2-((2-(dimethylamino)ethyl)thio)acetyl) azanediyl)bis(ethane-2,1-diyl) ditetradecanoate (S104) was described. To ((2-((2-(dimethylamino)ethyl)thio)acetyl) azanediyl)bis(ethane-2,1-diyl)ditetradecanoate in a round-bottom flask, flushed with argon was added DCM (10 mL). The solution was cooled by an ice-bath. To this, was added mCPBA (a solution in DCM) slowly over 5 min. The ice bath was removed after the addition and the reaction was allowed to stir overnight at room temperature. After 3.5 hours, 2M DMA/THF (4.55 mL) was slowly added and the reaction mixture was allowed to stir overnight. The reaction mixture was then diluted with DCM to 75 mL. Washed with $H_2O$ (2×50 mL) and 10% $K_2CO_3$ (50 mL). Back extracted all aqueous washes with DCM (40 mL). The combined organics were dried ($MgSO_4$), filtered, and concentrated to yield a colorless oil. The reaction mixture was concentrated. Purification by silica gel chromatography eluting with a ethyl acetate/MeOH gradient yielded ((2-((2-(dimethyl-amino)ethyl)sulfonyl)acetyl)azanediyl)bis(ethane-2,1-diyl) ditetradecanoate (540 mg). LCMS ESI+: m/z 704.0 (M+H).

Preparation of ((((2-(dimethylamino)ethyl)thio)carbonyl)azanediyl)bis(ethane-2,1-diyl)ditetradecanoate (TU104)

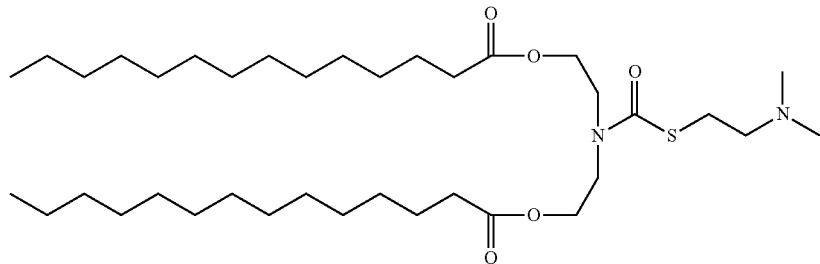

Step 1: Preparation of Intermediate 1: azanediylbis(ethane-2,1-diyl)ditetradecanoate

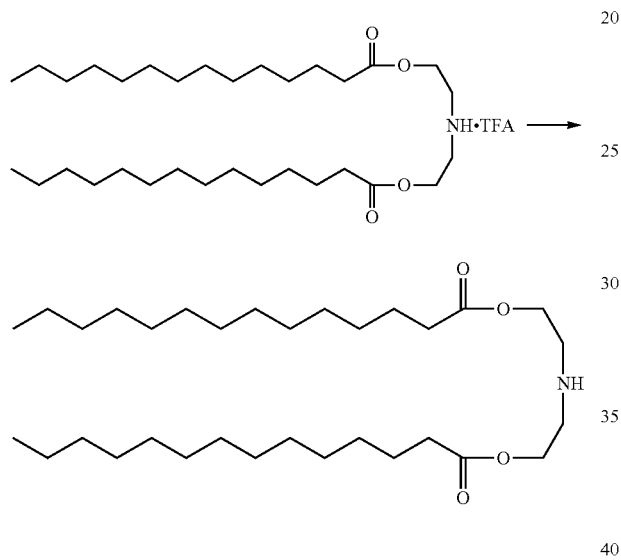

Synthesis of azanediylbis(ethane-2,1-diyl)ditetradecanoate TFA salt previously described. Azanediylbis(ethane-2,1-diyl)ditetradecanoate TFA salt was dissolved in DCM (50 mL) and PBS (pH11, 50 mL) was added. The mixture was stirred at room temperature for 15 min. Afterwards, the organic phase separated and the aqueous phase extracted again with DCM (25 mL). The combined organics were dried (MgSO$_4$) for 30 min, filtered, washed with DCM, and concentrated to yield azanediylbis(ethane-2,1-diyl) ditetradecanoate as the free base. Step 2: Preparation of TU104: ((((2-(dimethylamino)ethyl)thio)carbonyl)azanediyl)bis(ethane-2,1-diyl)ditetra-decanoate

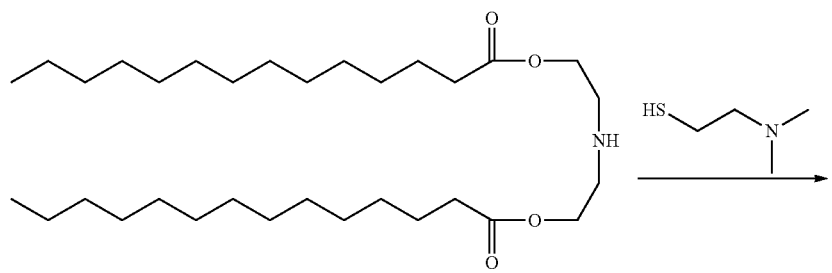

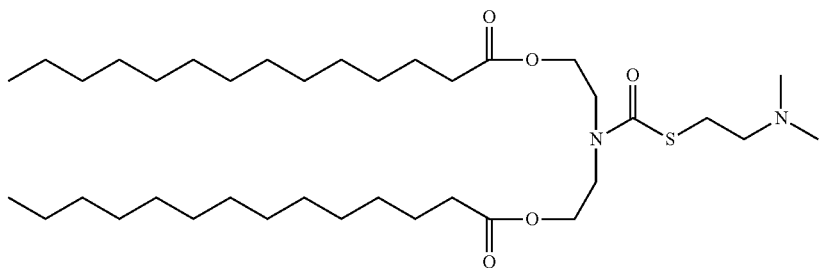

Trichloromethyl chloroformate (257 μL, 2.13 mmol) was added to a solution of 2-(dimethylamino)ethanethiol HCl salt (302 mg, 2.13 mmol) in dry DCM (20 mL) and stirred under a blanket of argon at room temperature for 4 h. Afterwards, DCM and excess diphosgene were removed in vacuo. Azanediylbis(ethane-2,1-diyl)ditetradecanoate free base (1068 mg, 2.03 mmol), DCM (20 mL) and triethylamine (580 μL, 4.16 mmol) were then added. After 16 h at room temperature the reaction mixture was diluted with DCM and washed with 1M HCl (75 mL), H₂O (75 mL) and PBS (pH11, 75 mL), dried (MgSO₄), filtered, and concentrated. Purification by silica gel chromatography eluting with ethyl acetate followed by a DCM/MeOH gradient yielded ((((2-(dimethylamino)ethyl)thio)carbonyl)azanediyl)bis(ethane-2,1-diyl)ditetradecanoate (120 mg). LCMS ESI+: m/z 657.5 (M+H).

Preparation of ((2-(2-(dimethylamino)ethoxy)acetyl)azanediyl)bis(ethane-2,1-diyl)ditetradecanoate (O104)

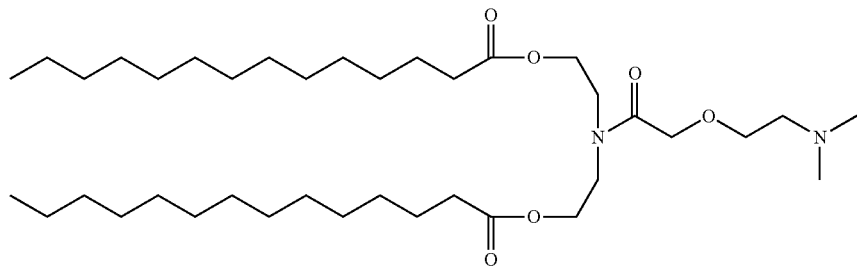

Step 1: Preparation of Intermediate 1: ((2-bromoacetyl)azanediyl)bis(ethane-2,1-diyl)ditetradecanoate

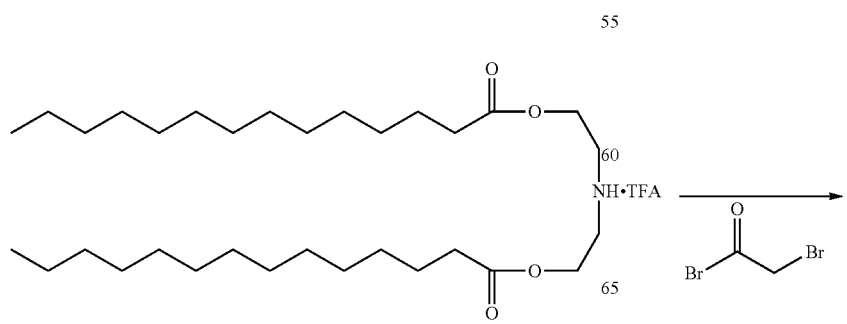

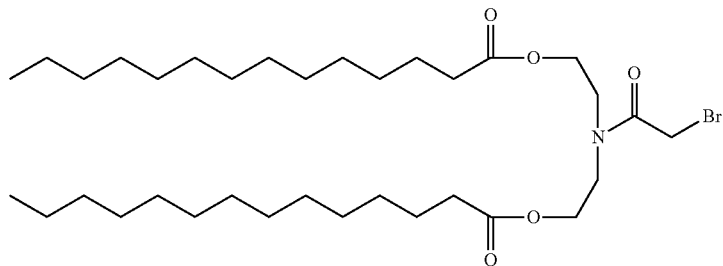

Synthesis of azanediylbis(ethane-2,1-diyl)ditetradecanoate TFA salt previously described. Azanediylbis(ethane-2,1-diyl)ditetradecanoate TFA salt (1500 mg, 2.34 mmol) was dissolved in DCM (20 mL) and placed in an ice-bath. Bromoacetyl bromide (214 µL, 2.46 mmol) was added followed by triethylamine (685 µL, 4.91 mmol). The ice-bath was removed and the reaction was allowed to stir overnight at room temperature under a blanket of inert gas. Next day, diluted with DCM to 100 mL. Washed with 1M HCl (75 mL), H$_2$O (75 ml), saturated NaHCO$_3$ solution (75 mL) and saturated brine solution (75 mL). Back extracted all aqueous washes with DCM (25 mL). Dried organics with MgSO$_4$, filtered and concentrated in vacuo. Purified by silica gel chromatography and eluting with 100% ethyl acetate. Pooled and concentrated fractions to yield ((2-bromoacetyl)azanediyl)bis(ethane-2,1-diyl)ditetradecanoate (1220 mg).

Step 2: Preparation of O104: ((2-(2-(dimethylamino)ethoxy)acetyl)azanediyl)bis(ethane-2,1-diyl)ditetradecanoate To a round-bottom flask equipped with stir bar, was added ((2-bromoacetyl)azanediyl)bis(ethane-2,1-diyl)ditetradecanoate (1.22 g, 1.87 mmol), N,N-dimethylethanolamine (197 µL, 1.96 mmol), potassium iodide (6.2 mg, 0.0374 mmol) and dry THF (25 mL). The resulting solution was cooled to −40° C. DBU (588 µL, 3.93 mmol) was added dropwise over 5 min and the reaction was warmed to 0° C. for 2 hours. The reaction mixture was concentrated. The residue was taken up with DCM, 1M HCl (12 mL) was added, and biphasic mixture stirred for 15 min. Then, basified using PBS (pH11). The organic layer was isolated, dried (MgSO$_4$), filtered and concentrated. Purification by silica gel chromatography eluting with 100% ethyl acetate followed by a DCM/MeOH gradient yielded ((2-((2-(dimethylamino)ethoxy)acetyl)azanediyl)bis(ethane-2,1-diyl)ditetradecanoate (53 mg). LCMS ESI+: m/z 655.6 (M+H).

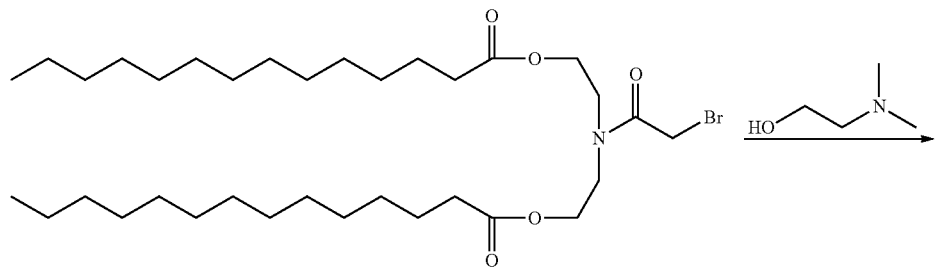

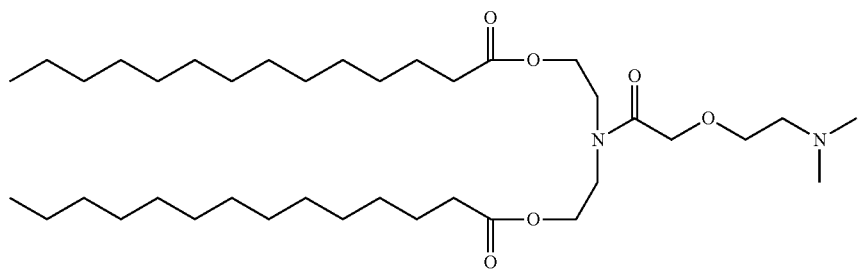

Preparation of ((2-((4-(dimethylamino)butanoyl)oxy)acetyl)azanediyl)bis(ethane-2,1-diyl)ditetra-decanoate (HEDC-M1)

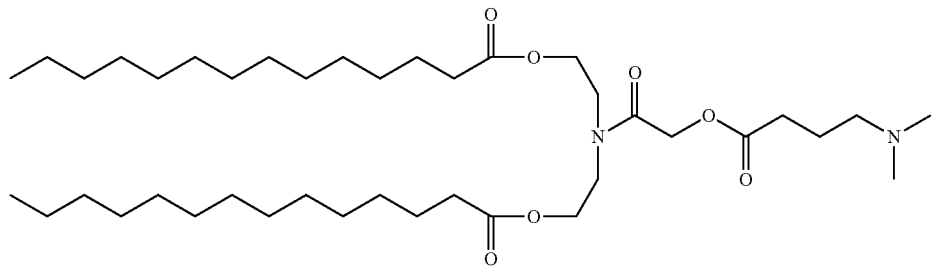

Step 1: Preparation of Intermediate 1: ((2-(benzyloxy)acetyl)azanediyl)bis(ethane-2,1-diyl)ditetradecanoate

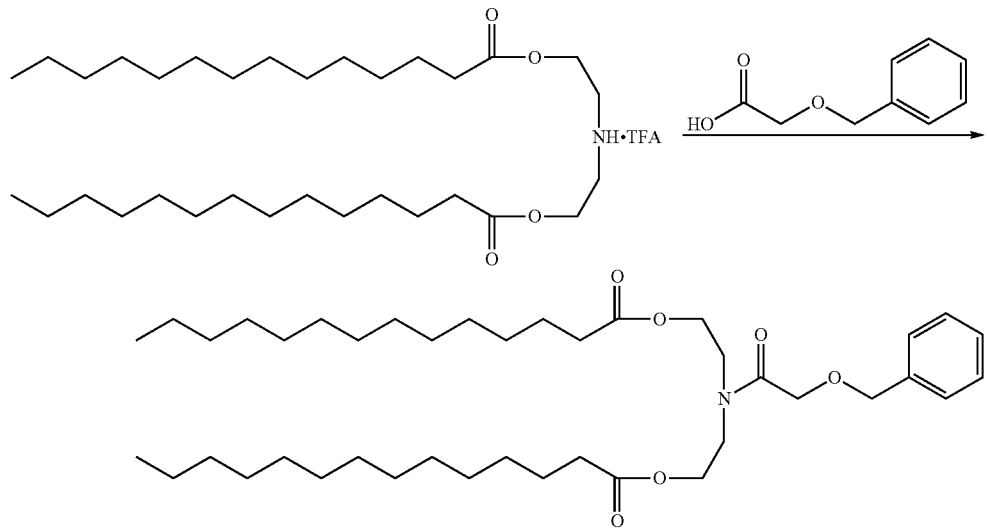

Synthesis of azanediylbis(ethane-2,1-diyl)ditetradecanoate TFA salt previously described. Azanediylbis(ethane-2,1-diyl)ditetradecanoate TFA salt was stirred in DCM (25 mL) with 10% K₂CO₃ (12.5 mL) at 0-5° C. After 30 min, the organic layer was isolated and the aqueous layer was further extracted with DCM (12 mL). The combined organic phases are stirred with MgSO₄ for 30 min at 0-5° C., filtered, washed with DCM (12 mL). To the combined filtrates are added benzyloxy acetic acid (402 µL, 2.81 mmol), EDC HCl salt (673 mg, 3.51 mmol), and DMAP (29 mg, 0.234 mmol). The suspension was allowed to stir at room temperature overnight. Next day, H₂O (25 mL) and MeOH (12 mL) was added and after stirring for 10 min the clear organic phase was isolated. The turbid aqueous phase was extracted with DCM (25 mL). The combined organic extracts dried with MgSO₄, filtered and concentrated. Purification by silica gel chromatography eluting with a hexanes/ethyl acetate gradient yielded ((2-(benzyloxy)acetyl)azanediyl)bis(ethane-2,1-diyl)ditetradecanoate (1.28 g).

Step 2: Preparation of Intermediate 2: ((2-hydroxyacetyl)azanediyl)bis(ethane-2,1-diyl)ditetradecanoate

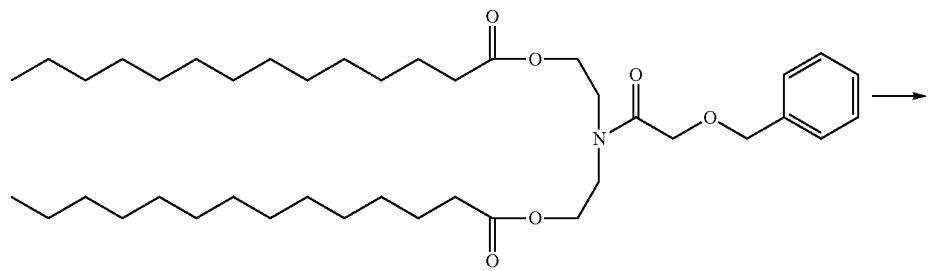

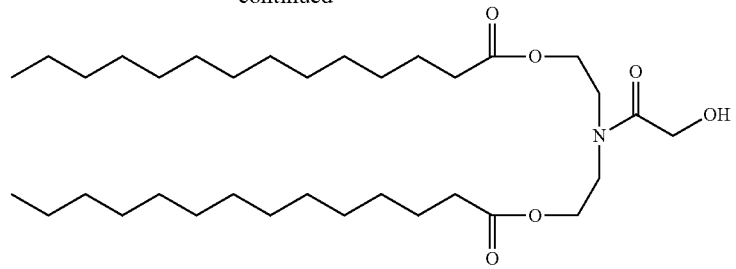

((2-(benzyloxy)acetyl)azanediyl)bis(ethane-2,1-diyl) ditetradecanoate (1.28 g, 1.80 mmol) was dissolved in a round-bottom flask with MeOH (20 mL). The flask was capped and flushed with argon. 10% Pd/C (135 mg) was added and the flask was once again flushed with argon. All air was removed via vacuum pump and then a 8" balloon filled with $H_2$ gas was added. Reaction was allowed to stir vigorously at room temperature. After 30 min, the reaction mixture was filtered (CELITE®), washed with methanol, concentrated to residue, taken up in DCM (25 mL) and 10% $K_2CO_3$ (25 mL). The mixture was stirred for 15 min and then the organic layer isolated. The aqueous wash was back extracted with DCM (15 mL). The combined organics were dried with $MgSO_4$, filtered and concentrated to yield ((2-hydroxyacetyl)azanediyl)bis(ethane-2,1-diyl)ditetradecanoate (990 mg).

Step 3: Preparation of HEDC-M1: ((2-((4-(dimethylamino)butanoyl)oxy)acetyl)azanediyl)bis(ethane-2,1-diyl) di-tetradecanoate ((2-hydroxyacetyl)azanediyl)bis(ethane-2,1-diyl)ditetradecanoate (990 mg, 1.70 mmol) was stirred in DCM (20 mL) and 4-Dimethylamino-butyric acid (268 mg), EDC HCl salt (487 mg) and DMAP (21 mg) was added. The suspension was allowed to stir at room temperature overnight. Next day, $H_2O$ (20 mL) and MeOH (10 mL) added and after stirring for 10 minutes the clear organic phase was isolated. The turbid aqueous phase was extracted with DCM (20 mL). The combined organic extracts dried with $MgSO_4$, filtered and concentrated. Crude material was purified by silica gel chromatography eluting with a DCM/MeOH gradient. Pooled and concentrated fractions were concentrated and taken up with DCM (25 mL) and PBS (pH11, 25 mL). The mixture was stirred at room temperature for 15 min. Afterwards, the organic phase was isolated, and the aqueous phase was extracted again with DCM (25 mL). The combined organics are dried ($MgSO_4$), filtered, and concentrated to yield ((2-((4-(dimethylamino)butanoyl)oxy)acetyl)

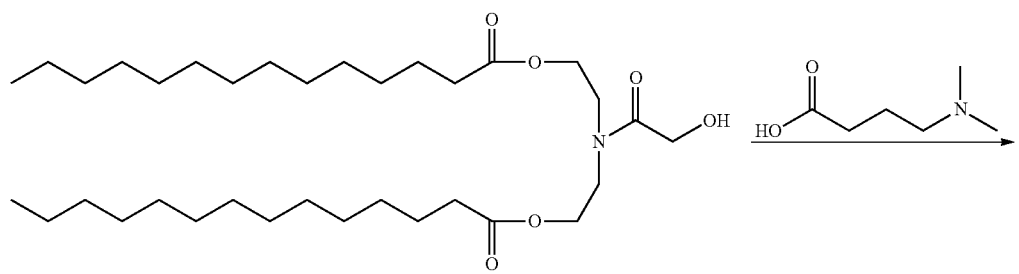

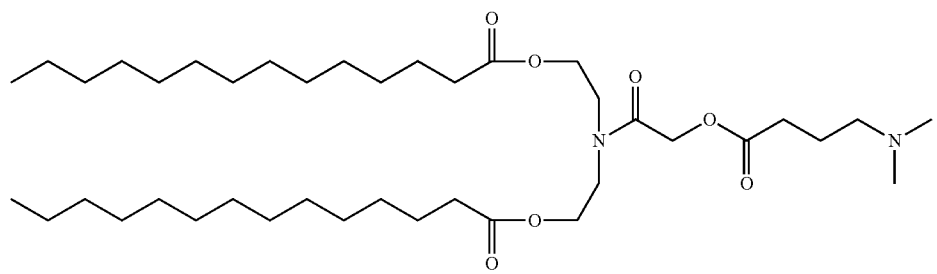

azanediyl)bis(ethane-2,1-diyl)ditetradecanoate (672 mg). LCMS ESI+: m/z 697.6 (M+H).

Preparation of (Z)-((5-(dimethylamino)pentanoyl) azanediyl)bis(ethane-2,1-diyl) dioleate ($C_{104}$-DO)

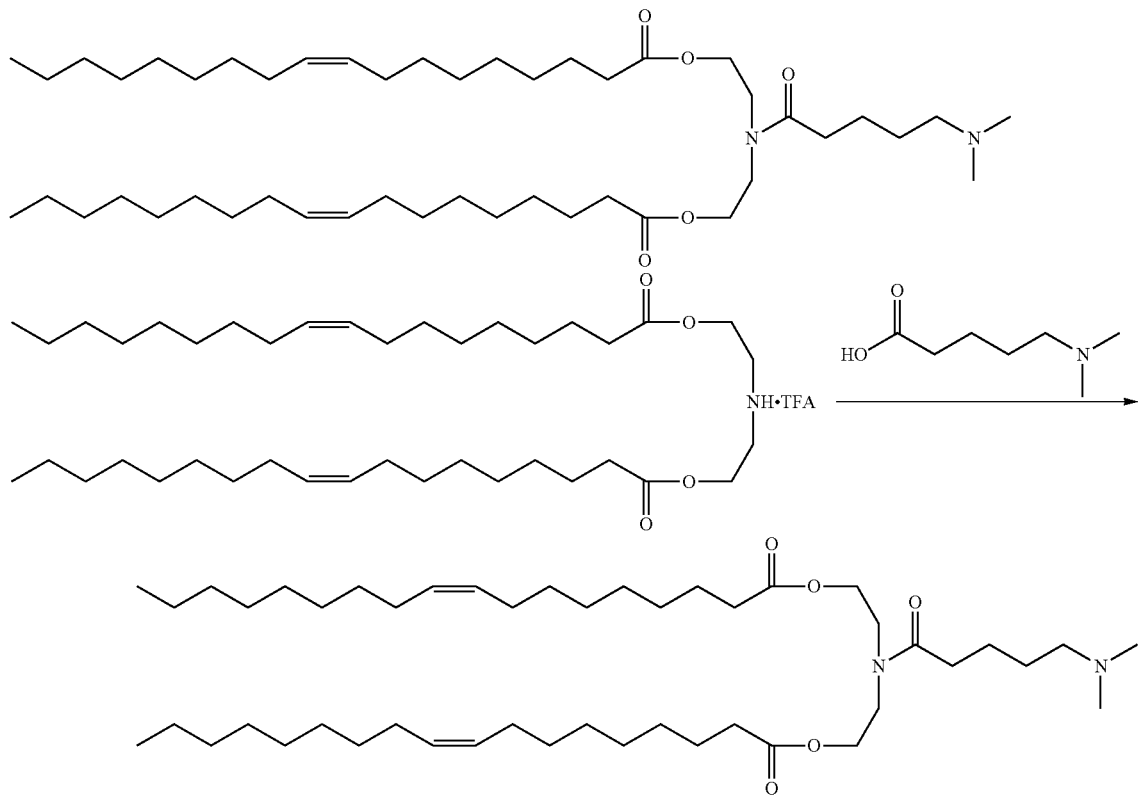

Synthesis of (Z)-azanediylbis(ethane-2,1-diyl)dioleate TFA salt previously described. (Z)-azanediylbis(ethane-2,1-diyl) dioleate TFA salt (1.50 g, 2.37 mmol) was stirred in DCM (20 mL) with 10% $K_2CO_3$ (10 mL) at 0-5° C. After 30 min, the organic phase was isolated and the aqueous phase was further extracted with DCM (10 mL). The combined organic phases are stirred with $MgSO_4$ for a period of 30 min at 0-5° C., filtered and washed with DCM (15 mL). To the combined filtrates are added 5-(dimethylamino)pentanoic acid (516 mg, 2.84 mmol), EDC HCl salt (681 mg, 3.55 mmol), DMAP (29 mg, 0.237 mmol) and the suspension was stirred overnight at room temperature, after which period of time became clear solution was formed. Next day, $H_2O$ (20 mL) and MeOH (10 mL) added and after stirring for 10 min, the clear organic phase was isolated. The turbid aqueous phase was extracted with DCM. The combined organics are dried ($MgSO_4$), filtered and concentrated. After purification by silica gel chromatography eluting with a DCM/MeOH gradient, the pooled and concentrated fractions are taken up with DCM (25 mL) and PBS (pH11, 25 mL). The mixture was stirred at room temperature for ~10 min. Afterwards, the organic phase was isolated out and the aqueous phase was extracted again with DCM (15 mL). The combined organics are dried ($MgSO_4$), filtered, and concentrated to yield (Z)-((5-(dimethylamino)pentanoyl)azanediyl)bis(ethane-2,1-diyl)dioleate (1.10 g). LCMS ESI+: m/z 761.7 (M+H).

Preparation of ((5-(((dimethylamino)methyl)thiophene-2-carbonyl)azanediyl)bis(ethane-2,1-diyl) di-tetradecanoate (T104)

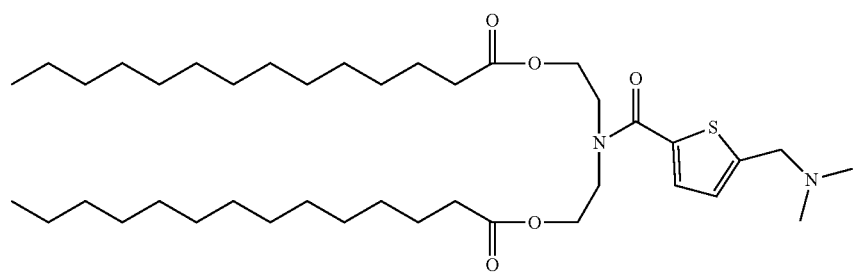

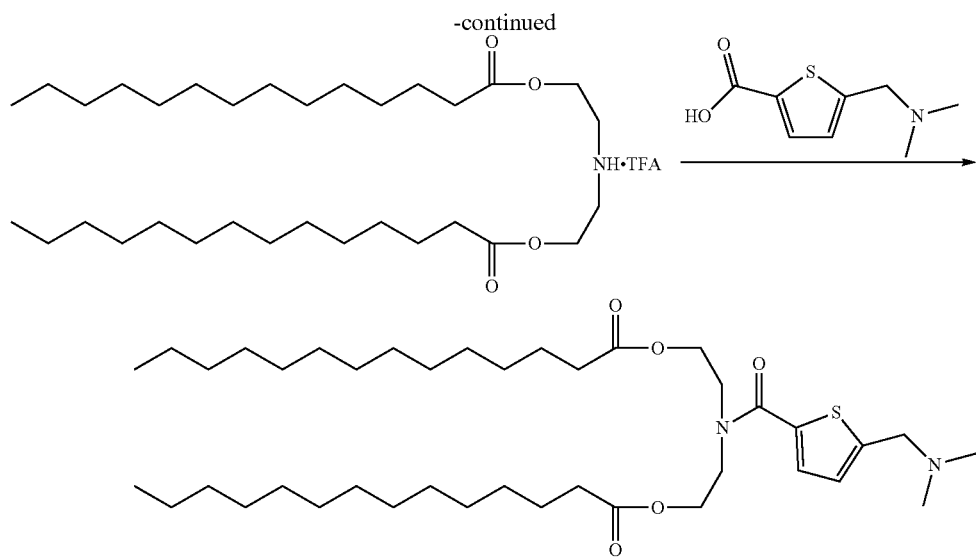

Synthesis of azanediylbis(ethane-2,1-diyl)ditetradecanoate TFA salt was previously described. Azanediylbis(ethane-2,1-diyl)ditetradecanoate TFA salt (1004 mg, 1.57 mmol) was stirred in DCM (20 mL) with 10% $K_2CO_3$ (20 mL) at 0-5° C. After 30 min, the organic phase was isolated and the aqueous phase was further extracted with DCM (10 mL). The combined organics are dried with $MgSO_4$ for 30 min at 0-5° C., filtered and washed with DCM (10 mL). To the combined filtrates were added ((dimethylamino)methyl)thiophene-2-carboxylic acid (350 mg, 1.89 mmol), EDC HCl salt (452 mg, 2.36 mmol), and DMAP (19.2 mg, 0.157 mmol). The suspension was allowed to stir at room temperature overnight. Next day, $H_2O$ (20 mL) and MeOH (10 mL) were added and after stirring for 10 min, the clear organic phase was isolated. The turbid aqueous phase was extracted with DCM (25 mL). The combined organics were dried ($MgSO_4$), filtered, and concentrated. After purification by silica gel chromatography eluting with a hexanes/ethyl acetate gradient, the pooled and concentrated fractions were taken up with DCM (20 mL) and PBS (pH11, 20 mL). The mixture was stirred at room temperature for ~10 min. Afterwards, the organic phase was isolated and the aqueous phase was extracted again with DCM (15 mL). The combined organics was dried ($MgSO_4$) for a period 30 min, filtered, washed with DCM, and concentrated to yield ((5-((dimethylamino)methyl)thiophene-2-carbonyl)azanediyl)bis(ethane-2,1-diyl)ditetradecanoate (482 mg). LCMS ESI+: m/z 693.6 (M+H).

Preparation of (Z)-(((2-(dimethylamino)ethyl)thio)carbonyl)azanediyl)bis(ethane-2,1-diyl) dioleate (TU104-DO)

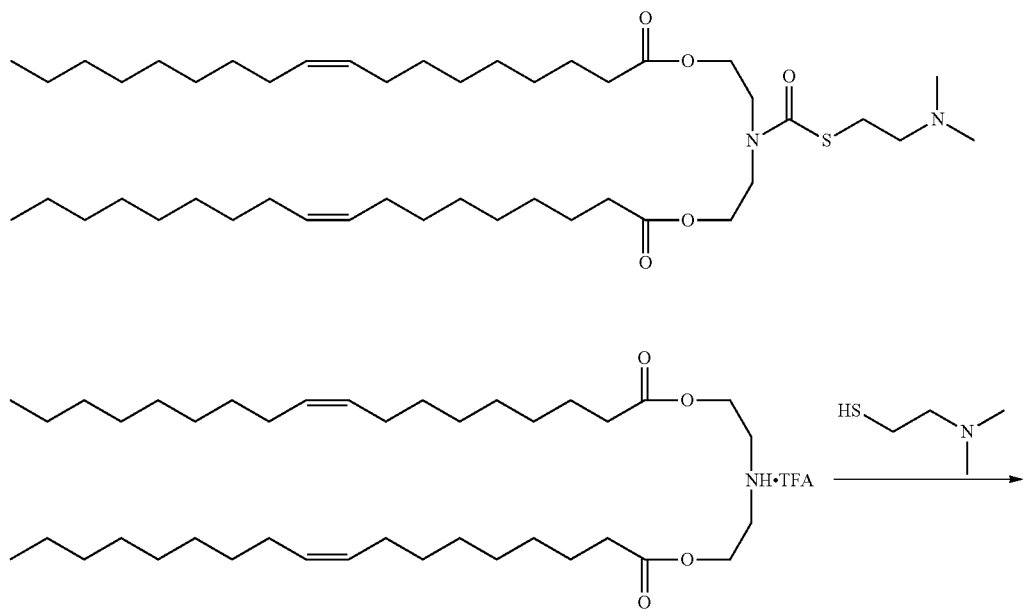

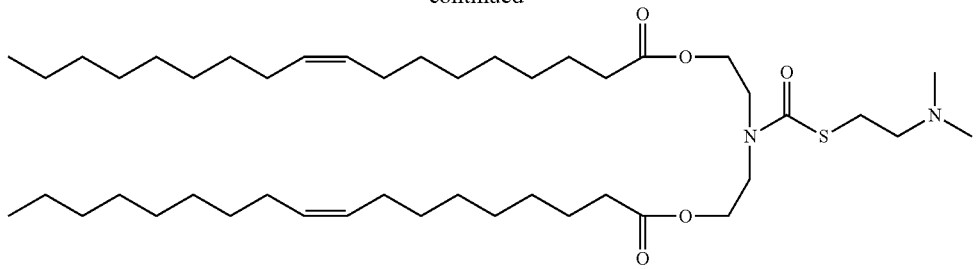

Synthesis of (Z)-((tert-butoxycarbonyl)azanediyl)bis(ethane-2,1-diyl)dioleate previously described. (Z)-((tert-butoxycarbonyl)azanediyl)bis(ethane-2,1-diyl)dioleate (4.20 g, 5.72 mmol) was dissolved in DCM (20 mL) and cooled to 0° C. in an ice bath. TFA (20 mL) was added and the mixture was allowed to stir under a blanket of inert gas for 20 min. Afterwards, the reaction mixture was concentrated in vacuo. The residue was partitioned between 10% $K_2CO_3$ (20 mL) and DCM (20 mL), and stirred in an ice bath for 20 min. The organic layer was isolated, dried ($MgSO_4$), and filtered. Diphosgene (1.38 mL, 11.4 mmol) was added to (Z)-azanediylbis(ethane-2,1-diyl) dioleate material in DCM and stirred under a blanket of inert gas at room temperature. Next day, DCM and excess diphosgene were removed in vacuo. 2-(dimethylamino)ethane thiol HCl salt (4.05 g, 28.6 mmol) was taken up in DCM (50 mL) and triethylamine (5.2 mL, 37.2 mmol) and added to (Z)-((chlorocarbonyl)azanediyl)bis(ethane-2,1-diyl) dioleate residue. Material was allowed to stir overnight at room temperature. Next day, diluted with DCM and washed with 0.3M HCl (75 mL), $H_2O$ (75 mL) and 10% $K_2CO_3$ (75 mL). Back extracted all aqueous washes with DCM (25 mL). The combined organics were dried over $MgSO_4$, filtered and concentrated. Purification by silica gel chromatography eluting with DCM/MeOH gradient yielded (Z)-((((2-(dimethylamino)ethyl)thio)carbonyl)azanediyl)bis(ethane-2,1-diyl)dioleate (1.90 g). LCMS ESI+: m/z 765.7 (M+H).

Preparation of (((3-(dimethylamino)propoxy)carbonyl)azanediyl)bis(ethane-2,1-diyl) ditetradeca-noate (CB104)

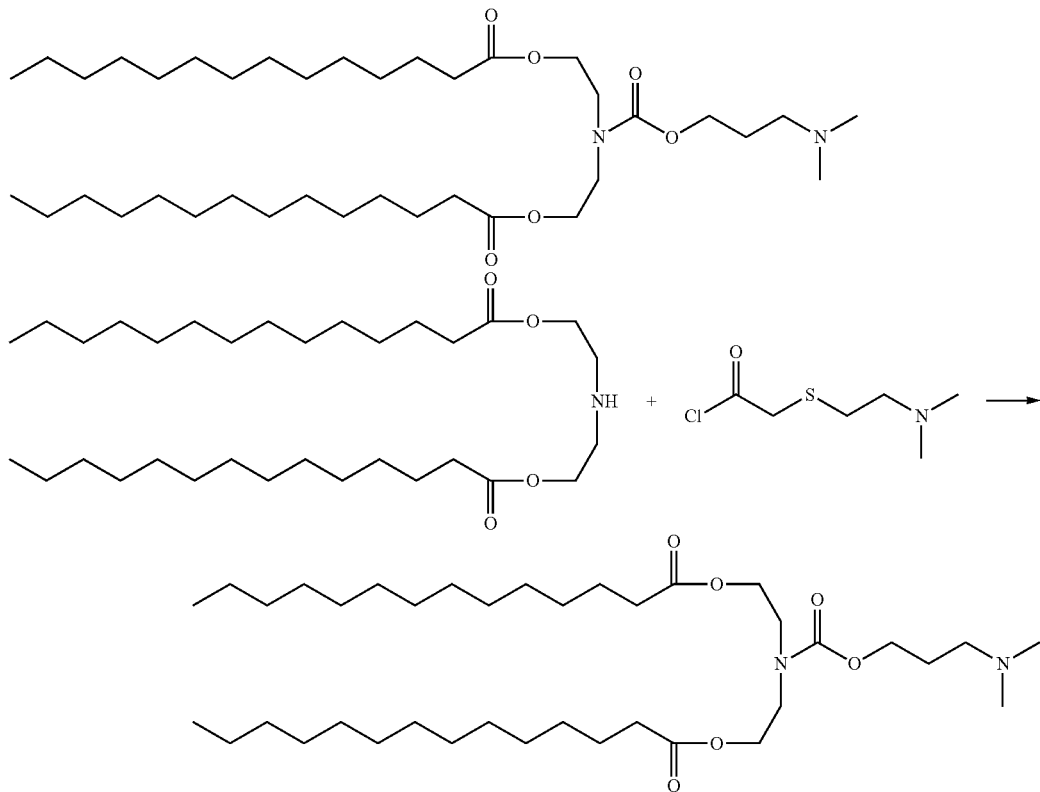

Synthesis of azanediylbis(ethane-2,1-diyl) ditetradecanoate previously described. Diphosgene (266 µL, 2.2 mmol) was added to dimethylaminopropanol (413 mg, 4.00 mmol) in DCM (10 mL) and stirred under a blanket of inert gas at room temperature for 4 h. The DCM and excess diphosgene was removed in vacuo and azanediylbis(ethane-2,1-diyl) ditetradecanoate was added. The round-bottom flask was flushed with argon and DCM (10 mL) and triethylamine (859 µL, 6.16 mmol) was added. Material was allowed to stir overnight at room temperature. The reaction mixture was then diluted with DCM and washed with 0.3M HCl (75 mL), H₂O (75 mL) and 10% K₂CO₃ (75 mL). Back extracted all aqueous washes with DCM (25 mL). The combined organics were dried over MgSO₄, filtered and concentrated. Purification by silica gel chromatography eluting with DCM/MeOH gradient yielded (((3-(dimethylamino)propoxy)carbonyl)azanediyl)bis(ethane-2,1-diyl)ditetradecanoate (87 mg).). LCMS ESI+: m/z 655.59 (M+H).

Preparation of (((2-(dimethylamino)ethoxy)carbonyl)azanediyl)bis(ethane-2,1-diyl) ditetradecanoate (CA104)

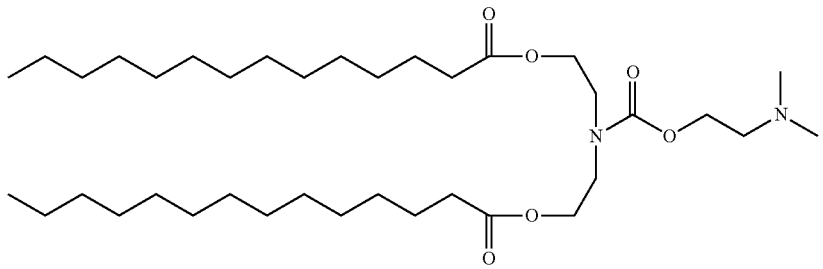

Step 1: Preparation of Intermediate 1: (((4-nitrophenoxy)carbonyl)azanediyl)bis(ethane-2,1-diyl) ditetradeca-noate

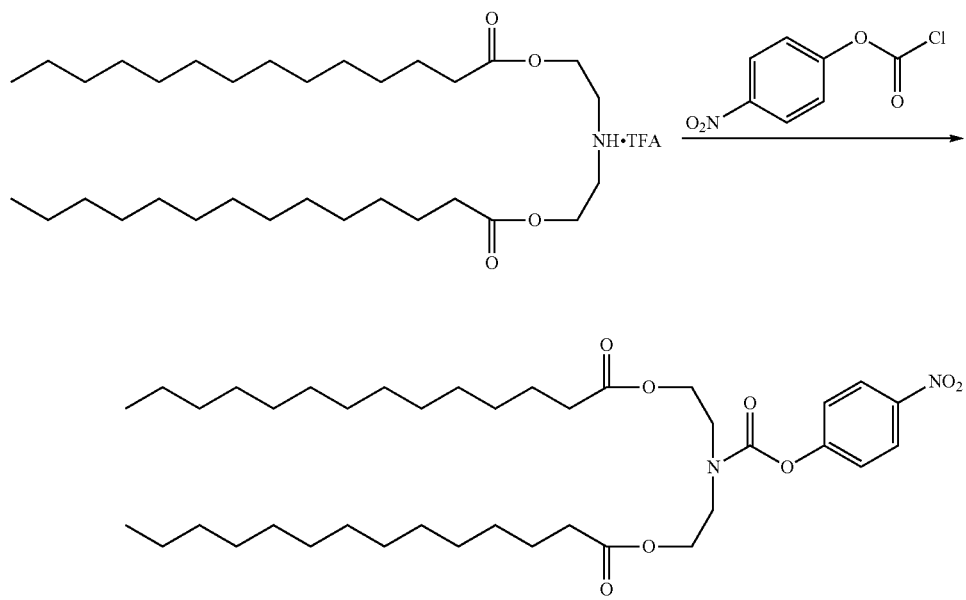

Synthesis of azanediylbis(ethane-2,1-diyl)ditetradecanoate TFA salt previously described. Azanediylbis(ethane-2,1-diyl)ditetradecanoate TFA salt was dissolved in dry DCM (10 mL) and triethylamine (654 µL, 4.69 mmol) was added. The reaction vessel was flushed with inert gas and 4-nitrophenyl chloroformate was added. Material was allowed to stir at RT overnight. The reaction mixture was quenched with water (50 mL) and DCM (50 mL). The organic layer was isolated, and the aqueous layer was extracted further with DCM (2×50 mL). The combined organics were dried over MgSO₄, filtered and concentrated. Purification by silica gel chromatography eluting with hexanes/ethyl acetate gradient yielded (((4-nitrophenoxy)carbonyl)azanediyl)bis(ethane-2,1-diyl)ditetradecanoate.

Step 2: Preparation of CA104: (((2-(dimethylamino)ethoxy) carbonyl)azanediyl)bis(ethane-2,1-diyl) ditetra-decanoate

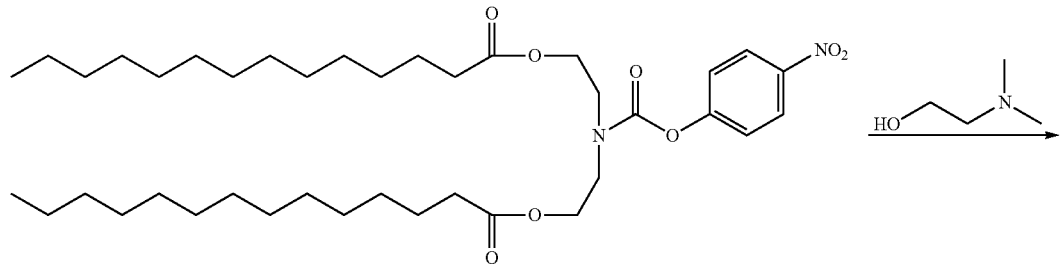

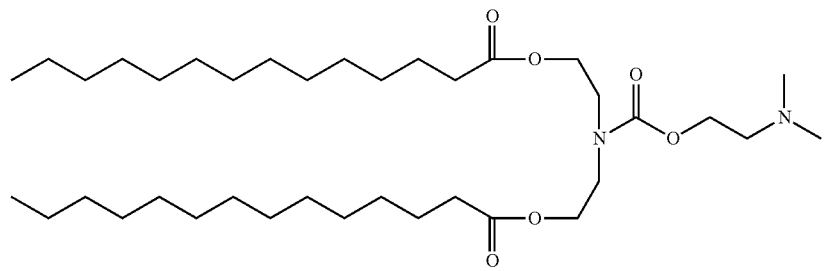

To ((((4-nitrophenoxy)carbonyl)azanediyl)bis(ethane-2,1-diyl) ditetradecanoate, was added 2-dimethylaminoethanol (2 mL) and heated to 140° C. with a condensing column for 20 min. Afterwards, the crude material was purified by silica gel chromatography eluting with a DCM/MeOH gradient to yield ((((2-(dimethylamino)ethoxy)carbonyl)azanediyl)bis (ethane-2,1-diyl)ditetradecanoate (38 mg). LCMS ESI+: m/z 641.7 (M+H).

Preparation of ((2-(dimethylamino)acetyl)azanediyl)bis(ethane-2,1-diyl) ditetradecanoate (INT-4)

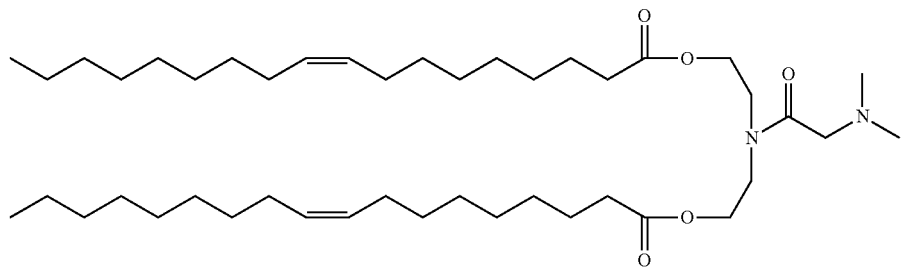

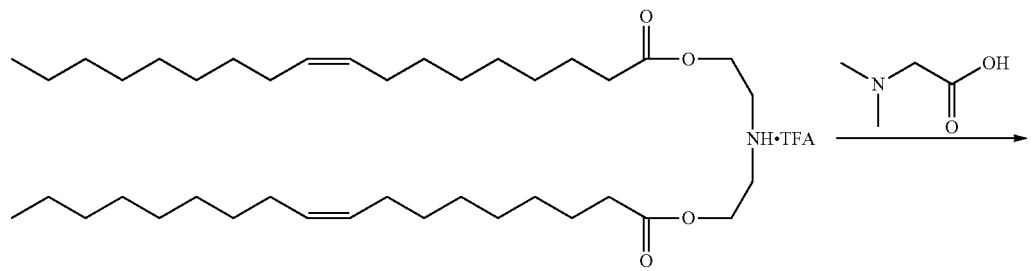

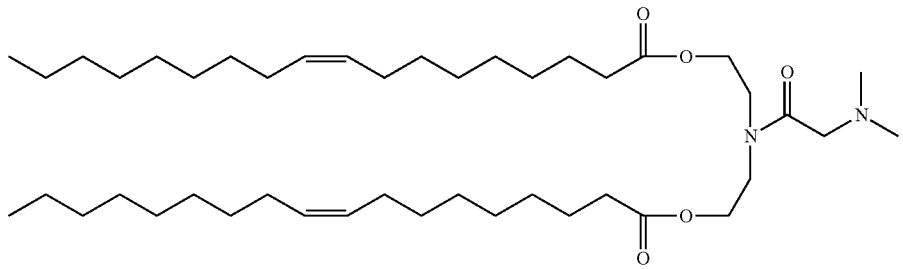

Synthesis of (Z)-((2-(dimethylamino)acetyl)azanediyl)bis(ethane-2,1-diyl) dioleate was prepared in similar fashion as i-Prop-DODC with the substitution of dimethylglycine for 3-(dimethylamino)propionic acid. QTOF MS ESI+: m/z 720.1 (M+H).

Preparation of ((2-((2-(dimethylamino)ethyl)thio)acetyl)azanediyl)bis(ethane-2,1-diyl)ditetradeca-noate (S104)

The reaction mixture was eventually heated and stirred at 40° C. for a period of two hours, at which point TLC indicated completion of reaction. CELITE® 545 (74 g) was added, and the mixture was filtered through a G3 glass-sintered plate over 6 minutes, washing with ethanol (2×105 mL). The combined cloudy filtrates are evaporated from a 50° C. bath to give 110 g of white solid. The solid was

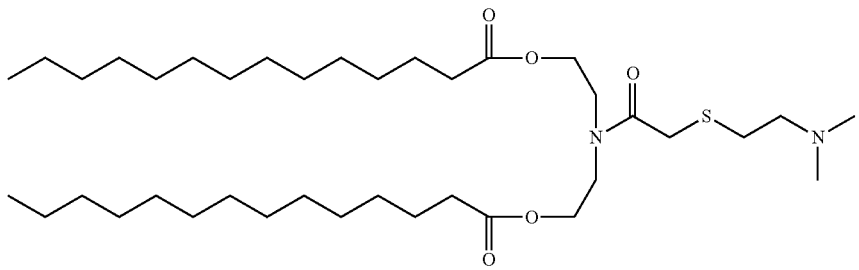

Step 1: Preparation of intermediate 1: 2-((2-(dimethylamino)ethyl)thio)acetic acid hydrochloride:

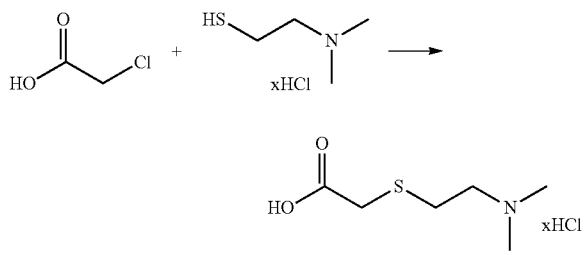

Ethanol (500 mL) was degassed by three times evacuation to 60 mBar for 1-2 minutes and pressurizing with nitrogen. Chloroacetic acid (36.9 g, 0.391 mol) was added and a clear solution was formed after having stirred for 5 minutes at 17-20° C. 2-(Dimethylamino)-ethanethiol hydrochloride (52.7 g, 0.372 mol) was added, and a clear solution was formed after having stirred for 20 minutes at 25° C. Solid sodium hydroxide (47.7 g, 1.19 mol) was added in portions over a period of 20 minutes with cooling in order to keep the temperature below 35° C.—a short period at 44° C. was observed. Almost immediate precipitation was observed.

dissolved in water (250 mL) then the pH was adjusted from 13.1 (30° C.) to 10.5 (31° C.), using concentrated HCl (5.5 mL) to give a very pale yellow solution. The aqueous phase was washed with DCM (3×100 mL) to remove the disulphide impurity (all 3 washes required). Concentrated HCl was added to the aqueous phase (pH 10.7, temp. 22° C.) until the pH was 1.4 (57.5 mL added, temp. 35° C.). The aqueous phase was washed with DCM (100 mL) and then concentrated to dryness (bath temperature 55° C.). Toluene (250 mL) was added, the mixture was concentrated to dryness (bath temperature 55° C.) and this was repeated once to give a wet white solid (98 g). Acetonitrile (750 mL) was added to the solid, the mixture was stirred at 55° C. for a period of 45 minutes, and then filtered through a G3 glass-sintered plate. Acetonitrile (250 mL) was added to the filter cake, the mixture was stirred at 55° C. for a period of 25 minutes and then filtered through a G3 glass-sintered plate, washing with acetonitrile (50 mL). The combined filtrates are concentrated to 300 mL, resulting in a heavy, white precipitate. The mixture was cooled under nitrogen and stirred at 0° C. for a period of 30 minutes. The precipitate was isolated by filtration through a G3 glass sintered plate, and the filter cake was washed with cold acetonitrile (100 mL). Drying under reduced pressure for 3 days gives 47.0 g (63%) of 2-((2-(dimethylamino)ethyl)thio)acetic acid hydrochloride.

Step 2: Preparation of S104: ((2-(dimethylamino)ethyl)thio) acetyl)azanediyl)bis(ethane-2,1-diyl) ditetradecanoate

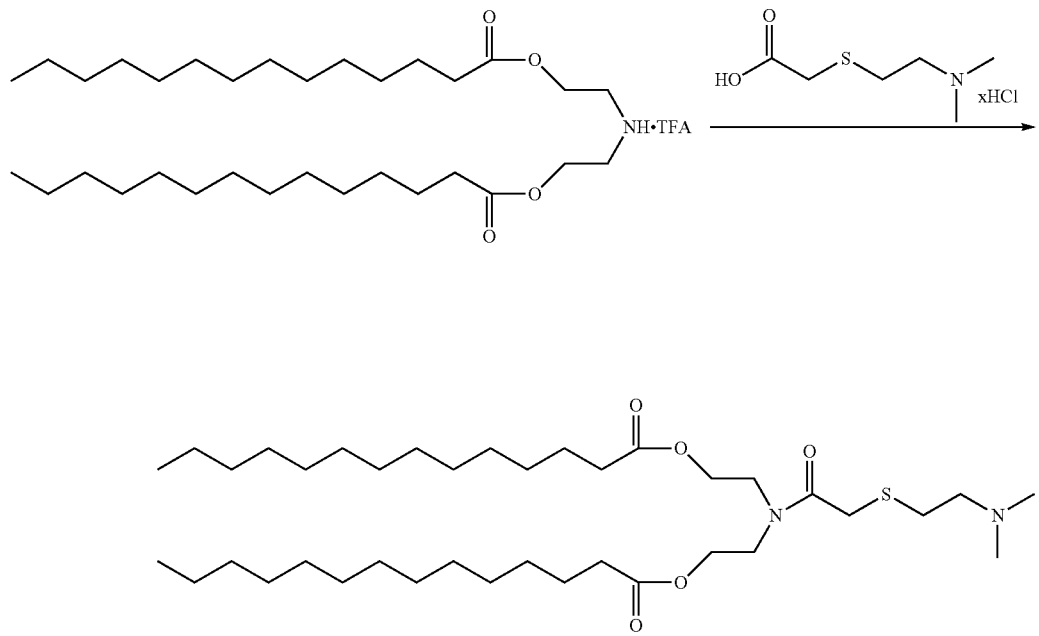

Synthesis of azanediylbis(ethane-2,1-diyl)ditetradecanoate TFA salt previously described. Azanediylbis(ethane-2,1-diyl)ditetradecanoate TFA salt (152 g, 238 mmol) was stirred with DCM (2.3 L) and 10% potassium bicarbonate (1.15 L) at 0-5° C. The organic phase was separated and the aqueous phase was further extracted with DCM (1.15 L). The combined organic phases were stirred with magnesium sulfate hydrate (236 g) for a period of 30 minutes at 0-5° C., filtrated and washed with DCM (1.15 L). To the combined filtrates was added 2-((2-(dimethylamino)ethyl)thio)acetic acid hydrochloride (57.0 g, 285 mmol), EDC hydrochloride (68.4 g, 357 mmol) and DMAP (2.91 g, 23.8 mmol), and the thin suspension was stirred overnight at ambient temperature, after which period of time a clear solution was formed. water (2.3 L) and methanol (460 mL) are added and after having stirred for a period of 10 minutes the clear organic phase was separated. The turbid aqueous phase (pH 3.0) was extracted with DCM (575 mL). The combined organic extracts were concentrated yielding 143 g of crude material as the hydrochloride salt. The crude material (142.6 g) was transferred to a distillation flask with DCM (500 mL), and ethyl acetate (1 L) was added. The solution was heated to distillation at atmospheric pressure, and distillation was continued over a period of 70 minutes in order to obtain a temperature of the residue of 76° C. A total volume of 1.4 L was obtained by addition of ethyl acetate (800 mL), and ethanol (70 mL) was added. The clear solution at 50° C. was cooled to 37° C. and seed crystals were added. Having observed initiation of significant crystallization over a period of 10 minutes at 37-35° C., the suspension was cooled and stirred at 0° C. overnight and the precipitate was isolated by filtration, and washed with cold ethyl acetate (210 mL). Drying to a constant weight at ambient temperature in oil pump vacuum over a period of 4.5 hours gave 134 g of recrystallized material as the hydrochloride salt, white crystalline solid.

Tripotassium phosphate (85 g, 0.40 mol) and dipotassium hydrogen phosphate (226 g, 1.30 mol) were added to purified water (1.7 L), and the solution formed with pH 10.9 was cooled to 18-20° C. DCM (1.3 L) and recrystallized S104 hydrochloride (133.0 g, 0.188 mol) are added, and the mixture was stirred for a period of 10 min minutes. A clear organic phase was separated at moderate rate (over a period of 35 minutes), and the turbid aqueous phase was further extracted with DCM (650 mL). The combined organic phases were stirred with magnesium sulfate hydrate (65 g) for a period of 40 minutes, and the mixture was filtered, washing with DCM (200 mL). The combined filtrates were evaporated from a 50° C. water bath under reduced pressure (down to 20 mBar, at which pressure evaporation was continued for one hour). Additional evaporation from a 15-20° C. water bath at oil pump vacuum, resulted in 126 g partially solidified oil. Cooling in −20° C. cooling bath gave complete solidification, and after drying at −20° C. under vacuum for two days we obtained 126 g of ((2-((2-(dimethylamino)ethyl)thio)acetyl)azanediyl)bis(ethane-2,1-diyl) ditetradecanoate, also known as S104. HPLC indicates 98.1% purity. QTOF MS ESI+: m/z 671.6 (M+H).

Preparation of (9Z,9'Z)-((2-((2-(dimethylamino)ethyl)thio)acetyl)azanediyl)bis(ethane-2,1-diyl) bis(tetradec-9-enoate) (S104-DMO)

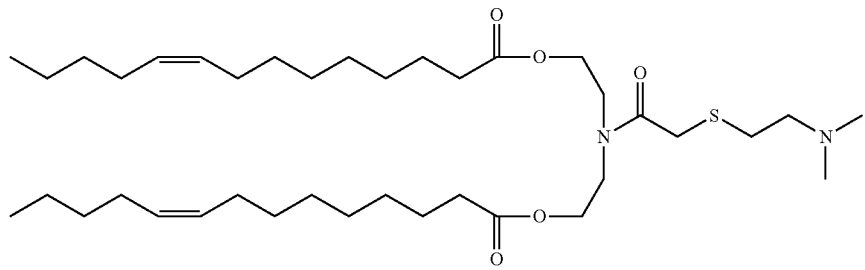 [SMILES: CCCC/C=C\CCCCCCCC(=O)OCCN(CCOC(=O)CCCCCCC/C=C\CCCC)C(=O)CSCCN(C)C]

Step 1: Preparation of Intermediate 1: (9Z,9'Z)-((tert-butoxycarbonyl)azanediyl)bis(ethane-2,1-diyl) bis(tetradec-9-enoate)

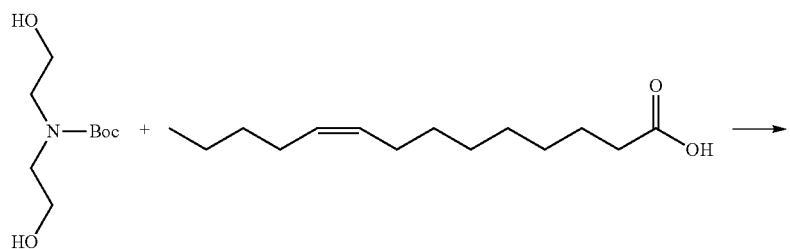

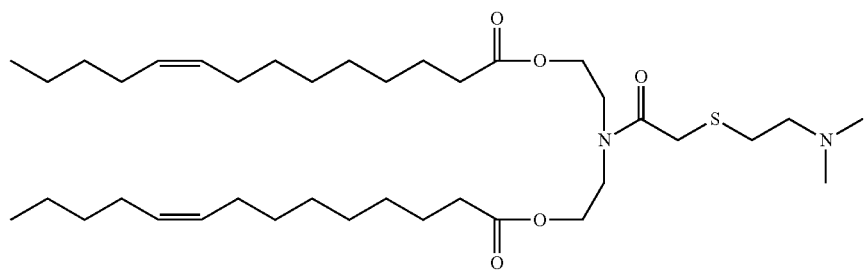

N-Boc-diethanolamine (454 mg, 2.21 mmol), myristoleic acid (1000 mg, 4.42 mmol) and DMAP (54 mg, 0.442 mmol) was dissolved in DCM (25 mL) and placed in a water bath at ambient temperature in a round-bottom flask was flushed with inert gas. EDC HCl salt (932 mg, 4.86 mmol) was added in 3 portions over 5 min. The reaction was allowed to stir overnight at room temperature under a blanket of inert gas. Next day, added $H_2O$ (25 mL) and stirred for 10 min. The organic layer was isolated and the aqueous layer was further extracted with DCM (50 mL). The combined organics were dried ($MgSO_4$) for 10 min, filtered and concentrated. Purification by silica gel chromatography eluting with a hexane/ethyl acetate gradient yielded (9Z,9')-((tert-butoxycarbonyl)azanediyl)bis(ethane-2,1-diyl)bis(tetradec-9-enoate) (1.10 g).

Step 2: Preparation of Intermediate 2: (9Z,9'Z)-azanediylbis(ethane-2,1-diyl)bis(tetradec-9-enoate)

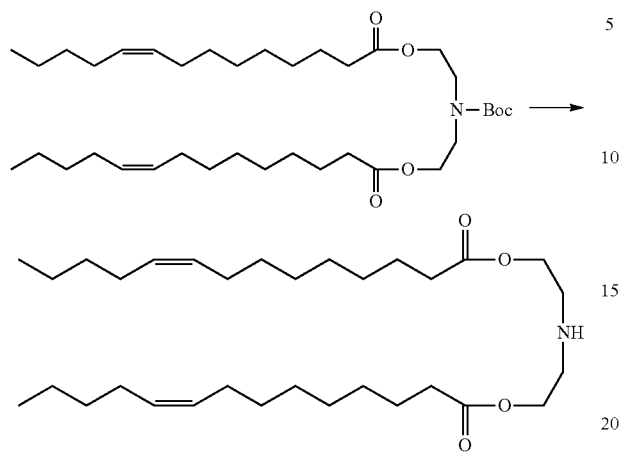

To (9Z,9'Z)-((tert-butoxycarbonyl)azanediyl)bis(ethane-2,1-diyl) bis(tetradec-9-enoate) (1100 mg, 1.77 mmol) in a round-bottom flask was added DCM (10 mL) and placed into an ice-bath. TFA (10 mL) was added and the mixture was allowed to stir for 20 min. The reaction mixture was then concentrated. Toluene was added to the residue to aid in azeotroping off excess TFA. The residue was placed back in the ice bath and PBS (pH=11, 25 mL) and DCM (25 mL) were added. The mixture was stirred for 15 min and the organic layer was then isolated. The turbid aqueous layer was extracted with DCM (10 mL). The combined organics were dried (MgSO$_4$) at 0° C. for 15 min, filtered and concentrated to yield (9Z,9'Z)-azanediylbis(ethane-2,1-diyl) bis(tetradec-9-enoate) (923 mg).

Step 3: Preparation of S104-DMO: (9Z,9'Z)-((2-((2-(dimethylamino)ethyl)thio)acetyl)azanediyl)bis(ethane-2,1-diyl) bis(tetradec-9-enoate)

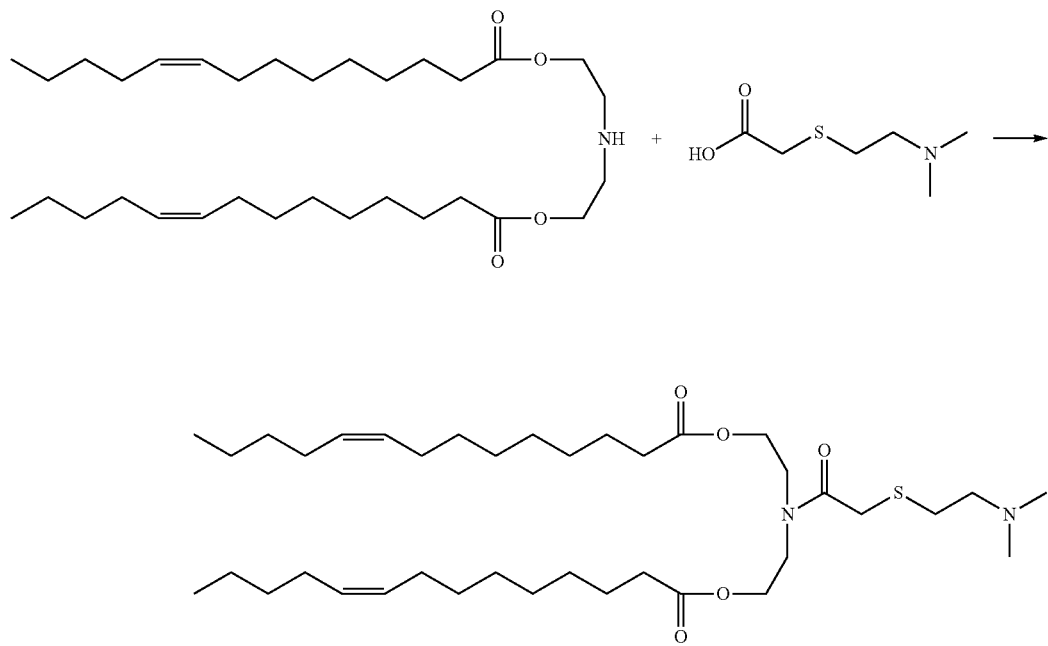

A mixture of (9Z,9'Z)-azanediylbis(ethane-2,1-diyl)bis(tetradec-9-enoate) (923 mg, 1.77 mmol), 2-((2-(dimethylamino)ethyl)thio)acetic acid (346 mg, 2.12 mmol) and EDC HCl salt (509 mg, 2.66 mmol) suspended in DCM (10 mL). DMAP (21.6 mg, 0.177 mmol) was added and the mixture was allowed to stir at room temperature overnight. Next day, H$_2$O (10 mL) and MeOH (10 mL) was added and after stirring for 10 min, the clear organic phase was isolated. The turbid aqueous phase was extracted with DCM (2×20 mL). The combined organic extracts are dried with MgSO$_4$, filtered and concentrated. After purification by silica gel chromatography eluting with a DCM/MeOH, the pooled and concentrated fractions were taken up in DCM (25 mL) and PBS (pH=11, 25 mL). The mixture was stirred at room temperature for ~10 min. Afterwards, the organic phase was isolated and the aqueous phase was extracted again with DCM (2×15 mL). The combined organics phase were dried (MgSO$_4$), filtered, and concentrated to yield (9Z,9'Z)-((2-((2-(dimethylamino)ethyl)thio)acetyl)azanediyl)bis(ethane-2,1-diyl) bis(tetradec-9-enoate) (589 mg). LCMS ESI+: m/z 667.6 (M+H).

Preparation of (R)-((1-methylpyrrolidine-2-carbonyl)azanediyl)bis(ethane-2,1-diyl) ditetradecanoate (Pro-DC)

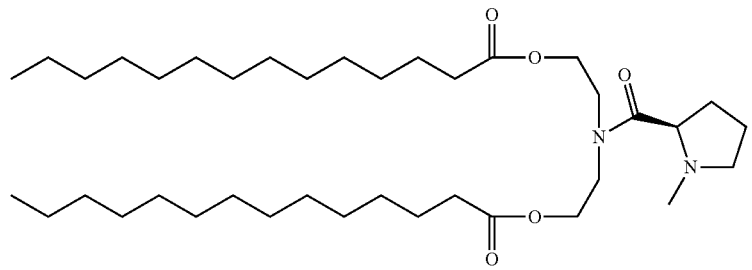 [SMILES: CCCCCCCCCCCCCC(=O)OCCN(CCOC(=O)CCCCCCCCCCCCC)C(=O)[C@H]1CCCN1C]

Step 1: Preparation of Pro-DC: (R)-((1-methylpyrrolidine-2-carbonyl)azanediyl)bis(ethane-2,1-diyl) ditetradecanoate

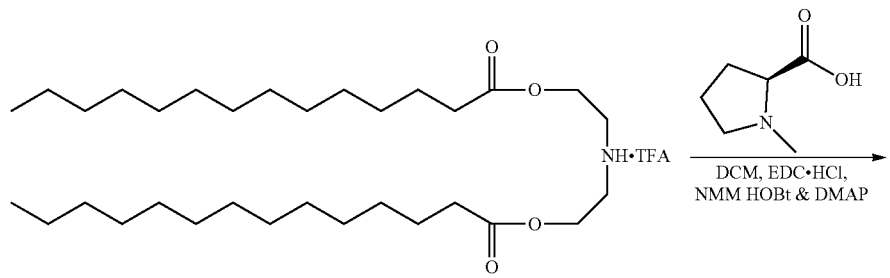

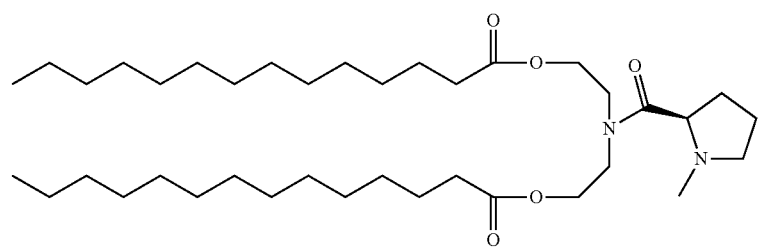

Synthesis of azanediylbis(ethane-2,1-diyl)ditetradecanoate TFA salt previously described. Azanediylbis(ethane-2,1-diyl)ditetradecanoate TFA salt (1000 mg, 1.56 mmol) was stirred with DCM (10 mL) and N-Methyl-L-Proline (228 mg, 1.77 mmol), HOBt H$_2$O (239 mg, 1.77 mmol) was added. NMM (365 µL, 3.32 mmol) was added and the solution became mostly clear. A suspension of EDC hydrochloride (518 mg, 2.70 mmol), NMM (257 µL, 2.34 mmol) and DMAP (19 mg, 0.156 mmol) in DCM (10 mL) was added and the mixture was stirred for about 12 hours at ambient temperature, after which period of time a clear solution was formed. Thereafter, the mixture was diluted with DCM (50 mL) and washed with 10% K$_2$CO$_3$, aqueous (60 mL). The organics were dried with MgSO$_4$, filtered and concentrated. The resulting compound was purified crude by Silica Gel chromatography, eluting with a (0-10)% methanol in DCM gradient to yield (R)-((1-methylpyrrolidine-2-carbonyl)azanediyl)bis(ethane-2,1-diyl)ditetradecanoate.
LCMS ESI+: m/z 637.6 (M+H).

Preparation of (9Z,9'Z,12Z,12'Z)-((2-((2-(dimethylamino)ethyl)thio)acetyl)azanediyl)bis(ethane-2,1-diyl) bis(octadeca-9,12-dienoate) (S104-DLin)

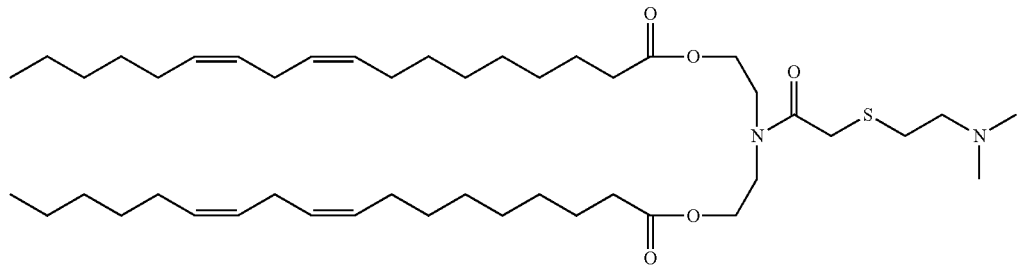 [SMILES: CCCCC/C=C\C/C=C\CCCCCCCC(=O)OCCN(CCOC(=O)CCCCCCC/C=C\C/C=C\CCCCC)C(=O)CSCCN(C)C]

Step 1: Preparation of Intermediate 1: (9Z,9',Z,12Z,12'Z)-((tert-butoxycarbonyl)azanediyl)bis(ethane-2,1-diyl) bis(octadeca-9,12-dienoate)

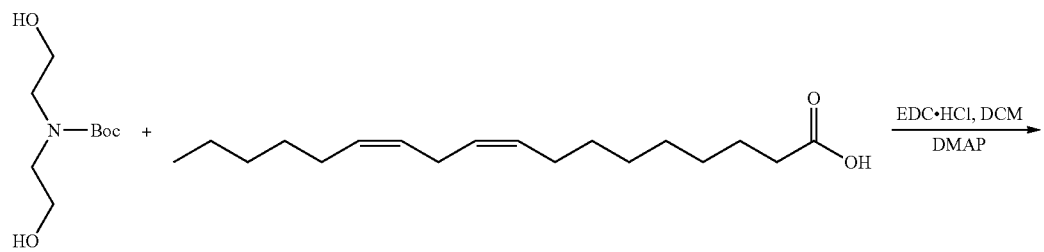

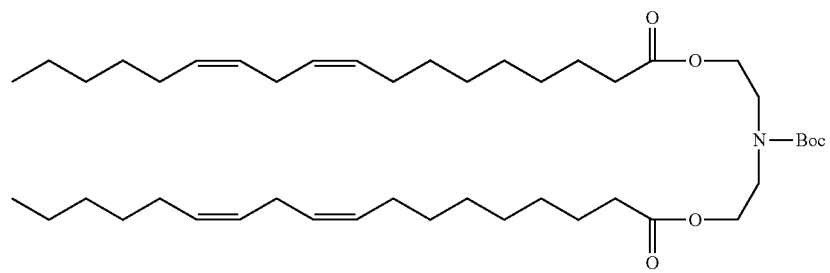

N-Boc-diethanolamine (5 g, 24.4 mmol), linoleic acid (14.4 g, 51.2 mmol) and was dissolved in DCM (100 mL). EDC HCl salt (10.3 g, 53.7 mmol) was added followed by DMAP (596 mg, 4.88 mmol). The reaction was allowed to stir for about 12 hours at room temperature under a blanket of inert gas. Thereafter, 50 mL of water and 50 mL of methanol were added, and the mixture was stirred for 10 min. The organic layer was isolated and the aqueous layer was further extracted with DCM (150 mL). The combined organics were dried ($MgSO_4$) for 10 min, filtered and concentrated. Purification was by silica gel chromatography, eluting with a hexane/ethyl acetate gradient yielded (9Z,9'Z, 12Z,12'Z)-((tert-butoxycarbonyl)azanediyl)bis(ethane-2,1-diyl)bis(octadeca-9,12-dienoate) (15.9 g).

Step 2: Preparation of Intermediate 2: (9Z,9'Z,12Z,12'Z)-azanediylbis(ethane-2,1-diyl) bis(octadeca-9,12-dienoate)

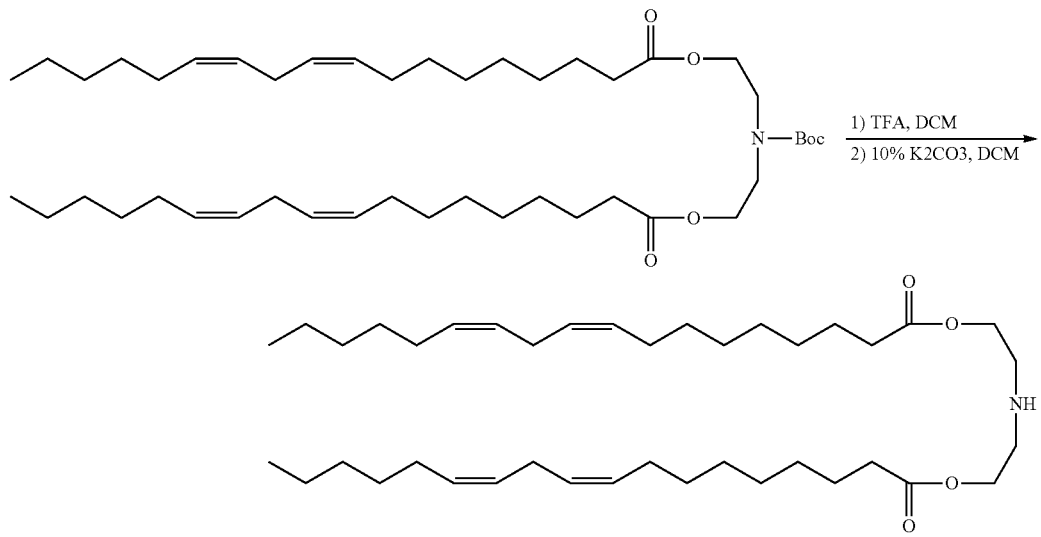

To (9Z,9'7,12Z,12'Z)-((tert-butoxycarbonyl)azanediyl)bis (ethane-2,1-diyl) bis(octadeca-9,12-dienoate) (5.33 g, 7.30 mmol) in a round-bottom flask was added DCM (50 mL) and placed into an ice-bath. TFA (50 mL) was added and the mixture was allowed to stir for 30 min. The reaction mixture was then concentrated. Toluene was added to the residue to aid in azeotroping off excess TFA. The residue was placed back in the ice bath and 10% $K_2CO_3$ (50 mL) and DCM (50 mL) were added. The mixture was stirred for 15 min and the organic layer isolated. The turbid aqueous layer was extracted with DCM (20 mL). The combined organics were dried ($MgSO_4$), filtered and concentrated to yield (9Z,9'Z, 12Z,12'Z)-azanediylbis(ethane-2,1-diyl)bis(octadeca-9,12-dienoate) (Quantitative).

Step 3: Preparation of 5104-DLin: (9Z,9'Z,12Z,12'Z)-((2-((2-(dimethylamino)ethyl)thio)acetyl)azanediyl)bis(ethane-2,1-diyl)bis(octadeca-9,12-dienoate)

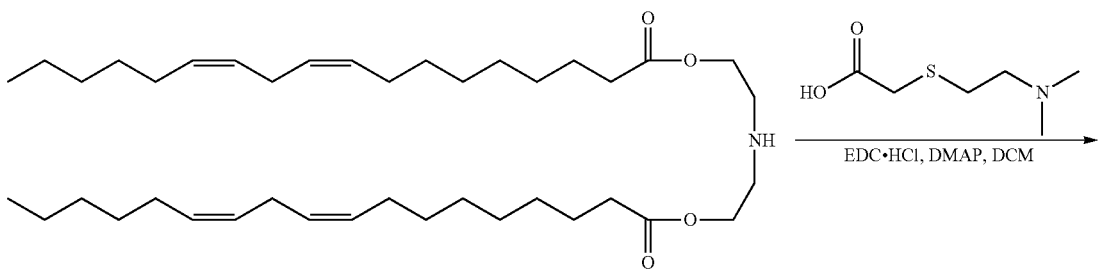

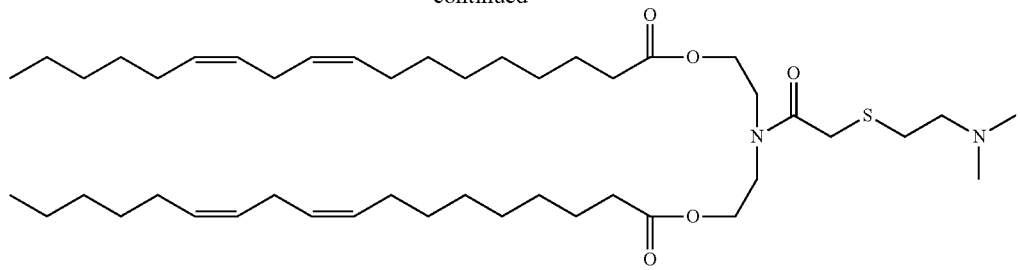

A mixture of (9Z,9'Z,12Z,12'Z)-azanediylbis(ethane-2,1-diyl) bis(octadeca-9,12-dienoate) (4.68 g, 7.30 mmol), 2-((2-(dimethylamino)ethyl)thio)acetic acid (1.43 g, 8.76 mmol) and EDC HCl salt (2.10 g, 10.95 mmol) were suspended in DCM (100 mL). DMAP (89 mg, 0.73 mmol) was added, stirred at room temperature for 12 hours. Fifty mL each of water and methanol were added and, after stirring for 10 minutes, the clear organic phase was isolated. The turbid aqueous phase was extracted with DCM (2×20 mL) and washed combined organic extracts with PBS (pH11, 100 mL). The product was dried with MgSO$_4$, filtered and concentrated. Purification was by silica gel chromatography eluting with a MeOH in DCM gradient. Pooled and concentrated fractions yielded (9Z,9',12Z,12'Z)-((2-((2-(dimethylamino)ethyl)thio)acetyl)azanediyl)bis(ethane-2,1-diyl) bis(octadeca-9,12-dienoate) (4.3 g). LCMS ESI+: m/z 775.9 (M+H).

Preparation of (9Z,9'Z,12Z,12'Z)-((((2-(dimethylamino)ethyl)thio)carbonyl)azanediyl)bis(octadeca-9,12-dienoate) (TU104-DLin)

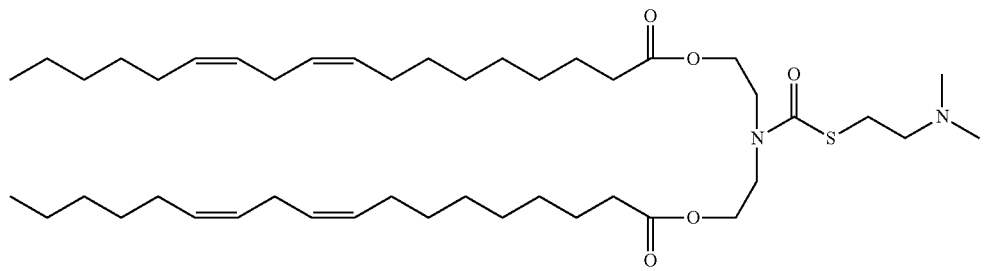 [SMILES: CCCCC/C=C\C/C=C\CCCCCCCC(=O)OCCN(CCOC(=O)CCCCCCC/C=C\C/C=C\CCCCC)C(=O)SCCN(C)C]

Step 1: Preparation of TU104-Dlin: (9Z,9',12Z,12'Z)-((((2-(dimethylamino)ethyl)thio)carbonyl)azanediyl)bis(ethane-2,1-diyl)bis(octadeca-9,12-dienoate)

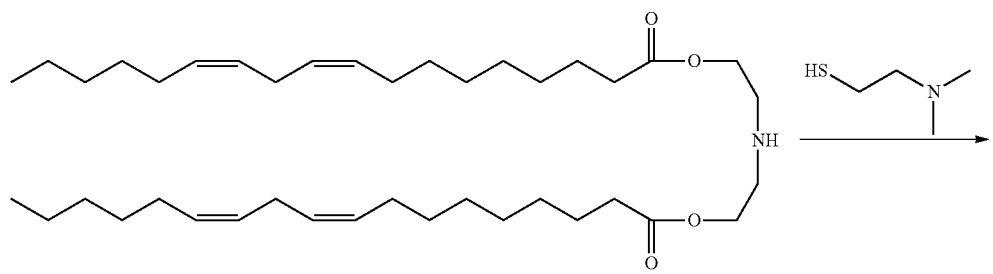

-continued

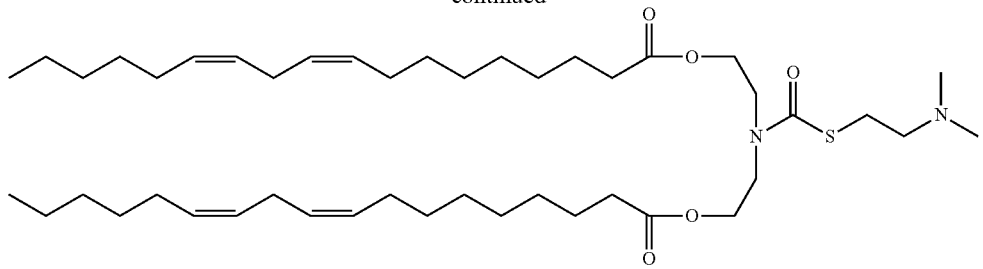

Synthesis of (9Z,9'Z,12Z,12'Z)-azanediylbis(ethane-2,1-diyl) bis(octadeca-9,12-dienoate) was previously described. Trichloromethyl chloroformate (aka diphosgene) (740 µL) was added to a solution (9Z,9',12Z,12'Z)-azanediylbis(ethane-2,1-diyl) bis(octadeca-9,12-dienoate) (2.6 g) in dry DCM (40 mL) and stirred under a blanket of argon at room temperature for 12 hours. DCM and excess diphosgene were removed in vacuo. 2-(dimethylamino)ethane thiol HCl salt (2.9 g), DCM (40 mL) and triethylamine (3.7 mL) were then added. After 16 h at room temperature the reaction mixture was diluted with DCM and washed with 10% $K_2CO_3$ (75 mL), dried ($MgSO_4$), filtered, and concentrated. Purification was purified by silica gel chromatography eluting with ethyl acetate followed by a DCM/MeOH gradient to yield (9Z,97,12Z,12'Z)-((((2-(dimethylamino)ethyl)thio)carbonyl)azanediyl)bis(ethane-2,1-diyl)bis(octadeca-9,12-dienoate) (850 mg). LCMS ESI+: m/z 761.9 (M+H).

Formation of non-diVA siRNA containing liposomes. Ionizable lipid, DOPE, cholesterol, and a PEG-conjugated lipid were solubilized in absolute EtOH at a final weight concentration of ~4.4 mg/mL. The siRNA was solubilized in citrate buffer at a concentration ~0.26 mg/mL and the temperature was adjusted to 35-40° C. The ethanol/lipid mixture was then added to the siRNA-containing buffer while stirring to spontaneously form siRNA loaded liposomes. Lipids were combined with siRNA to reach a final total lipid to siRNA ratio of 7:1 to 14:1 (wt:wt). The siRNA loaded liposomes were diafiltered against 10× volumes of PBS to remove ethanol and exchange the buffer. Final product was filtered through 0.22 µm, sterilizing grade, filter for bioburden reduction. This process yielded liposomes with a mean particle diameter of 40-100 nm, PDI<0.2, and >85% RNA encapsulation (entrapment) efficiency.

Formation of siRNA containing liposomes co-solubilized with diVA_siRNA-diVA-Liposome formulations were prepared using the method described above. diVA-PEG-diVA was co-solubilized in absolute ethanol with the other lipids (ionizable lipid, DOPE, cholesterol, and PEG-conjugated lipids) prior to addition to the siRNA containing buffer. Molar content of diVA-PEG-diVA ranged from 0.1 to 5 mol %. This process yielded liposomes with a mean particle diameter of 40-100 nm, PDI<0.2, and >85% entrapment efficiency.

Formation of siRNA containing liposomes with ionizable and cationic lipids. siRNA-diVA-Liposome formulations and siRNA-Liposome formulations were prepared using the method described above. Cationic lipid was co-solubilized in absolute ethanol with the other lipids (ionizable lipid, DOPE, cholesterol, PEG-conjugated lipids, and diVA-PEG-diVA) prior to addition to the siRNA containing buffer. Molar content of cationic lipid ranged from 5 to 40 mol %. This process yielded liposomes with a mean particle diameter of 40-100 nm, PDI<0.2, and >85% entrapment efficiency.

In Vitro (pHSC, gp46 KD @20 nM) Efficacy

PHSCs in 96-well plate were incubated with formulation that composed of either ionizable lipid formulation C104, ionizable lipid formulation Tu104, or combination formulations with different ratio of ionizable lipids (C104:Tu104). After 30 minutes, medium was replaced with fresh growth medium. Forty eight hours later, cells were lysed and gp46 and GAPDH mRNA levels measured by quantitative RT-PCR (TAQMAN®) assay, and gp46 levels were normalized to GAPDH levels. Normalized gp46 levels were expressed as percent of mock control cells. Error bars indicate standard deviations (n=3). Results are depicted in FIG. 1. As the results demonstrate, the combination of two ionizable lipids of the description resulted in observed synergistic reduction in gene expression.

Figure 2:
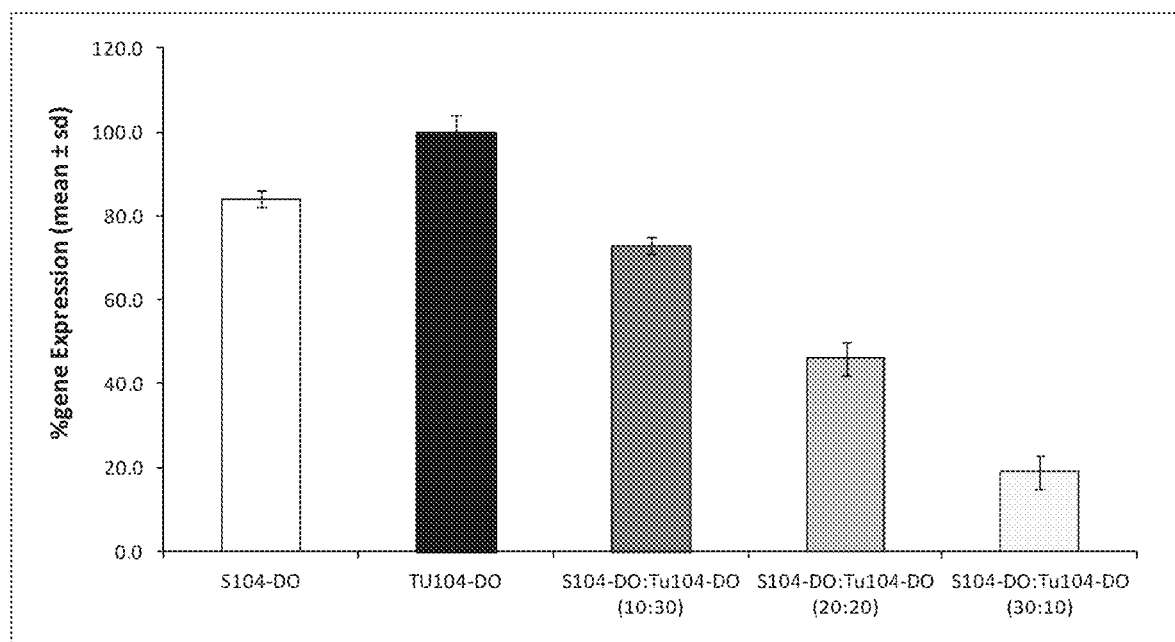
FIG. 2 depicts in vitro synergistic efficacy of ionizable lipid:ionizable lipid embodiments of the present description
Figure 3:
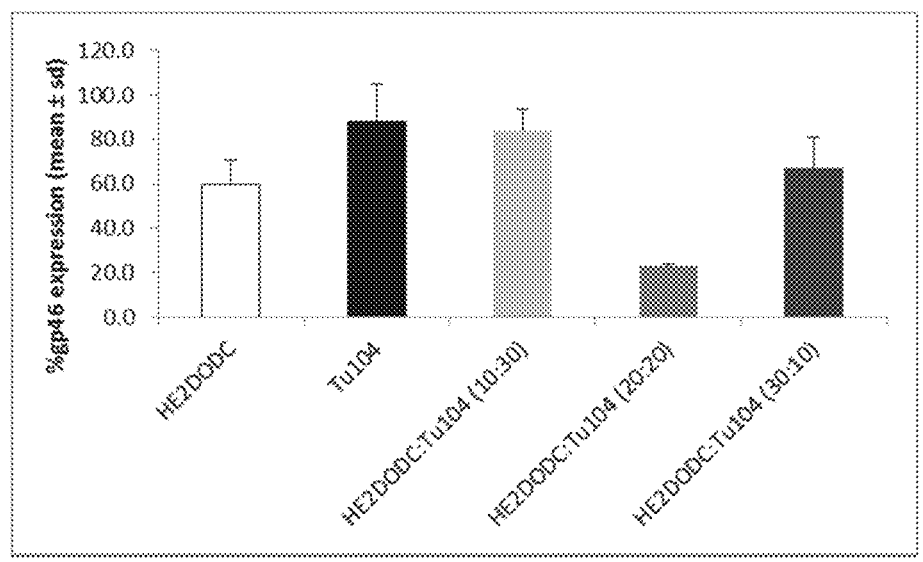
FIG. 3 depicts in vitro synergistic efficacy of ionizable lipid:cationic lipid embodiments of the present description

Similar experiments were carried out with other ionizable lipid:ionizable lipid and ionizable lipid:cationic lipid combinations. Results for D104-DO:Tu104-DO combinations are depicted in FIG. 2. Results for HEDODC:Tu104 combinations are depicted in FIG. 3. Combinations of both ionizable lipids and ionizable:cationic lipids again resulted in synergistic reduction in gene expression.

Figure 4:
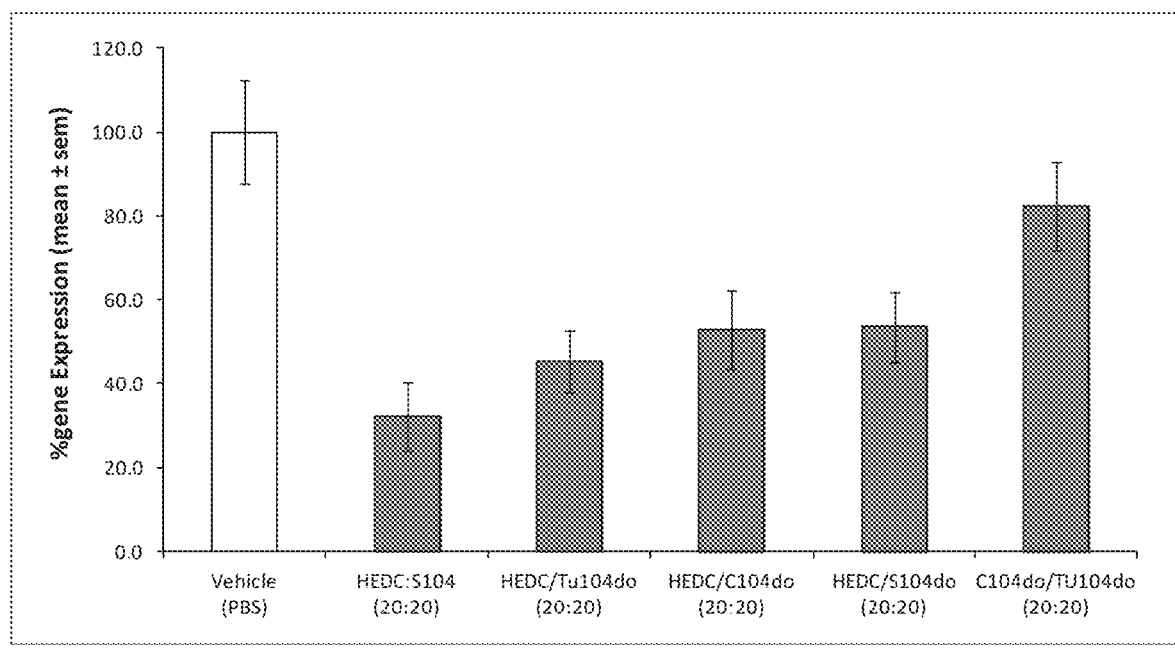
FIG. 4 depicts in vivo efficacy of ionizable lipid:cationic lipid embodiments of the present description

In Vivo (DMNQ) Efficacy:

In vivo activity of target formulation was evaluated in the short-term liver damage model (referred to herein as the Quick Model or DMNQ). In this model, the short-term liver damage induced by treatment with a hepatotoxic agent such as dimethylnitrosamine (DMN) is accompanied by the elevation of gp46 mRNA levels. To induce these changes, male Sprague-Dawley rats were injected intraperitoneally with DMN on six consecutive days. At the end of the DMN treatment period, the animals were randomized to groups based upon individual animal body weight. Formulations was administered as a single IV dose, one hour after the last injection of DMN. After 24 hours, liver lobes were excised and both gp46 and MRPL19 mRNA levels were determined by quantitative RT-PCR (TAQMAN®) assay. mRNA levels for gp46 were normalized to MRPL19 levels. Results are depicted in FIG. 4. Several combinations of ionizable:cationic lipids achieved 50% reduction in gene expression for a single, 0.5 mg per kg of animal body weight, dose of encapsulated siRNA.

In Vitro Toxicology Data, In Vitro Cytotoxicity (HepG2 @200 nM)

Addition of 20 mol % of S104 into formulations of the description improved cell viability in a HepG2 cytotoxicity assay improved from 27% to 52%.

| Formulation | % viability |
|---|---|
| 40:30:25:5:2 (HEDC:DOPE:Cholesterol:Peg-lipid:DiVA) | 27 ± 5.3% |
| 20:20:30:25:5:2 (HEDC:S104:DOPE:Cholesterol:Peg-lipid:DiVA) | 52 ± 10% |

HepG2 Cytotoxicity Assay Description:

HepG2 cells, an adherent cell line derived from human hepatocellular carcinoma, was cultured in MEM/EBSS (HYCLONE™, Logan, Utah, Cat #SH30024.01) supplemented with 10% FBS (HYCLONE™ Cat #SH30910). HepG2 cells were seeded in 96-well OPTILUX® black plates (BD FALCON™, Cat #BD353220) at 5000 cells/well overnight. Formulations were added to each well to final indicated siRNA concentration (n=3). At 48 h post formulation addition, cell viability was determined using CELLTITER-GLO® Luminescent Cell Viability Assay Kit (Promega, Cat #G7572) following manufacture's instruction. Chemiluminescent signal were measured on CLARITY™ Luminescence Microplate Reader (BIOTEK®, Winooski, Vt.). Viability was calculated based on % of chemiluminescent signal in formulation treated well normalized against mock treated wells.

In Vivo Toxicology Data

The HEDC:S104 (20:20) formulation of the present description is exceptionally well tolerated as shown in toxicity studies. No toxicity was observed when the formulation was injected intravenously in rats and monkey at doses up to 25 mg/kg and 12 mg/kg, respectively, which is considered by those skilled in the art to be superior.

Transfection with Formulations of the Description:

Transfection method is same for LX-2 and pHSCs. The liposome formulations or lipoplex formulations of the description were mixed with growth medium at desired concentrations. 100 µl of the mixture was added to the cells in 96-well plate and cells were incubated for 30 min at 37° C. in the incubator with 5% $CO_2$. After 30 min, medium was replaced with fresh growth medium. After 48 h of transfection, cells were processed using CELLS-TO-CT™ lysis reagents (APPLIED BIOSCIENCES™) according to the manufacturer's instructions.

Quantitative (q) RT-PCR for Measuring HSP47 mRNA Expression

HSP47 and GAPDH TAQMAN® assays and One-Step RT-PCR master mix were purchased from APPLIED BIOSCIENCES™. Each PCR reaction contained the following composition: One-step RT-PCR mix 5 µl, TAQMAN® RT enzyme mix 0.25 TAQMAN® gene expression assay probe (HSP47) 0.25 TAQMAN® gene expression assay probe (GAPDH) 0.5 RNase free water 3.25 cell lysate 0.75 total volume 10 µl. GAPDH was used as endogenous control for the relative quantification of HSP47 mRNA levels. Quantitative RT-PCR was performed in ViiA™ 7 Real-Time PCR system (APPLIED BIOSCIENCES™). All values were normalized to the average HSP47 expression of the mock transfected cells and expressed as percentage of HSP47 expression compared to mock.

What is claimed:

1. A compound of formula I:

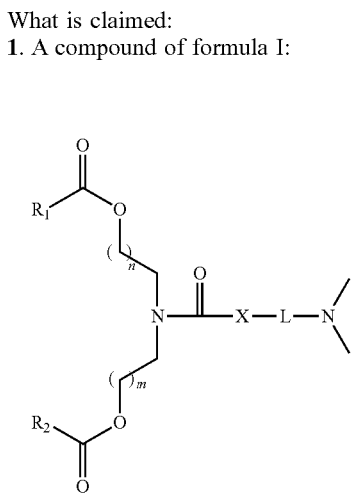

wherein
n and m are independently 1, 2, 3, or 4;
$R_1$ and $R_2$ are independently $C_{10-18}$alkyl- or $C_{12-18}$alkenyl-;

X is —$CH_2$—, and L is —$OC(O)C_{1-4}$ alkylene-; or
X is absent, and L is —$OC_{1-4}$ alkylene- or —$OC(O)C_{1-4}$ alkylene-; or
X is O or N, and L is —$C_{1-4}$ alkylene-;
or a pharmaceutically acceptable salt form thereof.

2. The compound of claim 1, wherein n and m are independently 1 or 2.

3. The compound of claim 2, wherein X is absent.

4. The compound of claim 3, wherein L is —$OC_{1-4}$ alkylene- or —$OC(O)C_{1-4}$ alkylene-.

5. The compound of claim 1, wherein X is —$CH_2$—.

6. The compound of claim 5, wherein L is —$OC(O)CH_2CH_2CH_2$—.

7. The compound of claim 2, wherein X is O.

8. The compound of claim 2, wherein $R_1$ and $R_2$ are each $C_{10-18}$alkyl-.

9. The compound of claim 2, wherein $R_1$ and $R_2$ are each $C_{13}$alkyl-.

10. A pharmaceutical composition comprising the compound of claim 1.

11. The pharmaceutical composition of claim 10 comprising a therapeutically effective amount of RNA.

12. A compound selected from the group consisting of

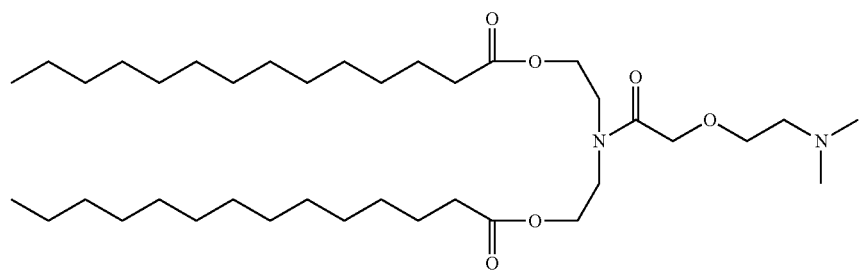

O104

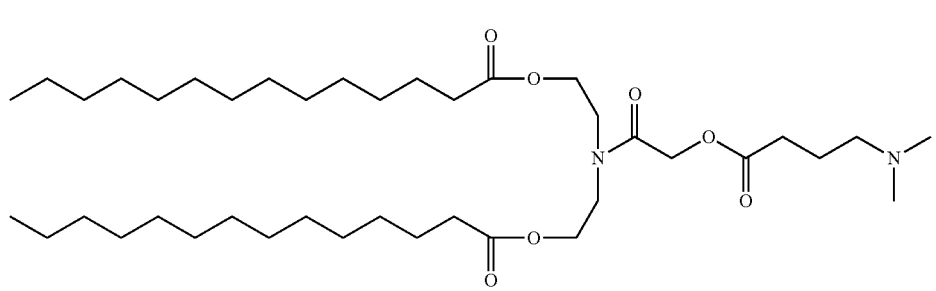
HEDC-M1
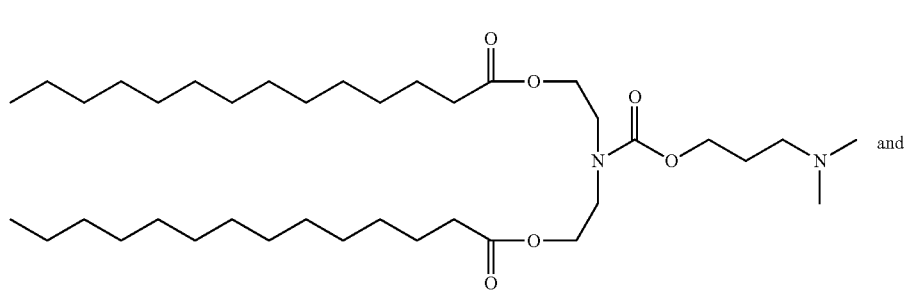
CB104
and
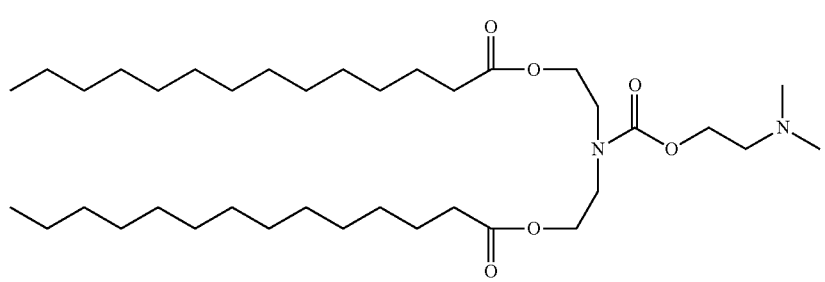
CA104
13. A pharmaceutical composition comprising the compound of claim 12.
14. The pharmaceutical composition of claim 13 comprising a therapeutically effective amount of RNA.
15. A compound selected from the group consisting of
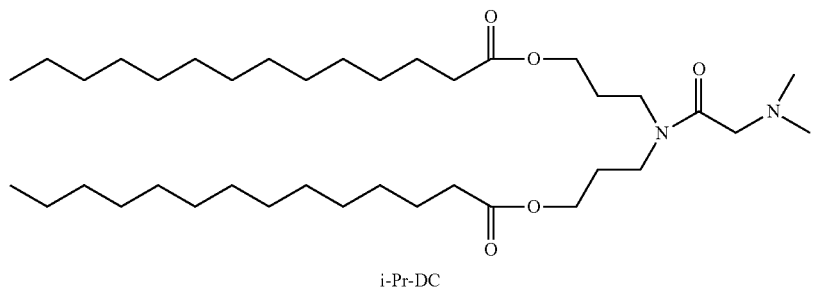
i-Pr-DC -continued
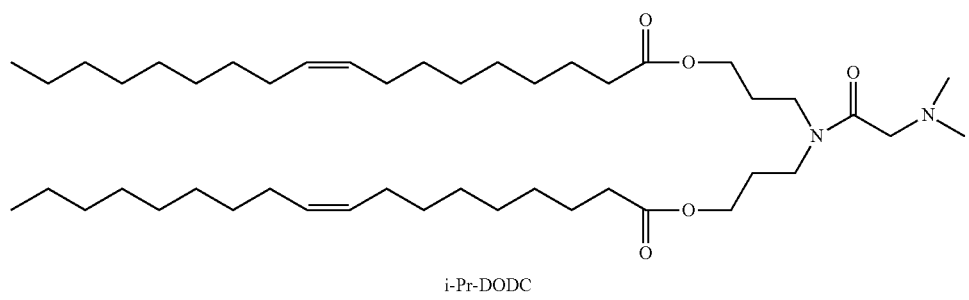
i-Pr-DODC
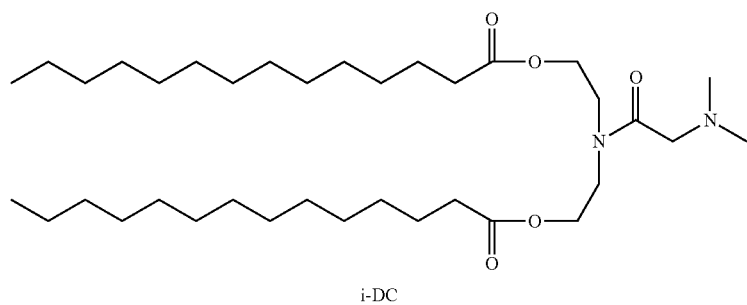
i-DC
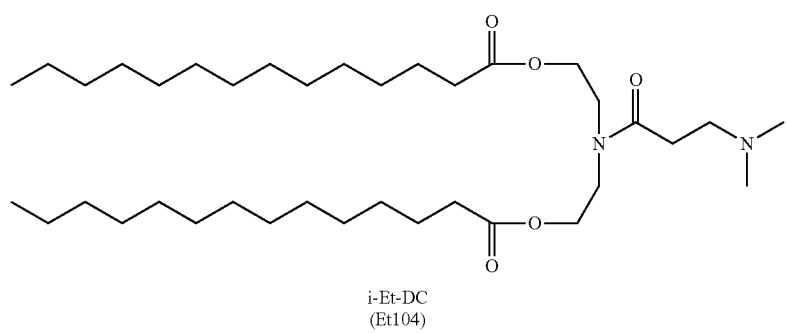
i-Et-DC
(Et104)
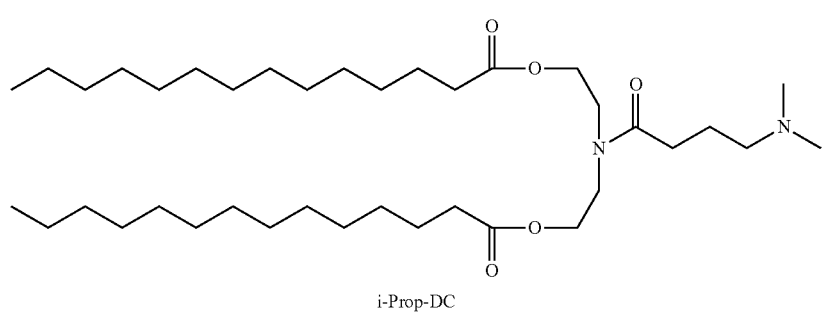
i-Prop-DC
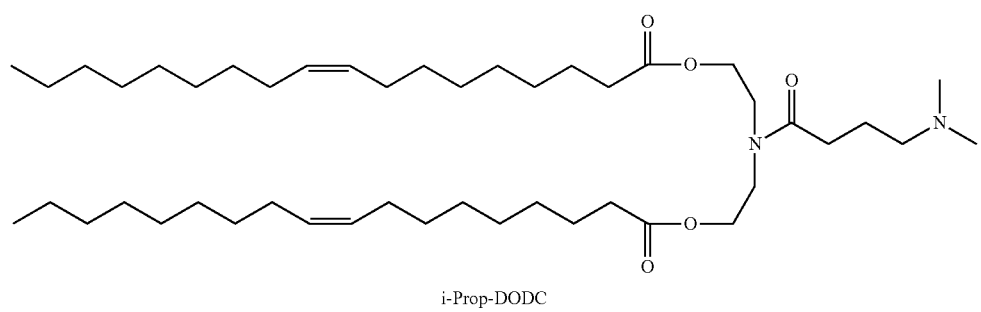
i-Prop-DODC -continued
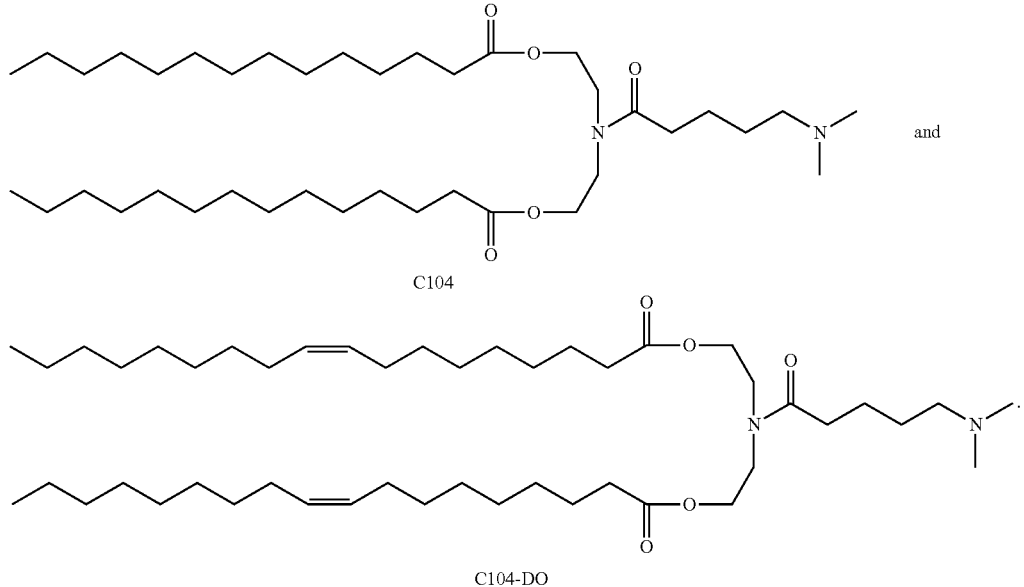
16. A pharmaceutical composition comprising the compound of claim 15.
17. The pharmaceutical composition of claim 16 comprising a therapeutically effective amount of RNA.

UNITED STATES PATENT AND TRADEMARK OFFICE
CERTIFICATE OF CORRECTION

| | |
|---|---|
| PATENT NO. | : 11,103,583 B2 |
| APPLICATION NO. | : 16/460812 |
| DATED | : August 31, 2021 |
| INVENTOR(S) | : Joseph E. Payne et al. |

It is certified that error appears in the above-identified patent and that said Letters Patent is hereby corrected as shown below:

In the Specification

Column 1, Line 49, delete "("PEP")," and insert -- ("PEI"), --.

Column 2, Line 34 approx., delete "$C_{1-4}$alkylene," and insert -- $C_{1-4}$ alkylene, --.

Column 2, Line 59, delete "description" and insert -- description. --.

Column 3, Line 32 approx., delete "$C_{1-4}$alkylene," and insert -- $C_{1-4}$ alkylene, --.

Column 3, Line 57 approx., delete "$C_{1-4}$alkylene" and insert -- $C_{1-4}$ alkylene --.

Column 3, Lines 65-66, delete "-$CH_2$ $CH_2CH_2$-, and -$CH_2$ $CH_2CH_2CH_2$-." and insert -- -$CH_2CH_2CH_2$-, and -$CH_2CH_2CH_2CH_2$-. --.

Column 4, Line 4 approx., delete "$C_{1-4}$alkylene," and insert -- $C_{1-4}$ alkylene, --.

Column 4, Lines 18-19 approx., delete "-S-$CH_2$ $CH_2CH_2$-, and -S-$CH_2$ $CH_2CH_2CH_2$-." and insert -- -S-$CH_2CH_2CH_2$-, and -S-$CH_2CH_2CH_2CH_2$-. --.

Column 4, Lines 26-27 approx., delete "-O-$CH_2$ $CH_2CH_2$-, and -O-$CH_2$ $CH_2CH_2CH_2$-." and insert -- -O-$CH_2CH_2CH_2$-, and -O-$CH_2CH_2CH_2CH_2$-. --.

Column 4, Line 29 approx., delete "$C_{1-4}$alkylene." and insert -- $C_{1-4}$ alkylene. --.

Column 4, Lines 30-31 approx., delete "-$CH_2$ $CH_2CH_2$-, and -$CH_2$ $CH_2CH_2CH_2$-." and insert -- -$CH_2CH_2CH_2$-, and -$CH_2CH_2CH_2CH_2$-. --.

Column 4, Line 34 approx., delete "-$CH_2$ $CH_2CH_2$-, and -$CH_2$ $CH_2CH_2CH_2$-." and insert -- -$CH_2CH_2CH_2$-, and -$CH_2CH_2CH_2CH_2$-. --.

Signed and Sealed this
Thirty-first Day of January, 2023

*Katherine Kelly Vidal*
Katherine Kelly Vidal
*Director of the United States Patent and Trademark Office*

CERTIFICATE OF CORRECTION (continued)
U.S. Pat. No. 11,103,583 B2

Column 4, Line 39 approx., delete "More" and insert -- In more --.

Column 6, Line 10 approx., delete "In is" and insert -- It is --.

Column 7-8, Line 48 approx., delete "(OCH$_2$CH$_2$)$_q$" and insert -- (OCH$_2$CH$_2$)q --.

Column 7-8, Line 48 approx., delete "(CH$_2$CH$_2$O)$_r$" and insert -- (CH$_2$CH$_2$O)r --.

Column 7-8, Line 48 approx., delete "(OCHCH$_2$)$_s$" and insert -- (OCHCH$_2$)s --.

Column 14, Line 21 approx., delete "Alternatively" and insert -- Alternatively, --.

Column 15, Line 3, delete "Alternatively" and insert -- Alternatively, --.

Column 58, Line 31 approx., delete "((2-((2-" and insert -- ((2-(2- --.

Column 64, Line 2, delete "(C$_{104}$-DO)" and insert -- (C104-DO) --.

Column 66, Line 38 approx., delete "(((2-" and insert -- ((((2- --.

Column 67-68, Lines 40-44 approx., delete " 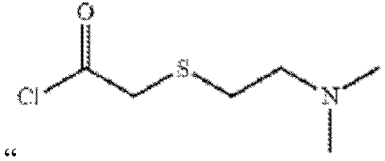 " and insert 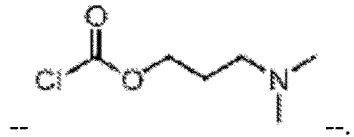 -- -- .

Column 69, Lines 8-9 approx., delete "(87 mg).)." and insert -- (87 mg). --.

Column 72, Line 31, delete "((((2" and insert -- (((2 --.

Column 75, Line 1, delete "((2-" and insert -- ((2-((2- --.

Column 75, Line 51 approx., delete "water" and insert -- Water --.

Column 76, Line 47 approx., delete "min minutes." and insert -- minutes. --.

Column 77, Lines 44-49 approx., delete " 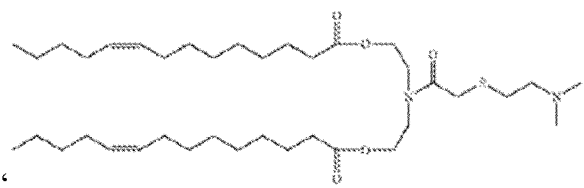 " and insert

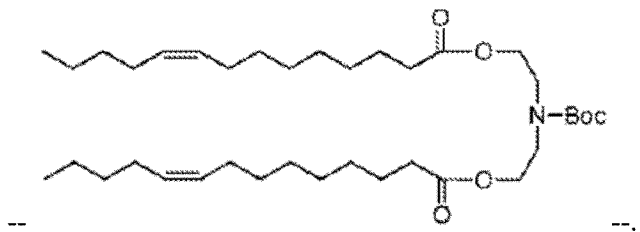
--                                                                                                          --.

Column 77, Line 65, delete "(9Z,97)" and insert -- (9Z,9'Z) --.

Column 83, Line 5, delete "HOBt H$_2$O" and insert -- HOBt·H$_2$O --.

Column 83, Line 24 approx., delete "(9Z,9',Z,12Z,12'Z)" and insert -- (9Z,9'Z,12Z,12'Z) --.

Column 86, Line 33, delete "(9Z,97,12Z,12'Z)" and insert -- (9Z,9'Z,12Z,12'Z) --.

Column 86, Line 46, delete "5104-DLin" and insert -- S104-DLin --.

Column 87, Line 27, delete "(9Z,9',Z,12Z,12'Z)" and insert -- (9Z,9'Z,12Z,12'Z) --.

Column 87, Line 35 approx., delete "(9Z,9',12Z,12'Z)" and insert -- (9Z,9'Z,12Z,12'Z) --.

Column 89, Line 16 approx., delete "(740 μL)" and insert -- (740 μL,) --.

Column 89, Line 17 approx., delete "(9Z,9',12Z,12'Z)" and insert -- (9Z,9'Z,12Z,12'Z) --.

Column 89, Lines 28-29 approx., delete "(9Z,97,12Z,12'Z)" and insert -- (9Z,9'Z,12Z,12'Z) --.

Column 90, Line 36 approx., delete "D104" and insert -- S104 --.

Column 92, Line 20, delete "0.25" and insert -- 0.25 μl --.

Column 92, Line 21, delete "0.25" and insert -- 0.25 μl --.

Column 92, Line 22, delete "0.5" and insert -- 0.5 μl --.

Column 92, Line 22, delete "3.25" and insert -- 3.25 μl --.

Column 92, Line 22, delete "0.75" and insert -- 0.75 μl --.

In the Claims

Column 93, Lines 48-49 approx., Claim 1, delete "C$_{10-18}$alkyl- or C$_{12-18}$alkenyl-;" and insert -- C$_{10-18}$ alkyl- or C$_{12-18}$ alkenyl-; --.

CERTIFICATE OF CORRECTION (continued)
U.S. Pat. No. 11,103,583 B2

Column 94, Line 42, Claim 8, delete "$C_{10-18}$alkyl-." and insert -- $C_{10-18}$ alkyl-. --.

Column 94, Line 44, Claim 9, delete "$C_{13}$alkyl-." and insert -- $C_{13}$ alkyl-. --.